US012150740B2

(12) United States Patent
Gopalakrishnan

(10) Patent No.: US 12,150,740 B2
(45) Date of Patent: Nov. 26, 2024

(54) TOTALLY NON-INVASIVE BLOOD SUGAR LEVEL MONITORING APPARATUS INTEGRATED WITH REAL-TIME HEALTH SUPPORT SYSTEM

(71) Applicant: Muralidharan Gopalakrishnan, Thane (IN)

(72) Inventor: Muralidharan Gopalakrishnan, Thane (IN)

(73) Assignee: Muralidharan Gopalakrishnan, Maharashtra (IN)

( * ) Notice: Subject to any disclaimer, the term of this patent is extended or adjusted under 35 U.S.C. 154(b) by 1071 days.

(21) Appl. No.: 16/961,778

(22) PCT Filed: Jan. 13, 2019

(86) PCT No.: PCT/IB2019/050253
§ 371 (c)(1),
(2) Date: Jul. 13, 2020

(87) PCT Pub. No.: WO2019/138382
PCT Pub. Date: Jul. 18, 2019

(65) Prior Publication Data
US 2021/0059542 A1 Mar. 4, 2021

Related U.S. Application Data

(60) Provisional application No. 62/617,273, filed on Jan. 14, 2018.

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0002* (2013.01); *A61B 5/0022* (2013.01);
(Continued)

(58) Field of Classification Search
CPC ... A61B 5/0075; A61B 5/1455; A61B 5/0205; A61B 5/02055; A61B 5/0002;
(Continued)

(56) References Cited

U.S. PATENT DOCUMENTS

2014/0121527 A1* 5/2014 Adler, Jr. ............. A61B 5/0036
600/473
2016/0150978 A1* 6/2016 Yuen .................... A61B 5/0205
600/301

(Continued)

*Primary Examiner* — Matthew Kremer
*Assistant Examiner* — Elina Sohyun Jang

(57) ABSTRACT

A non-invasive continuous blood sugar level monitoring apparatus integrated with real-time health support system. The blood sugar levels and other vital physiological information of the user can also be tracked wirelessly through the apparatus. The apparatus has an integrated real-time alert and reminder feature for notifying the user during medication and unusual physiological conditions. An automated diet and lifestyle recommendation solution is integrated into the device to help the user maintain healthy blood sugar and blood pressure levels. The low-powered telemetry device is used for communicating the stored physiological information of the user and the computed results between the network of devices.

24 Claims, 47 Drawing Sheets

(51) Int. Cl.
| | |
|---|---|
| A61B 5/053 | (2021.01) |
| A61B 5/11 | (2006.01) |
| A61B 5/145 | (2006.01) |
| A61B 5/1455 | (2006.01) |
| A61B 5/16 | (2006.01) |
| A61J 7/04 | (2006.01) |
| G01J 3/02 | (2006.01) |
| G01J 3/10 | (2006.01) |
| G01J 3/28 | (2006.01) |
| G01J 3/45 | (2006.01) |
| G01P 15/18 | (2013.01) |
| G05B 19/042 | (2006.01) |
| G06Q 50/00 | (2012.01) |
| G16H 10/65 | (2018.01) |
| G16H 20/10 | (2018.01) |
| G16H 20/60 | (2018.01) |
| G16H 20/70 | (2018.01) |
| G16H 40/20 | (2018.01) |
| G16H 40/40 | (2018.01) |
| G16H 40/67 | (2018.01) |
| G16H 50/20 | (2018.01) |
| G16H 50/30 | (2018.01) |
| G16H 50/50 | (2018.01) |
| G16H 50/70 | (2018.01) |
| G16H 70/20 | (2018.01) |
| A61B 5/01 | (2006.01) |
| A61B 5/021 | (2006.01) |
| A61B 5/024 | (2006.01) |
| G06F 3/01 | (2006.01) |
| G06F 3/0488 | (2022.01) |
| H02J 7/00 | (2006.01) |
| H02J 7/02 | (2016.01) |
| H02J 7/34 | (2006.01) |
| H02J 50/10 | (2016.01) |

(52) U.S. Cl.
CPC ............ *A61B 5/0205* (2013.01); *A61B 5/053* (2013.01); *A61B 5/1112* (2013.01); *A61B 5/14532* (2013.01); *A61B 5/14551* (2013.01); *A61B 5/14552* (2013.01); *A61B 5/165* (2013.01); *A61B 5/4809* (2013.01); *A61B 5/486* (2013.01); *A61B 5/4872* (2013.01); *A61B 5/6803* (2013.01); *A61B 5/681* (2013.01); *A61B 5/6816* (2013.01); *A61B 5/6826* (2013.01); *A61B 5/6831* (2013.01); *A61B 5/721* (2013.01); *A61B 5/7214* (2013.01); *A61B 5/7217* (2013.01); *A61B 5/7246* (2013.01); *A61B 5/7257* (2013.01); *A61B 5/7267* (2013.01); *A61B 5/742* (2013.01); *A61B 5/746* (2013.01); *A61B 5/747* (2013.01); *A61B 5/7475* (2013.01); *A61B 5/748* (2013.01); *A61J 7/04* (2013.01); *G01J 3/0286* (2013.01); *G01J 3/108* (2013.01); *G01J 3/2803* (2013.01); *G01J 3/45* (2013.01); *G01P 15/18* (2013.01); *G05B 19/042* (2013.01); *G06Q 50/01* (2013.01); *G16H 10/65* (2018.01); *G16H 20/10* (2018.01); *G16H 20/60* (2018.01); *G16H 20/70* (2018.01); *G16H 40/20* (2018.01); *G16H 40/40* (2018.01); *G16H 40/67* (2018.01); *G16H 50/20* (2018.01); *G16H 50/30* (2018.01); *G16H 50/50* (2018.01); *G16H 50/70* (2018.01); *G16H 70/20* (2018.01); *A61B 5/01* (2013.01); *A61B 5/021* (2013.01); *A61B 5/02141* (2013.01); *A61B 5/024* (2013.01); *A61B 5/02427* (2013.01); *A61B 5/02433* (2013.01); *A61B 2560/0214* (2013.01); *A61B 2560/0223* (2013.01); *A61B 2560/0238* (2013.01); *A61B 2560/0252* (2013.01); *A61B 2562/0219* (2013.01); *A61B 2562/0242* (2013.01); *A61B 2562/028* (2013.01); *A61B 2562/0285* (2013.01); *G05B 2219/2639* (2013.01); *G06F 3/017* (2013.01); *G06F 3/0488* (2013.01); *H02J 7/0045* (2013.01); *H02J 7/02* (2013.01); *H02J 7/345* (2013.01); *H02J 50/10* (2016.02)

(58) Field of Classification Search
CPC ... A61B 5/0022; A61B 5/053; A61B 5/14532; A61B 5/14551; A61B 5/24; A61B 5/6803; A61B 5/681; A61B 5/6816; A61B 5/721; A61B 5/7214; A61B 5/7217; A61B 5/7257; A61B 5/7267; A61B 5/742; A61B 5/747; A61B 5/1112; A61B 5/14552; A61B 5/165; A61B 5/4809; A61B 5/486; A61B 5/4872; A61B 5/6826; A61B 5/6831; A61B 5/7246; A61B 5/746; A61B 5/7475; A61B 5/748; A61B 5/01; A61B 5/021; A61B 5/02141; A61B 5/024; A61B 5/02427; A61B 5/02433; A61B 2560/0214; A61B 2560/0223; A61B 2560/0238; A61B 2560/0252; A61B 2562/0219; A61B 2562/0242; A61B 2562/028; A61B 2562/0285; G01N 21/359; G01N 21/3151; G01J 3/45; G01J 3/02; G01J 3/108; G01J 3/0286; G01J 3/2803; G01P 15/18; G05B 19/042; G05B 2219/2639; A61J 7/04; G06Q 50/01; G16H 10/65; G16H 20/10; G16H 20/60; G16H 20/70; G16H 40/20; G16H 40/40; G16H 40/67; G16H 50/20; G16H 50/30; G16H 50/50; G16H 50/70; G16H 70/20; G06F 3/017; G06F 3/0488; H02J 7/0045; H02J 7/02; H02J 7/345; H02J 50/10

See application file for complete search history.

(56) References Cited

U.S. PATENT DOCUMENTS

| | | | |
|---|---|---|---|
| 2016/0270656 A1* | 9/2016 | Samec | A61B 3/113 |
| 2016/0324478 A1* | 11/2016 | Goldstein | A61B 5/11 |
| 2018/0177459 A1* | 6/2018 | Eletr | A61B 5/02125 |
| 2018/0184972 A1* | 7/2018 | Carmi | G01J 3/2803 |
| 2019/0129470 A1* | 5/2019 | Hasei | G04R 20/02 |

* cited by examiner

DIET RECORDING

180 → Enter Your Meal Name: _____

181 → Qty: _____

182 → Record the nutrition level:
    Protein:
    Carbohydrates:
    Sugar:
    Total Fat:
    Unsaturated Fat:
    Saturated Fat:
    Trans Fat:
    Vitamin A:
    Vitamin C:
    Vitamin D:
    Calcium:
    Iron:
    Sodium:
    Cholesterol:

TOTALLY NON-INVASIVE BLOOD SUGAR LEVEL MONITORING APPARATUS INTEGRATED WITH REAL-TIME HEALTH SUPPORT SYSTEM

TECHNICAL FIELD

The present invention relates to a totally non-invasive and intelligent telemetry apparatus for monitoring continuous blood sugar levels, blood pressure data, psychological stress and other physiological parameters. It is, in particular, related to clinical monitors, health management gadgets and wearable medical devices involving reflective optical sensing design.

BACKGROUND OF THE INVENTION

Modern lifestyle and food habits have huge impact on our physiological and psychological health. In this fast-paced society, it has become a necessity to track and manage our health and activities. In fact, globally 1 in 11 of us are suffering from diabetic condition and 21% of people in the US are standing on the diabetic border. In the coming quarter century, this count is expected to raise by more than 200 million and the prevalence is expected to raise by over 25%. The current technology either offers painful periodic invasive monitoring solution or disposable microneedles based monitoring solution. The current continuous glucose tracking devices also fails to monitor blood sugar levels in prediabetic range and neither acts as a management or prevention solution. Attempts have been made in the past by inventors and academic scholars to create a non-invasive technology, but their hardware and processing architecture proposals ignores underlying scientific principles of reflective sensing and real-time processing techniques.

The invention is hence directed towards a hardware design and real-time processing system that can intelligently overcome the barriers using boundary angle conditions and other signal altering factors like dispersion effects. The disclosure describes a reflective sensing based portable continuous blood sugar monitoring apparatus integrated with real-time diet recommendation and lifestyle management system, which can work for both prediabetic and diabetic population. The device also includes other health guidance components like blood pressure fluctuation tracking system, hypertension management system, sleep monitoring system and emergency life-support system.

What is needed is:
1. Reflective sensing based accurate continuous blood sugar monitoring apparatus that can work for every segment of the population;
2. An intelligent blood sugar management solution that can act as an effective medical and well-being guidance system; and
3. An integrated general wellness solution for managing other physiological conditions such as hypertension and emotional stress.

SUMMARY OF THE INVENTION

The object of the invention is to present a reflective configuration based totally non-invasive continuous blood glucose monitoring solution. The apparatus can also be utilized to monitor and manage blood pressure and other health parameters.

First Aspect

In the first aspect, a reflective configuration based near-infrared optical spectrometer is presented. The Near-Infrared (Near-IR) spectrometer comprises of a set of Near-Infrared LEDs and optical lens tilted at boundary angle $\theta_B$. A distance of wavelength number ($k\lambda$) is kept between the light sources for attaining constructive interference. The tilt of the signal probe system assures that the Near-IR response is reflected from the bone boundary, which would not otherwise occur in normal direction. The optical lens focuses and constructively interferes Near-IR radiation on the sensing spot. The reflected optical response is captured and focused by an optical lens at the photodetector-end. The reflected response is recorded by the Near-IR photodetector.

Second Aspect

The second aspect of the invention presents a green optical spectrometer. The green spectrometer comprises of a green LED and optical signal probe tilted at a critical angle ($\theta c$), and photodetection system of optical lens and green photodetector. The optical lens and green photodetector are placed at an optimal response receiving spot so that the internal reflection noise can be avoided. The light emitted by tilted green LED is reflected off the skin boundary and the reflected response is captured by the optical lens and green photodetector set.

Third Aspect

The third aspect of the invention shows a red indicator spectrometer. A set of two red photodetectors are placed on the either side of the red LED with optical lens at proximity and distant positions. The signal difference between the proximity photodetectors and distant photodetectors are taken to analyse the red signal dispersion values. The dispersion values are analysed through the internal circuitry of the telemetry apparatus.

Fourth Aspect

The fourth aspect of the invention provides an infrared indicator spectrometer. A set of two infrared photodetectors are placed on the either side of the infrared LED with optical lens at proximity and distant positions. The signal difference between the proximity photodetectors and distant photodetectors are taken to analyse the infrared signal dispersion values. The dispersion values are analysed through the internal circuitry of the telemetry apparatus.

Fifth Aspect

In the fifth aspect of the invention, a dual side sensing Near-Infrared spectrometer is presented. A primary lens is used to focus the Near-IR response from the set of Near-IR LEDs arranged at distance of wavelength number ($k\lambda$). The Near-IR response is focused at an angle by the primary optical lens on the tilted beam splitter. The beam splitter refracts the radiation on one side and reflects the radiation on the other side. The light refracted by the beam splitter is focused and concentrated by a secondary optical lens tilted at a boundary angle $\theta_G$. The light reflected by the beam splitter is further reflected and focused by a mirror to compensate the phase change. The mirror inverts the phase and focuses the light on the secondary lens on the other side tilted at the boundary angle $\theta_G$. The light reflected from the bone boundary on the either side and the reflected response is captured by the corresponding optical lens on the photodetector end. The optical lens in turn focuses the light on the respective photodetectors. A set of mirrors, at optimal orientations and positions, can be utilized in the refracted space for equalizing the wave pathlength difference between the light in the refracted and reflected space.

Sixth Aspect

A dispersion analyser apparatus is explained in the sixth aspect of the invention. The dispersion apparatus comprises of signal board with light source and optical lens system tilted at an angle and focused on the central photodetector. The photodetector system of the dispersion analyser apparatus comprises of a central photodetector with optical lens and two adjacent photodetectors with optical lens in each of it. The light emitted by the light probe is focused by the signal probe end optical lens on the central photodetector. The reflected light is captured by the central photodetector's optical lens and the two adjacent optical lenses. The photodetector end lenses focus the reflected response on their respective photodetectors. The signal difference between the central photodetector response and total response of the adjacent photodetectors is taken through the Instrumental Amplifier. The output of the Instrumental Amplifier is analysed to obtain the real-time dispersion information.

Seventh Aspect

The seventh aspect of the invention puts forth a low-powered hardware of the telemetry apparatus.

The hardware comprises of optical signal probes of near-infrared light probes, Green LED, IR LEDs and red LEDs, and photodetector probes of near-infrared photodetector, green photodetector, IR photodetectors and red photodetectors with their respective optical elements. The light emitting signal probes, photodetector probes and their corresponding optical elements are arranged according to the spectrometer configurations. The input to the near-infrared light probes are coherently driven through a tunable BJT/FET based active current amplifier circuit and the set of resistors. A main micro-switch set is utilized to shift the input from the LED frontend to the green LED, red LED, infrared LED and to active current amplifier attached to the Near-IR light probes. The LED frontend comprises of LED driver, LED controller, PWM and clock controller, which tunes and sends the input signal through the main micro-switch set.

A BJT/FET based Darlington pair and small signal current source is attached to the Near-IR photodetector set, which is used to amplify the low powered Near-IR response. The low powered green response signals pass through the optical elements and the green photodetector probes, which are amplified by the Darlington pair and small current source attached to the photodetector. The small current source circuits attached to the photodetectors adds a baseline to the response signals. The red response and IR response, recorded by the red photodetector-optical lens system and IR photodetector-optical lens system, are extracted alternatively by using a switch set. The proximity photodetectors responses are separately summed and processed using an op-amp and stabilizing buffer. The responses of distant photodetectors are amplified, summed and processed through darlington pair, an op-amp based circuit and stabilizing buffer unit. The summed response signals of the proximity photodetectors and distant photodetectors pass through the circuit line of ADC, Ambient Noise cancellation IC and DAC. The responses of red-infrared signals are extracted using two different circuit lines. One response line is utilized to analyse the total Infrared-red response and the other circuit line is utilized to obtain dispersion signal. An Instrumental Amplifier is attached to the proximity and distant photodetectors response output line for extracting the real-time dispersion information. The analysed dispersion signal is passed through a power notch to remove the power line noise. The analysed dispersion signal passes through an ADC to the microprocessor. The distant photodetector signal and proximity photodetector signal are aggregated using resistors and Transimpedance (TIA) amplifier. The response signals of Near-infrared light, green light and red-IR light are processed using the photodetector frontend circuit line of TIA amplifier, power notch, ADC and noise cancellation IC. The processed output response is then sent to the microprocessor. A main micro-switch set is attached between the photodetector frontend and response line of different light spectrum, which shifts the output response to respective photodetector circuit based on the input signals. The micro-switch set reduces the overall component use and power consumption. An additional switch set can be utilized to reduce the count of the power notch and Noise cancellation IC.

A non-contact MEMs/NEMs temperature biosensor, attached to the microprocessor, logs the body temperature response and thermal feedback. An ambient temperature sensor, attached to the microprocessor, records the environment temperature and temperature of the internal electronics system. The 9/6 axis MEMs/NEMs accelerometer of the hardware is utilized as a real-time feedback to remove motion noise from the bio-signal response. A set of wireless antennae of WLAN, BLE, GSM and GPS are either externally attached to the microprocessor or integrated inside the microprocessor. The set of wireless antennae communicates the data between the telemetry apparatus, and the set of external storage and computational devices like accessorial mobile devices, server, etc. The set of wireless antennae along with the accelerometer is used for tracking the real-time location and movement signals like phase, speed, steps taken, etc. The microprocessor is used for communicating commands and feedbacks with the internal electronic components of LED frontend, photodetector frontend, accelerometer, temperature biosensors, ambient temperature sensors, other sensors, wireless antennas, USB module, buttons, potentiometer integrated navigator, fancy LED, touch display and other electronics modules. The function of microprocessors also includes computing and storing the required information. A mini-touch display is attached to the hardware for viewing and accessing the real-time medical information, health data and on-device applications. The touch display is also used to calibrate and operate the instrumentation. The fancy LED flashes for representing different device modes, device status and decorative applications. The buttons and potentiometer integrated navigator are used for operating and calibrating the device. The memory module attached to the microprocessor is utilized for internally storing the information.

Apart from the display unit, the hardware of the telemetry device is internally or externally attached to an additional user interaction system consisting of mic and speaker. The set of user interaction hardware components is utilized by the user for interacting with the medical and health practitioners for clinical and health analysis. The professionals can send and receive the information, as well supervise the user through the user interaction system. The user interaction unit is also used as the means to perceive the recorded and computed information, and to operate the device and its in-built applications.

The hardware of the telemetry apparatus is attached to a power supply unit, which comprises of power management IC, supercapacitor-battery set, supercapacitor-renewable energy harvester set, wireless coil, USB module and negative voltage converter. The power management IC of the power supply unit, attached to the hardware and microprocessor, regulates the current flow and power supply. The negative voltage converter attached to the power management unit generates the negative reference signal. The USB module and supercapacitor-battery are utilized for powering the electronic circuit. The USB module is also used for communicating the data with the external devices and charging the battery of the internal circuit. The device is wirelessly recharged through the coil. The power supply unit includes an alternative and supplementary power supply unit containing renewable energy harvester and supercapacitor.

Eighth Aspect

The eighth aspect of the invention provides the method for device initialization and apparatus calibration. During the initial device start-up, the age, weight, gene info, BMI, Fat % and contact layer picture of the user is recorded. The recorded contact layer skin colour is processed on a scale of 1 to 10 and the contact picture is again recorded multiple times. The median values of the processed contact layer color are stored and utilized. On unavailability of the contact layer recording, the realistic profile picture of the user is processed, and the values are altered by an adjusting parameter to extract the realistic value of the contact layer skin color. Different blood sugar values, blood pressure values and other health parameters are recorded and processed for calibrating the device. The blood sugar values, blood pressure values and other vital health parameters are recorded during sitting position, standing position, relaxing position, fasting glucose, post-dinner, post-breakfast, post-lunch, post-sleep, post-exercise, before dinner, before breakfast, before lunch, before bed-time and also during the hypoglycaemic and hyperglycaemic conditions. If increasing value of hyperglycaemic and hypoglycaemic conditions are recognized, the device is re-calibrated. For diagnosed hyperglycaemic and hypoglycaemic conditions, the apparatus records and stores the blood sugar values, blood pressure values and vital information multiple times a day. If enough calibration values are available, the calibration process is skipped and if lesser number are values are available, then more calibration values are recorded. The Near-IR light sources, green LED, IR LEDs and red LEDs are initiated, and the values of the responses are recorded in their respective matrices. The recorded responses are normalized according to the light source area and power. The green response (G) signals are analyzed for DC losses. The recorded red and IR response signals are analyzed to extract the Integrated signal response (Rtot–IRtot), Differential/Dispersion signal responses (Rdiff–IRdiff) and power response (RP–IRP). The body temperature (Btemp) and Ambient temperature response (Atemp) are recorded and the response signals are adjusted as per the temperature stats. Accelerometer is initiated to record movement data and to remove motion noise in the real-time signal. Wireless antennae are initiated and analysed for location and movement data.

Ninth Aspect

The ninth aspect of the invention presents the real-time system for monitoring continuous blood sugar levels. The recorded sensor signals are processed and correlated for extracting the real-time values. The real-time green sensor values G) are analyzed for losses due to skin layer. Fast Fourier analysis is applied to to detect the skin signal loss green parameter (GPAR). The Near-IR signal values are adjusted for body temperature values and ambient environment temperature values using statistical methods, and the different resonant values of the Near-IR signals are computed. The mean of different adjusted Near-IR values is computed using NIRT= (NIRA+NIRB+NIRC+so on till NIRN)/N. Fast-Fourier series is applied to Rtot1 to derive oscillatory signal (Rosc). The oscillatory signal (Rosc) is adjusted for blood line dc losses, and then it (Rosc) is adjusted for skin losses using the derived green signal parameter (GPAR). The oscillatory signal power (Rosc) is compensated from the Near-IR signal ($|NIRT1|_t = |NIRT|_t -$ $X1.|Rosc|_t$). Then, NIRTI is adjusted from the IRtot and IRdis for Near-IR dispersion due to other blood particles (NIRT2=NIRT1-X1IRdis-X2.IRtot). Then Near-IR value is adjusted for red differential/dispersion signal (NIR3=NIR2+ X3.Rdif). Then, the green parameter is adjusted from Near-IR signal in variable constant form and dependent coefficient form (NIR4-NIR3-X4.In (GPAR-X5)). Linear and non-linear correlation is applied to different processed Near-IR values (NIR4), Color indices (C) and different recorded blood sugar calibration values. Then, the Near-IR sensor is calibrated using the processed Near-IR signal and calibrated blood sugar values. Then, real time value of continuous blood sugar (BSL) is computed from the calibrated sensors. The sensor is re-calibrated for recognized hyperglycemic and hypoglycemic conditions. The IR sensor, red sensor, current values and calibrated values are analyzed and learnt for tracking BSL, hypoglycemic and hyperglycemic conditions. The real-time values of the continuous blood sugar and blood sugar fluctuation data are stored and displayed. On recognizing the chronic and abnormal blood sugar conditions, the system automatically alerts the life-support network of the user.

Tenth Aspect

In the tenth aspect of the invention, a method to precisely calibrate the blood sugar monitoring is provided. Initially the computed blood sugar values are evaluated for boundary values and threshold fluctuation values. Different blood glucose states of fasting glucose, pre-meal values and post-meal values are evaluated against the boundary fluctuations, threshold values and different blood sugar ranges, and the device is recalibrated accordingly. Based on the detected blood sugar condition of pre-diabetes, hyperglycemia and hypoglycemia, an automated therapy and diet recommendation is presented to the user. The dispersion values are further analyzed and learnt to evaluate the response result.

Eleventh Aspect

A method to extract the blood pressure and stress levels are provided in the eleventh aspect of the invention. Initially, the red signals are compensated for skin losses using parametric analysis between the green response and red response signals. Fast Fourier analysis is applied to the total and oscillatory signals of the red sensor to extract the power values of the red signal. The analyzed and noise-free red sensor values are further analyzed using non-linear or linear analysis for deducing real-time blood pressure values. The real-time blood pressure values and fluctuations are analyzed to evaluate the blood pressure conditions of stage 1 hypertension, stage 2 hypertension, pre-hypertension and low blood pressure conditions. Based on the recognized blood pressure condition, the user is presented with physician consultation message, diet and health management techniques. The blood pressure values and the temporal fluctuations of the red signal are analyzed through different methods and parameters of user location, user state and user postures. The analyzed blood pressure values and the temporal fluctuations are utilized to evaluate the psychological stress levels of the user. During the state of psychological stress, the user is automatically presented with stress management methods. On recognizing the severe blood pressure condition and state of psychological stress, the system automatically alerts the life-support network of the user.

Twelfth Aspect

An automated sleep tracking system is presented in the twelfth aspect of the invention.

The accelerometer signals, body temperature, blood pressure data and blood sugar values are initially evaluated for state of sleep. The variations in blood pressure and blood sugar values are compared against the wake levels, and then derived HP1, HP2 and HP3 parameters are furthered analyzed for recognizing NREM sleep cycle and REM sleep cycle. The computed sleep cycle and time period of the respective sleep cycles are incremented and stored. The actimeter signals are evaluated to verify if the user's sleep is disrupted. On recognizing the state of disturbed sleep, the health and life-style recommendations are provided to the user. Further learning is applied to the signals to simplify the sleep recognition process.

Thirteenth Aspect

The thirteenth aspect provides a method and software device to calibrate the device. The user data of profile picture, age, BMI, fat %, gene info, weight and height are recorded through the telemetry apparatus or the accessorial mobile apparatus. A picture of the contact surface is recorded and processed through the aforementioned method. The blood sugar and blood pressure calibration values are recorded for different instances of fasting glucose values, before bedtime, before lunch, before dinner, after breakfast, after sleep, after dinner, after lunch, and after exercise. The user can also record information on the micro-nutrition and macro nutrition, and meal-information through the telemetry apparatus or the accessorial mobile apparatus. The real-time information and data trends on blood sugar levels, blood pressure levels, neural activity, pulse rate, oxygen saturation and body temperature are automatically displayed on the device along with health sense message. The device comprises of automated real-time reminder and alert system to notify the user during the instances of medication and chronic medical conditions. The device further comprises of recommendation system, which guides the user with health practices and diet management techniques for the diagnosed health condition.

Fourteenth Aspect

The fourteenth aspect provides an optimization method for estimating the health and calibration parameters from the previously recorded data of the user database. The color index, age, BMI, fat %, gene Info, sensor intensity, signal response and real-time calibration values of the user are matched with the previously recorded parameters in the database. The optimization parameters of color index, sensor calibration data, healthy H.R. index, performance index and progress index are learnt and derived from the central database. The optimization parameters are returned to the user device, which is used in processing the real-time biological information and other health parameters.

Fifteenth Aspect

In the fifteenth aspect, a parallel computational network is provided. The parallel computational network enables the computation with much higher speed and efficiency, while keeping the complexity low. The network of parallel computation network comprises of internal microprocessor, external server computers, accessorial mobiles devices, external computers and other connected local devices. The external servers are used for executing computational process, and as well as for remotely storing the information. The accessorial mobile devices and other synchronized devices are also used to compute and store the information. The network of parallel computing devices are accessed through wireless methods of 'WLAN, BLE, GSM' and through other possible modes of communication. Whenever necessary, stored information and computed results are communicated between the telemetry apparatus and network of devices.

Sixteenth Aspect

An emergency system is presented in the sixteenth aspect. On recognizing emergency trigger, the system validates the status of the wireless antennae and switches it on. The location data are recorded through the wireless antennae set, and the biometric and other vital information are recorded through the internal bio-sensors. The recorded information is transmitted to the central server, SOS network, support network and to the near—by mobile devices through the wireless methods. The devices are synchronized, and the next set data are transmitted. The wireless data transfer occurs directly or via medium of central server.

Seventeenth Aspect

The seventeenth aspect of the invention provides a smart wearable or portable embodiment of the reflective continuous glucose monitor. The near-infrared optical spectrometer, reflective red sensor spectrometer, reflective Infrared sensor spectrometer, green optical sensor spectrometer and body temperature sensor are placed inside cavity structure of the contact surface. The cavity like structure is utilized as a means to evade the background optical noise. The sensors on the contact surface are surrounded by a foam base, which curtails the movement noise in the real-time recording. The device is packaged with a board of successive segregated layers of analog and sensor frontend plane, secondary digital and analog plane, power plane and digital and wireless plane. The mini-touch screen, mic and micro-speakers are placed on the top user facing surface. The successive and sequential plane packaging method is used to curtail the electrical noise and reduce the circuit line tracing efforts. The battery is placed in unobtrusive manner around the electronics packaging to elude the signal interference. The device is covered with the PCB waterproofing coating and product waterproofing coating. A USB charging and data transfer port and button set is packaged on the side surface of the device along with buttons. A button and navigator crown is packaged on the other side surface of the device.

Eighteenth Aspect

The eighteenth aspect of the invention presents a solar module powered portable telemetry monitoring embodiment form. A reflective sensing spectrometer with foam base is embedded on the finger placement area of the apparatus. A set of buttons are embedded on the side surface of the device, which are used to operate the device. A USB port is attached on the side surface of the device, which is used to transfer data, and to power the device and its battery. The device comprises of touch-screen, which is used to access the information and to operate the telemetry apparatus. The back surface of the device is attached to a solar module. The solar module has an actuatable module 1 and actuatable module 2, which are attached to each through an actuatable hinge. The actuator hinge along with an actuator automatically extends the solar module for absorbing more solar energy. The solar module is used as an auxiliary renewable powering unit. The device further comprises a wearable chord with molded extender clip and extender chord, which is used as a method to modify the chord size. The device is further coated with water proof coating.

Nineteenth Aspect

In the nineteenth aspect of the invention, an earphone based embodiment form is presented. The device has reflective sensing spectrometer near earlobe attachment area. A fancy LED is embedded in the ear hook of the device, which emits light to represent different operating modes and device status. The music ear-buds are attached to the rear-end of the device. The ear-bud and ear-hook are used to fasten the device to the user.

Twentieth Aspect

The twentieth aspect of the invention presents a fancy LED apparatus. The fancy LED device comprises of multi-colored LED encased in a line of multiple optical tubes. The light emitted by the fancy LED is observed inside the multiple optical tubes.

BRIEF DESCRIPTION OF THE ARTWORK

Figure 13:
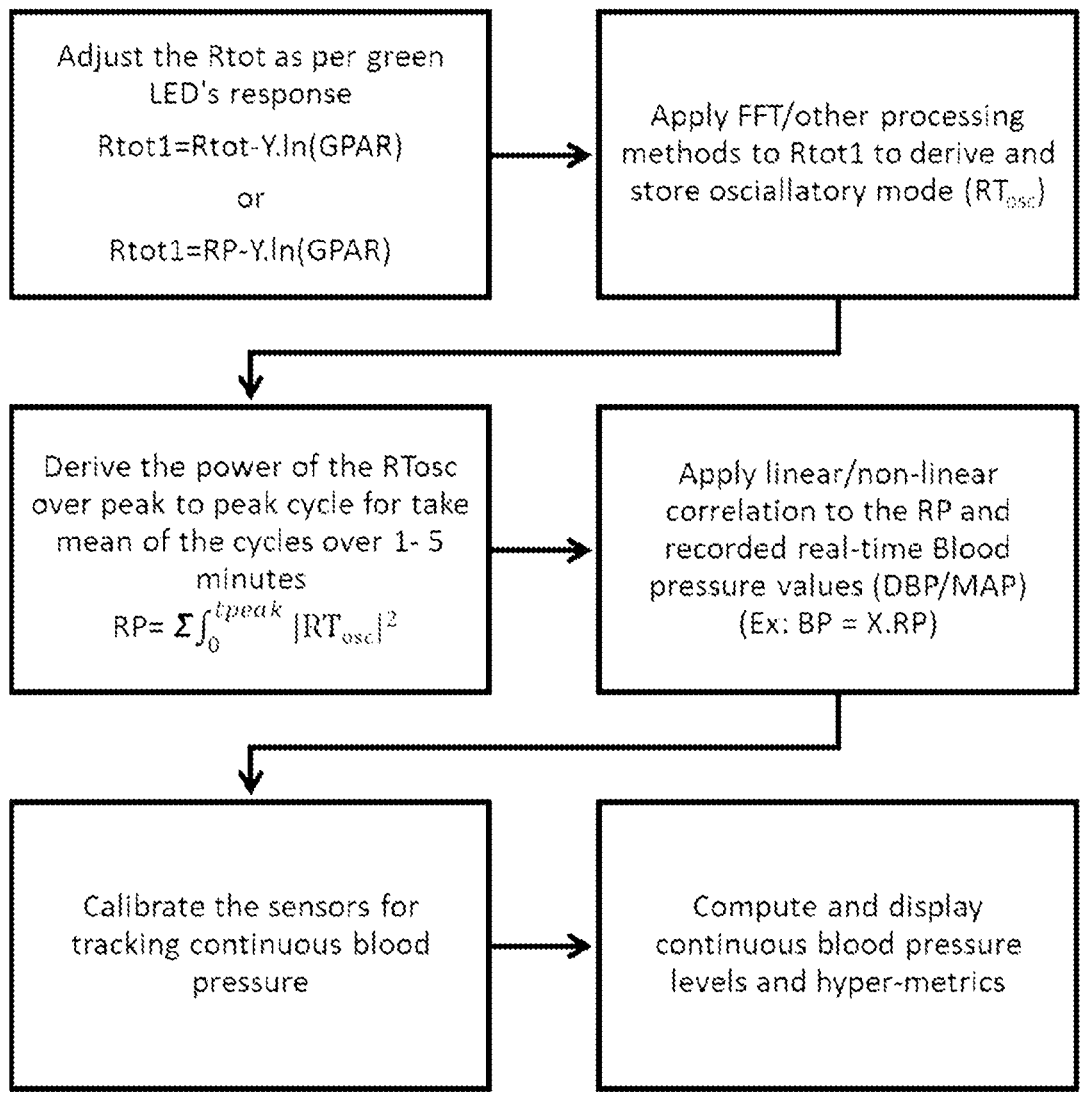
Figure 15:
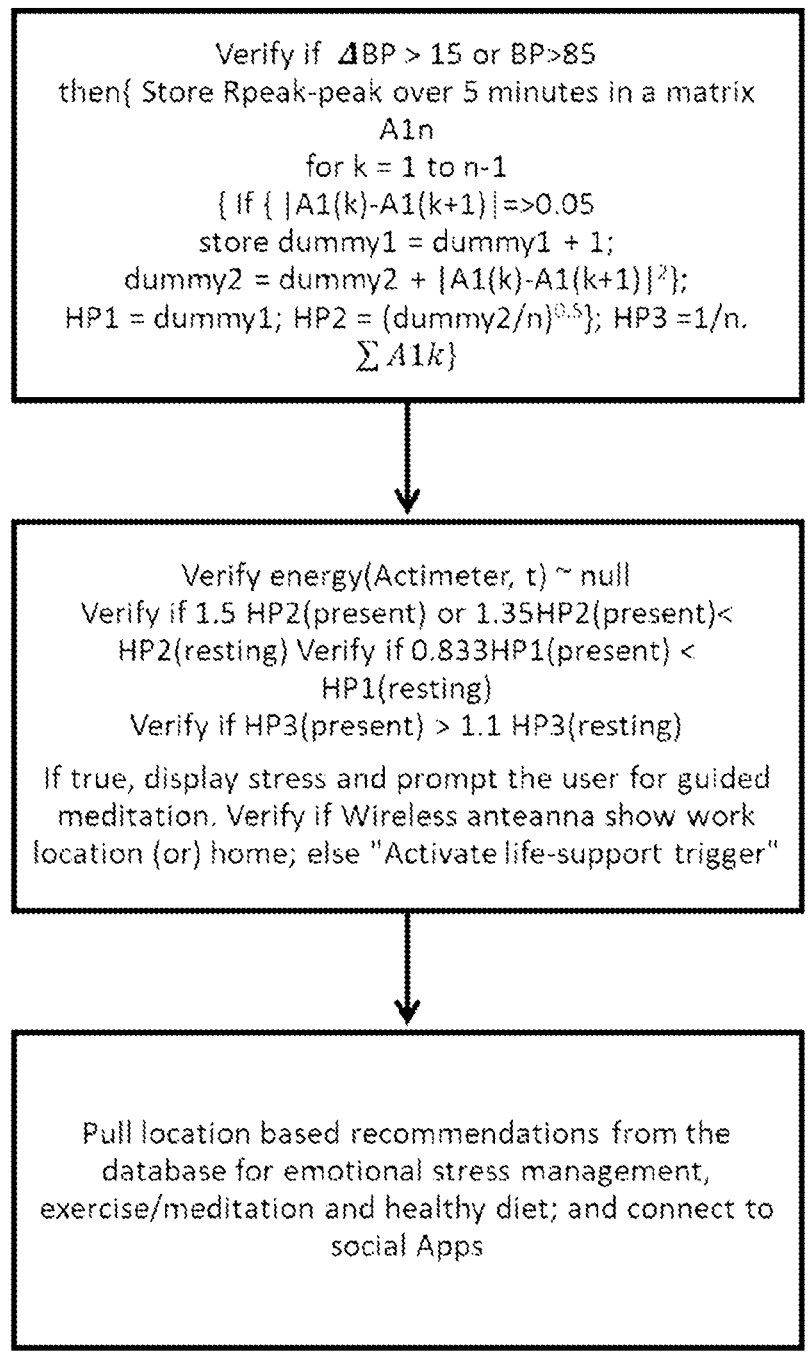
Figure 16:
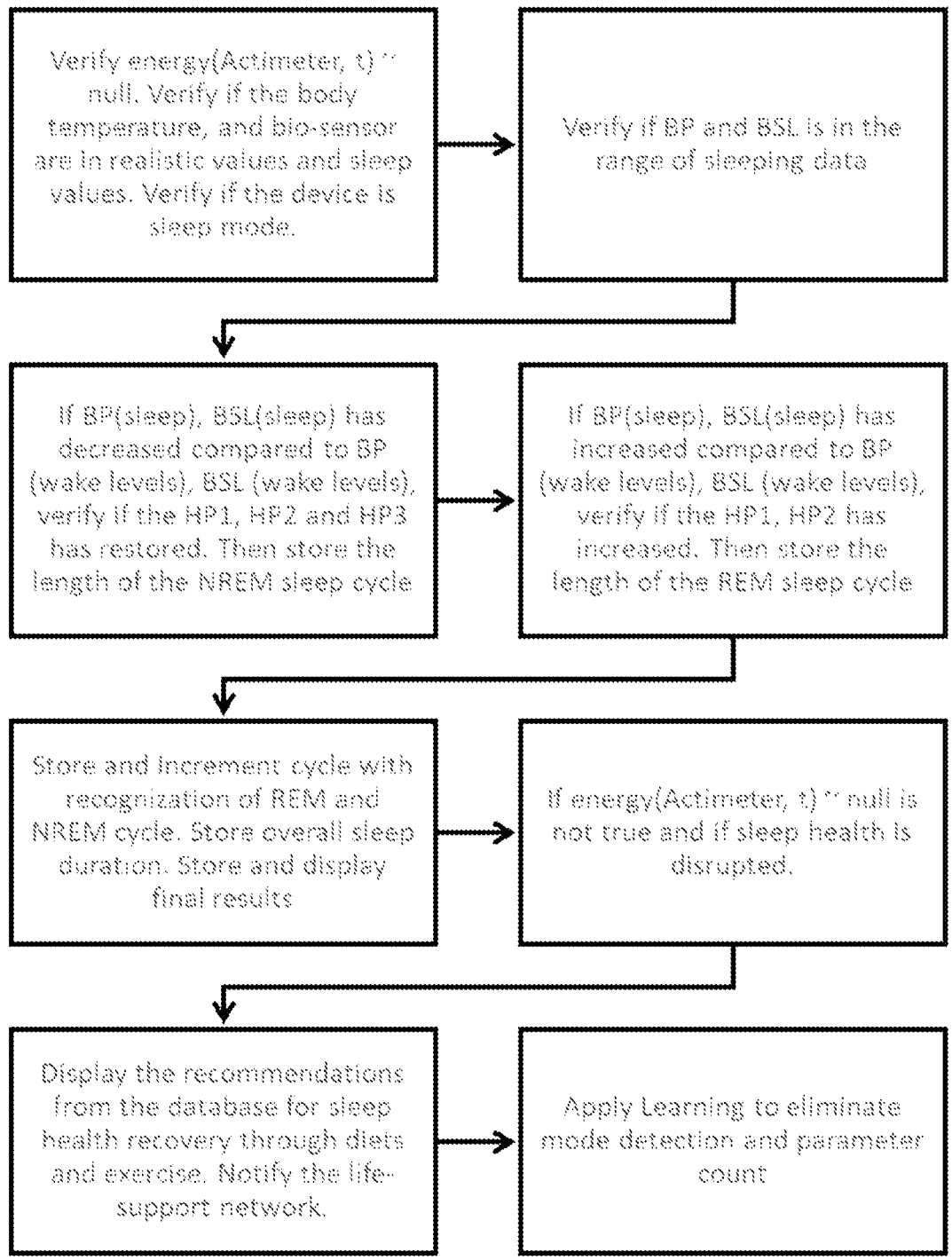
Figure 17:
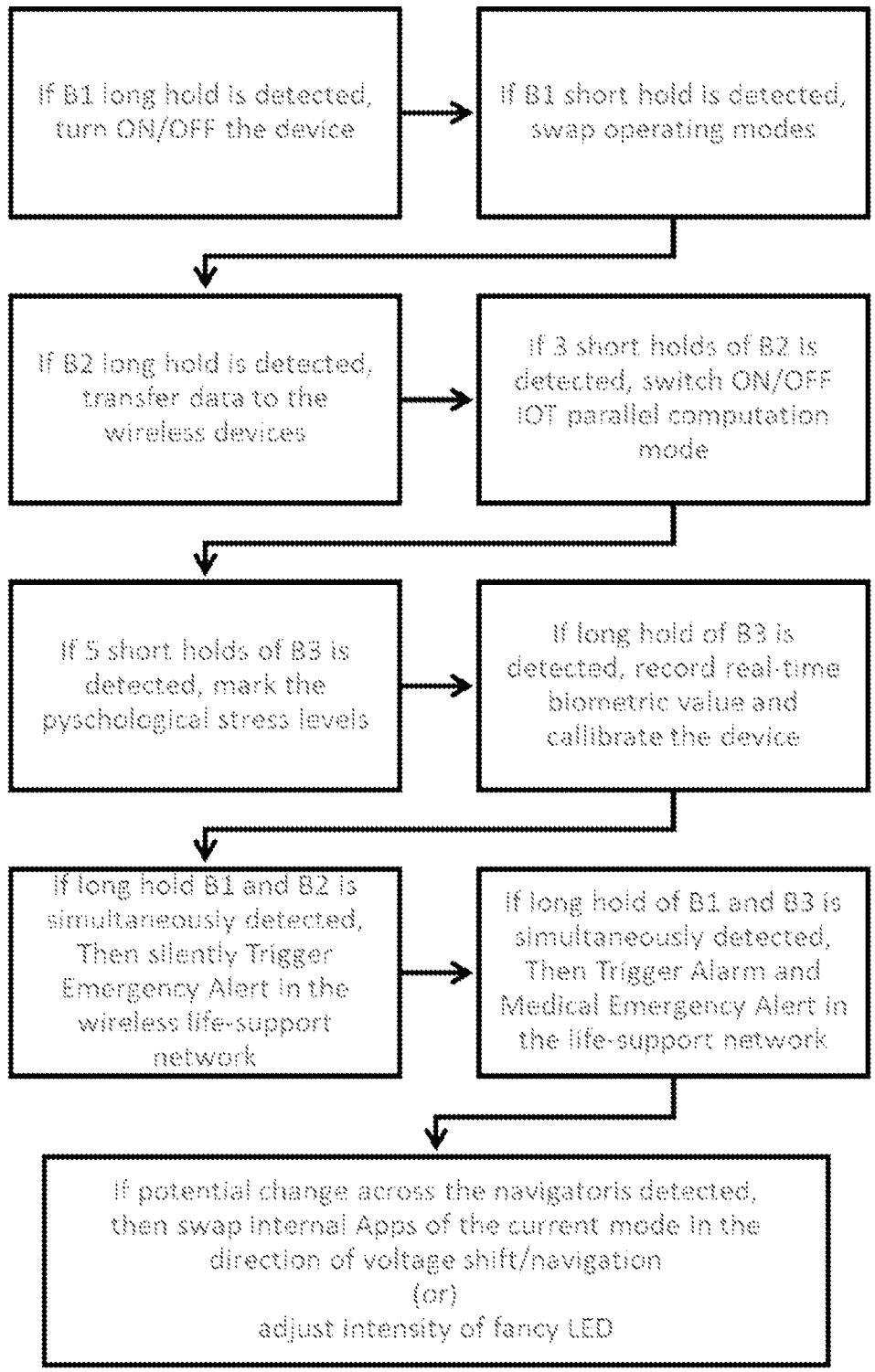
Figure 18:
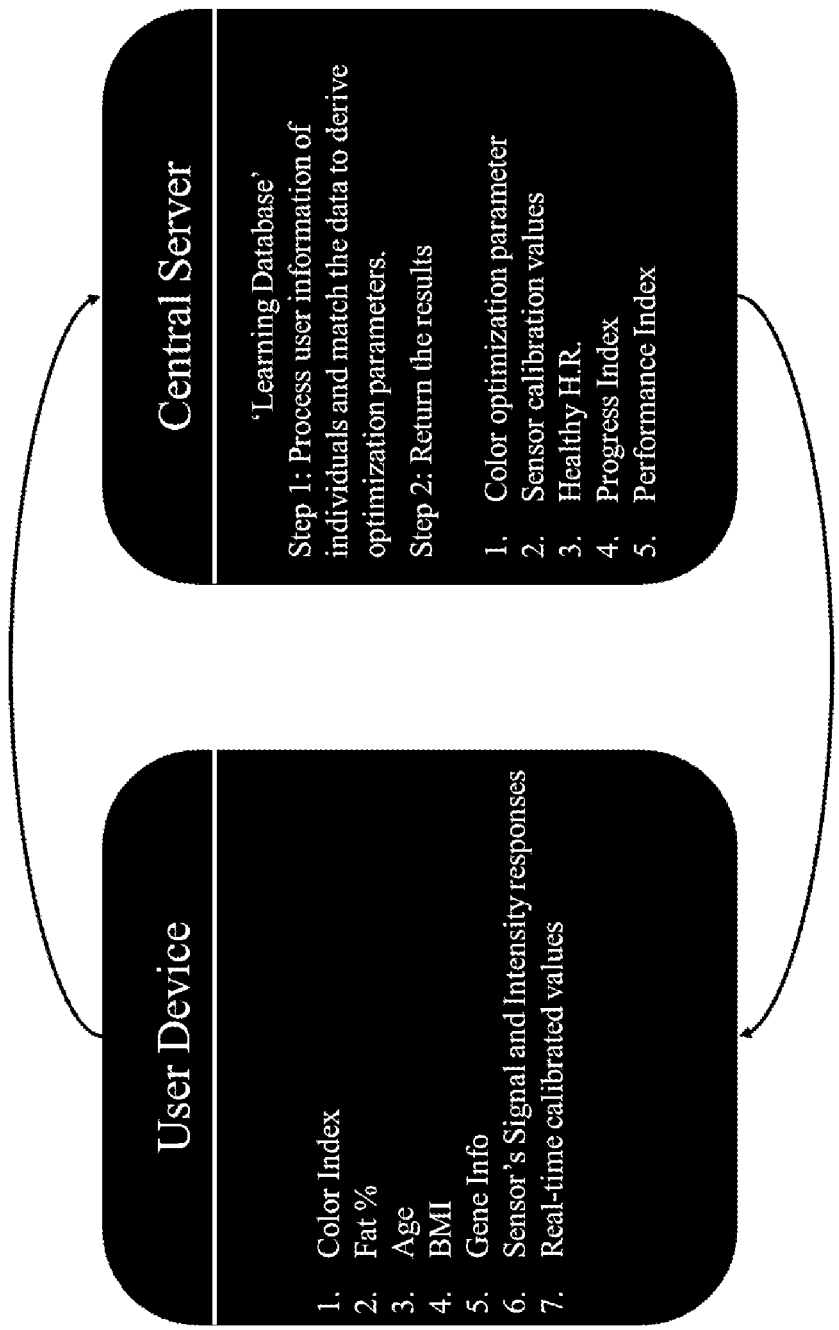
Figure 19:
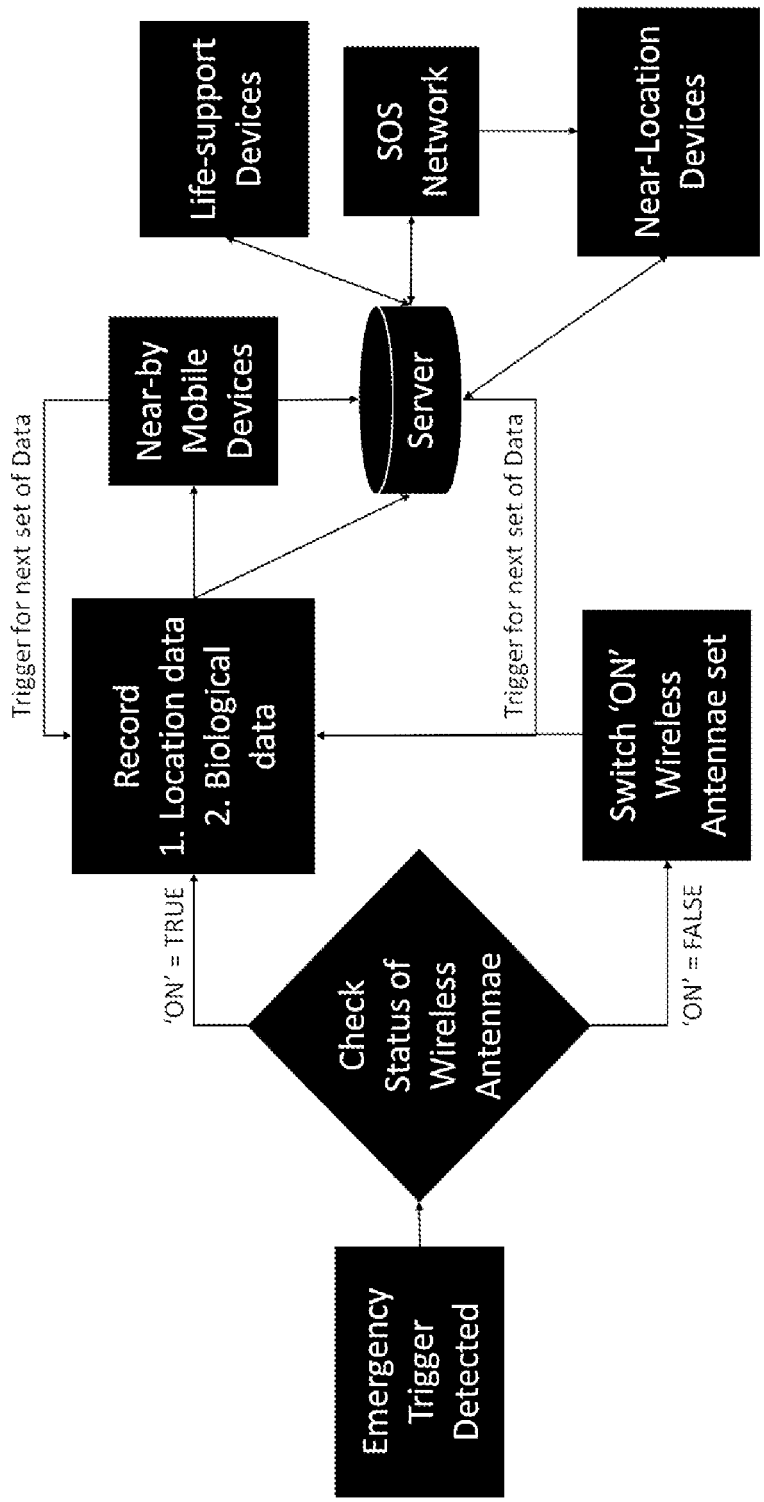
Figure 20:
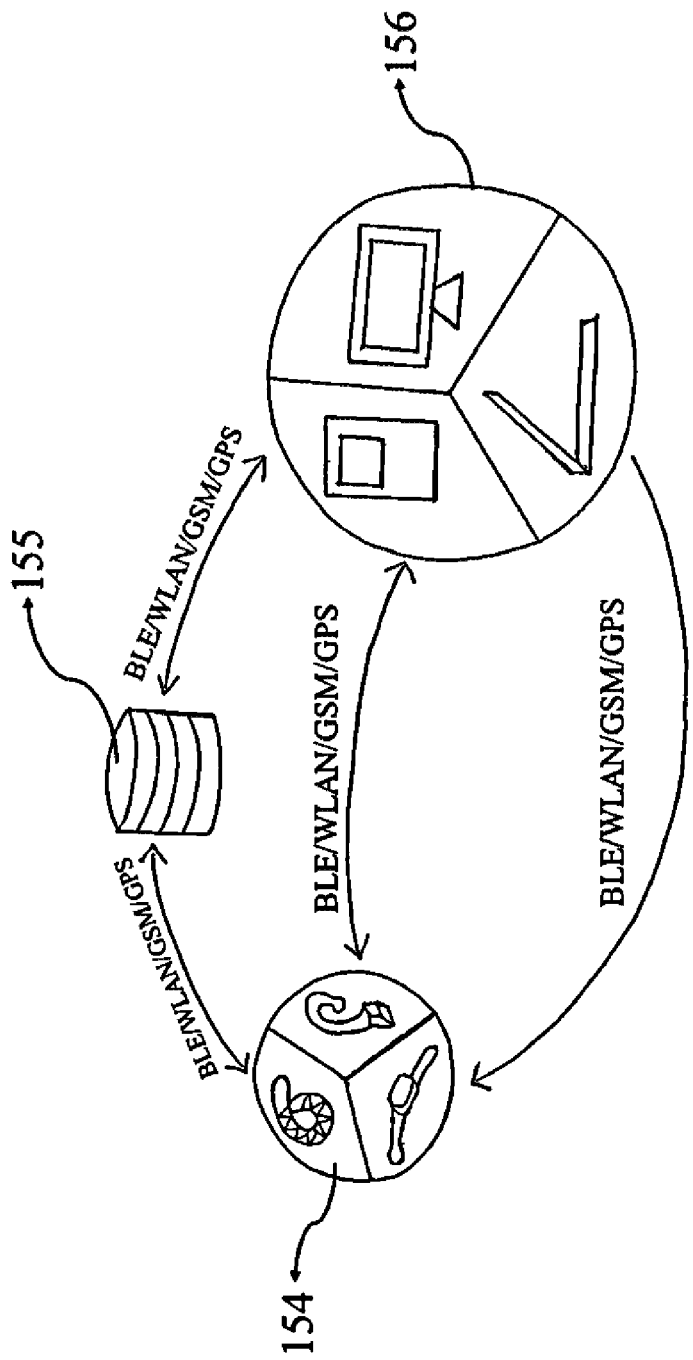
Figure 21:
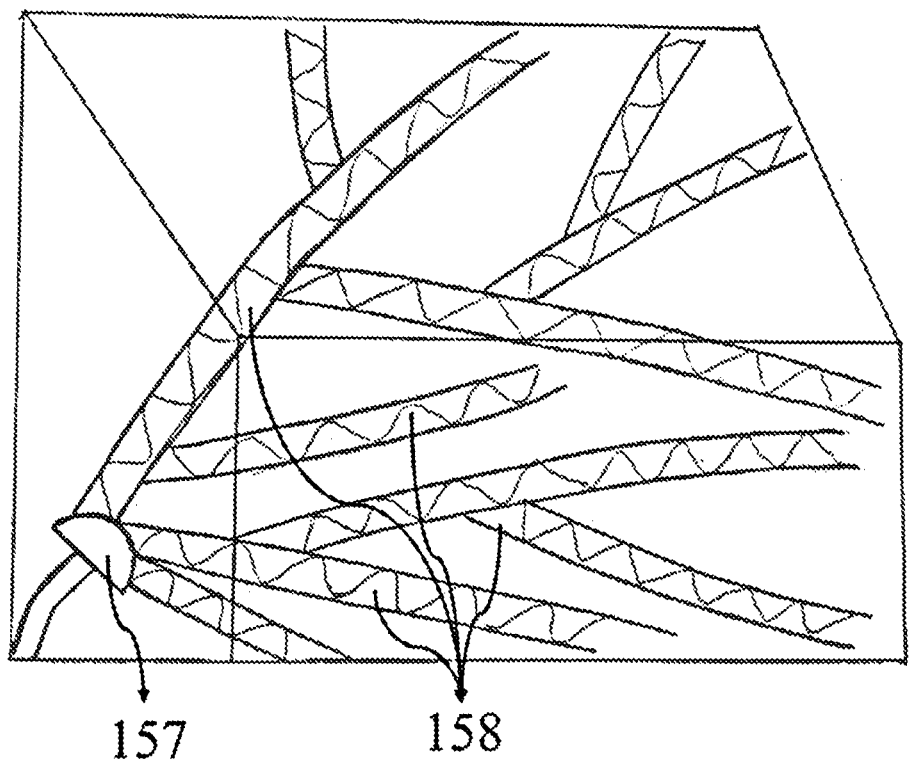

Series of FIG. 9 show the method to calibrate the telemetry apparatus;

Series of FIG. 10 show the processing method for initialization and normalization;

Series of FIG. 11 is the real-time system for monitoring the continuous blood sugar levels;

Series of FIG. 12 is the method of blood sugar analysis for recognizing the hypoglycaemia, hyperglycaemia and unusual blood sugar fluctuations;

FIG. 13 is the real-time system for monitoring continuous blood pressure levels;

Series of FIG. 14 is the method of blood pressure analysis for recognizing the hypertension, hypotension, and unusual blood pressure fluctuations;

FIG. 15 is the automated real-time system for monitoring emotional stress levels;

FIG. 16 is the real-time and automated sleep tracking system;

FIG. 17 shows a program for operating the telemetry apparatus using the buttons and navigator;

FIG. 18 is a learning method for estimating processing parameters from the user database;

FIG. 19 is the design of automated emergency response system;

FIG. 20 shows the network of devices based parallel computational and storage method;

FIG. 21 is the design of fancy LED apparatus;

Series of FIG. 22 show automated interface for recording user information and calibration values;

FIG. 23 is the automated interface for recording and accessing detailed diet information;

Series of FIG. 24 show the automated interface for accessing real-time biological information;

Series of FIG. 25 show the interface of the automated real-time alerting system;

Series of FIG. 26 show the real-time medication reminders;

Series of FIG. 27 show the sample interface of the automated recommendation system;

Series of FIG. 28 is the smart tracker embodiment form of the telemetry apparatus;

Series of FIG. 29 is the solar powered handheld monitoring embodiment form; and

Figure 30:
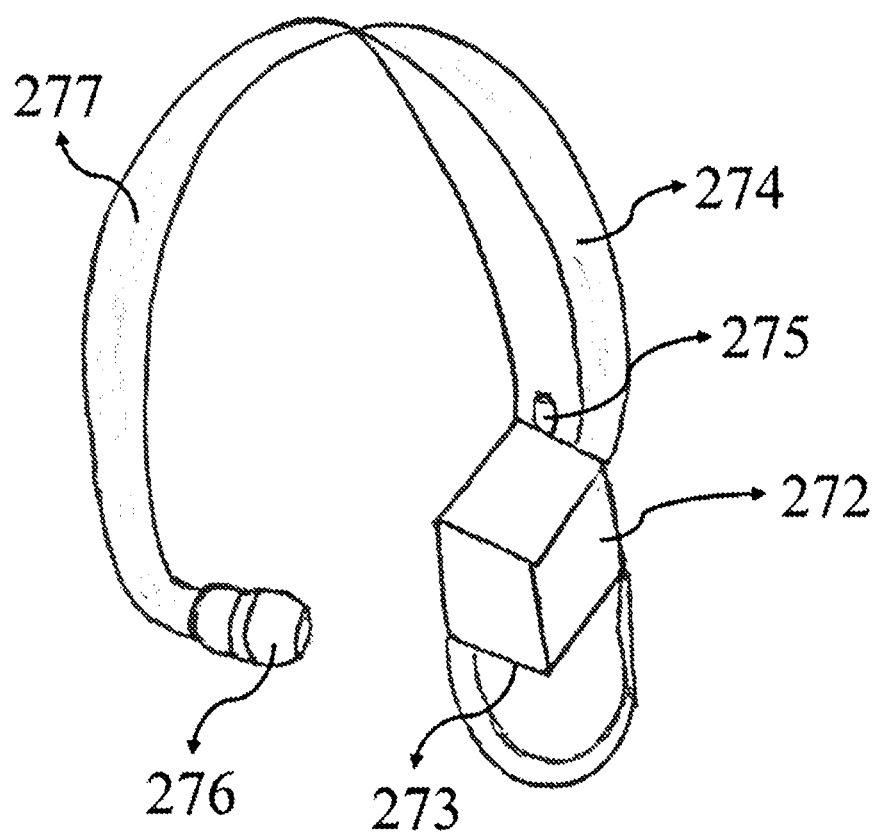

FIG. 30 is the ear attachment embodiment form of the telemetry apparatus.

DETAILED DESCRIPTION OF THE INVENTION

Comprehensively, the disclosure can be utilized and perceived in the form of various applications. The principle of the described invention is not intended to limit to the specific device or instrumentation application. The disclosure can be chiefly classified into live clinical diagnostic instrument, telemetry medical apparatus, mobile wellness management device, automated recommendation system, real-time intelligent medical reminder, software medical device and other forms of health management devices.

Figure 1:
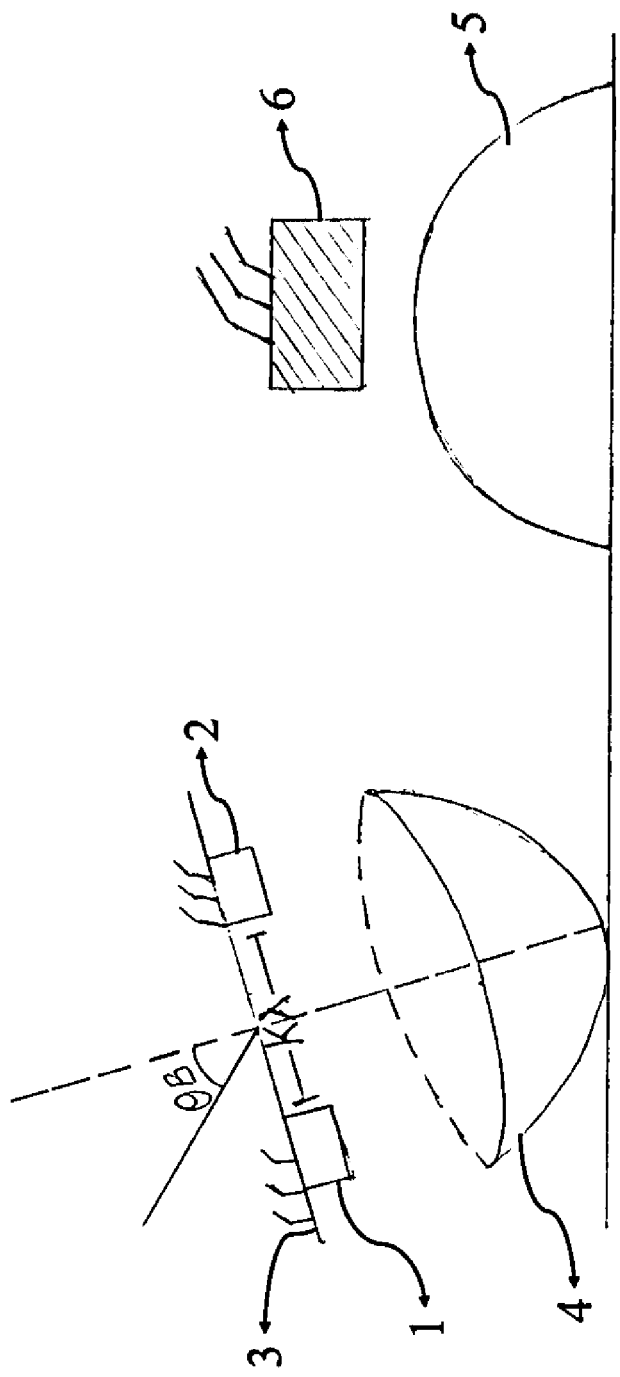
FIG. 1 is the reflective near-infrared optical spectrometer apparatus.

FIG. 1 is the reflective near-infrared spectrometer apparatus. The near-infrared light sources 1 and 2 are embedded on the LD board 3 at a quantum distance of $k\lambda$, which are tilted at a boundary angle of $\theta_B$ (where k is the constructive interference reference number). The light emitted by the 1 and 2 are focused by the near-infrared optical lens system 4 placed on the contact surface and tilted at the boundary angle of $\theta_B$. The quantum distance of wavelength number is maintained between the LDs and the light source objects to obtain a constructive interference (i.e. the distance can vary depending on the relative angle and path length between the light sources or any coherent sources such as slits). The near-infrared light sources 1-2 and optical lens system 4 are tilted at the angle of $\theta_B$ to inject the input signal at the glazing boundary angle on the sensing spot. Bone generally tends to absorb the near-infrared radiation; hence the glazing critical angle phenomenon is utilized to make the light bounce back from the bone boundary. The photodetector-end near-infrared lens system 5 is placed at an optimal distance from the signal probes of 1-2-4 for eluding the internal reflection noises and for capturing the near-infrared reflected response. The reflected response is focused by the optical lens system 5 on the near-infrared photodetector 6, which records the real-time response.

Figure 2:
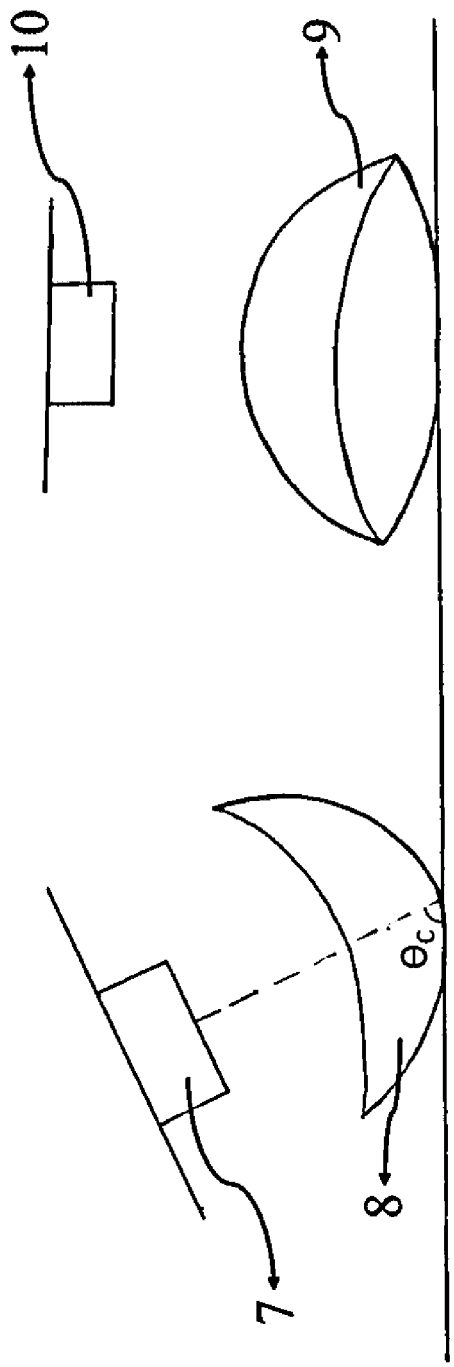
FIG. 2 is the reflective green optical spectrometer apparatus.

FIG. 2 is the design of the reflective green spectrometer. The green LED signal probe 7 and green optical lens 8 placed on the contact surface are tilted at a critical angle of $\theta_c$. The light is injected at the critical angle of $\theta_c$, so that light reflects off the skin boundary. A photodetector-end optical lens system 9 is placed an optimal response distance to capture the internal-reflection free reflected response. The light concentrated by the optical lens system 9 is recorded by the green photodetector 10.

Figure 3:
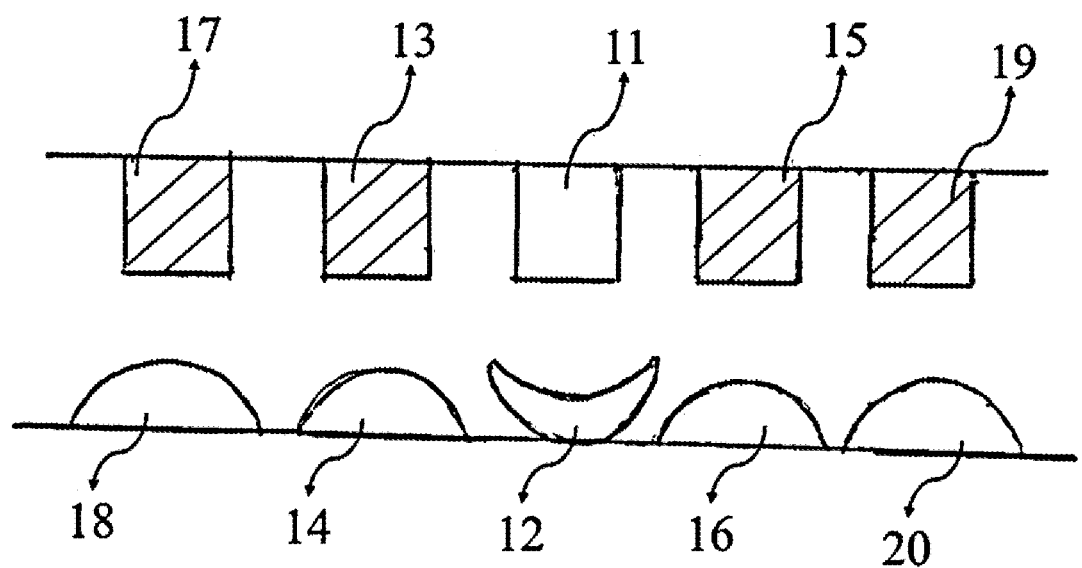
FIG. 3 is the reflective red optical spectrometer apparatus.

FIG. 3 shows the red indicator apparatus for recording the reflective dispersive signals. The light emitted by the red LED 11 is focused on the sensing spot by the red optical lens system 12. A red photodetector 13 and red optical lens 14 set are placed at an internal-reflection free proximity position from the signal probes 11-12. A red photodetector 15 and red optical lens 16 set are placed on the other side of the signal probes 11-12 at a noise free proximity position. A red photodetector-red optical lens system 17-18 set are placed at the distant position from the signal probes 11-12. The red optical lens-red photodetector 20-19 set are placed on the other side at the optimal distant position. The output response recorded by the set of proximity photodetection probes of 13-14 and 15-16 and the set of distant photodetection probes of 17-18 and 19-20 are analysed to obtain real-time information on the dispersive and non-dispersive signals. The real-time information is utilized to evaluate the medical data, psychological health and dispersion of the red light due to the blood particles.

Figure 4:
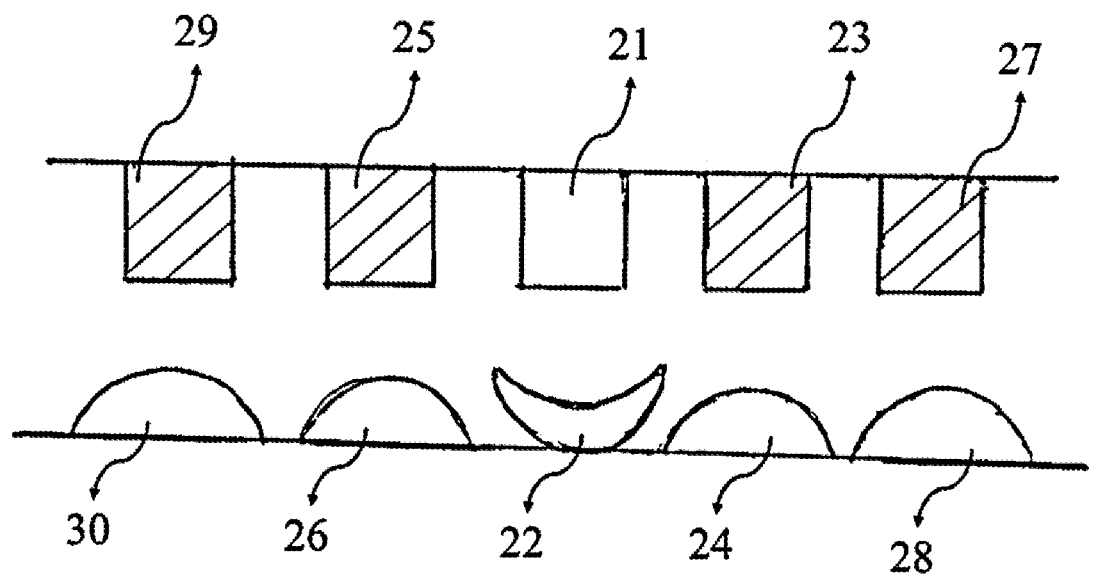
FIG. 4 is the reflective infrared optical spectrometer apparatus.

FIG. 4 shows the infrared indicator apparatus for recording the reflective dispersive signals. The light emitted by the infrared LED 21 is focused on the sensing spot by the infrared optical lens system 22. An infrared photodetector 23 and infrared optical lens 24 set are placed at an internal-reflection free proximity position from the signal probes 21-22. An infrared photodetector 25 and infrared optical lens 26 set are placed on the other side of the signal probes 21-22 at a noise free proximity position. An infrared photodetector-infrared optical lens system 27-28 set are placed at the distant position from the signal probes 21-22. The infrared optical lens-infrared photodetector 30-29 set are placed on the other side at the optimal distant position. The output response recorded by the set of proximity photodetection probes of 25-26 and 23-24 and the set of distant photodetection probes of 27-28 and 29-30 are analysed to obtain real-time information on the dispersive and non-dispersive signals. The real-time information is utilized to evaluate the medical data, psychological health and dispersion of the infrared light due to the blood particles. Similarly, light sources of different spectrum can be utilized for evaluating the real-time biological information and spectral dispersion data.

Figure 5:
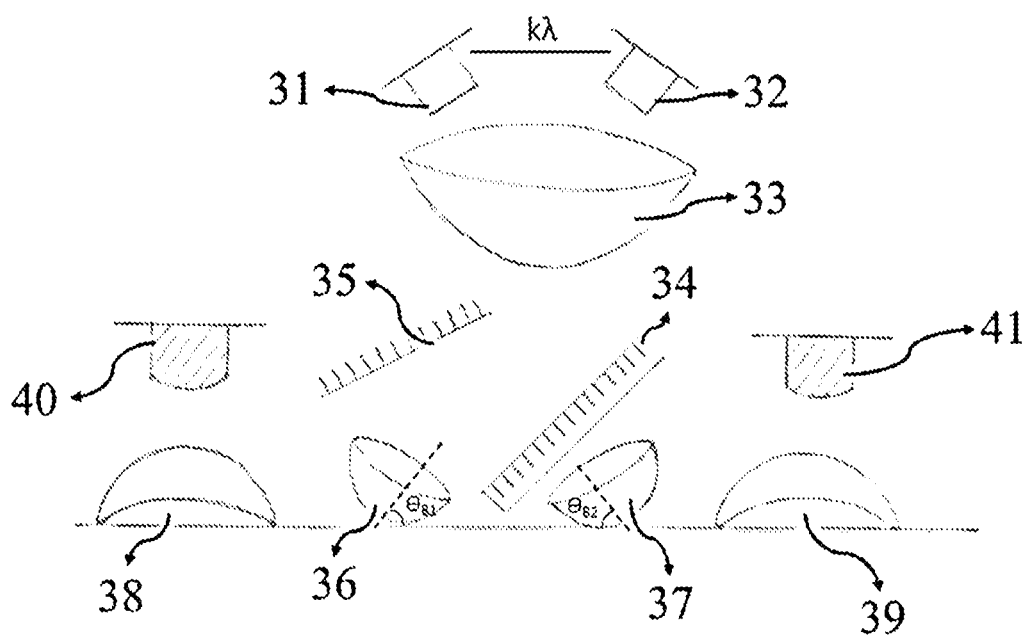
FIG. 5 is the dual-side sensing near-infrared spectrometer apparatus.

FIG. 5 shows the dual side sensing near-infrared apparatus. The near-infrared light sources of 31 and 32 are placed with k2 distance between them. The radiation emitted by 31-32 is constructively focused by a primary near-infrared optical lens system 33 on the mini beam-splitter 34. The beam splitter 34 splits the incoming radiation into the reflected and refracted space. A mini mirror 35 in the reflected space inverts the phase of the reflected radiation and focuses the light on the secondary near-infrared lens system 36. The secondary near-infrared lens 36 is tilted at an angle of $\theta_{B1}$ and placed on the contact surface to inject the light at the glazing angle on the sensing spot. The light refracted by 34 is focused by a secondary near-infrared optical lens system 37, which is placed on the other side of the contact surface. The near-infrared optical lens 37 is tilted at an angle of $\theta_{B2}$ for injecting the refracted at the glazing angle. The near-infrared optical lenses of 38 and 39 in the reflected space and refracted space are placed at an optimal noise-free distance for focusing the reflected near-infrared response on their corresponding near-infrared photodetectors of 40 and 41. The dual side configuration is utilized to recognize the uncertainty in the output response due to the changes in optical components with time and varying the physiological parameters.

Figure 6:
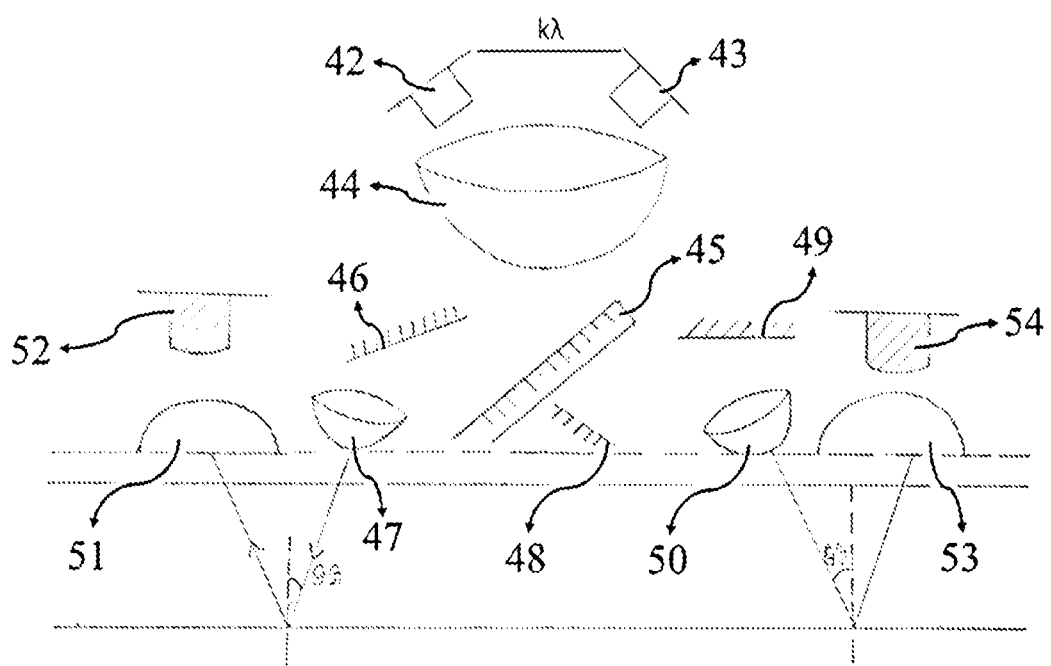
FIG. 6 is the design of pathlength adjusted dual-side sensing near-infrared spectrometer apparatus.

FIG. 6 shows the dual side sensing near-infrared apparatus with an additional pathlength adjusting mirror set. The near-infrared light sources of 42 and 43 are placed with la distance between each other. The radiation emitted by 42-43 is constructively focused by a primary near-infrared optical lens system 44 on the mini beam-splitter 45. The beam splitter 45 splits the incoming radiation into the reflected and refracted space. A mini mirror 46 in the reflected space inverts the phase of the reflected radiation and focuses the light on the secondary near-infrared lens system 47. The secondary near-infrared lens 47 is placed on the contact surface and tilted at an angle of $\theta_G$ to inject the light at the glazing angle on the sensing spot. A set of two mirrors 48-49 are placed in optimal orientations and positions in the refracted space to reflect the refracted radiation and focus the radiation on the secondary near-infrared lens 50. The near-infrared optical lens 50 is placed on the other side of the contact surface and tilted at an angle of $\theta_G$ for injecting the refracted at the glazing angle. The near-infrared optical lenses of 51 and 53 in the reflected space and refracted space are placed at an optimal noise-free distance for focusing the reflected near-infrared response on their corresponding near-infrared photodetectors of 52 and 54. The extra set of mirrors are utilized in the refracted space to synchronize the pathlength and response recording.

Figure 7:
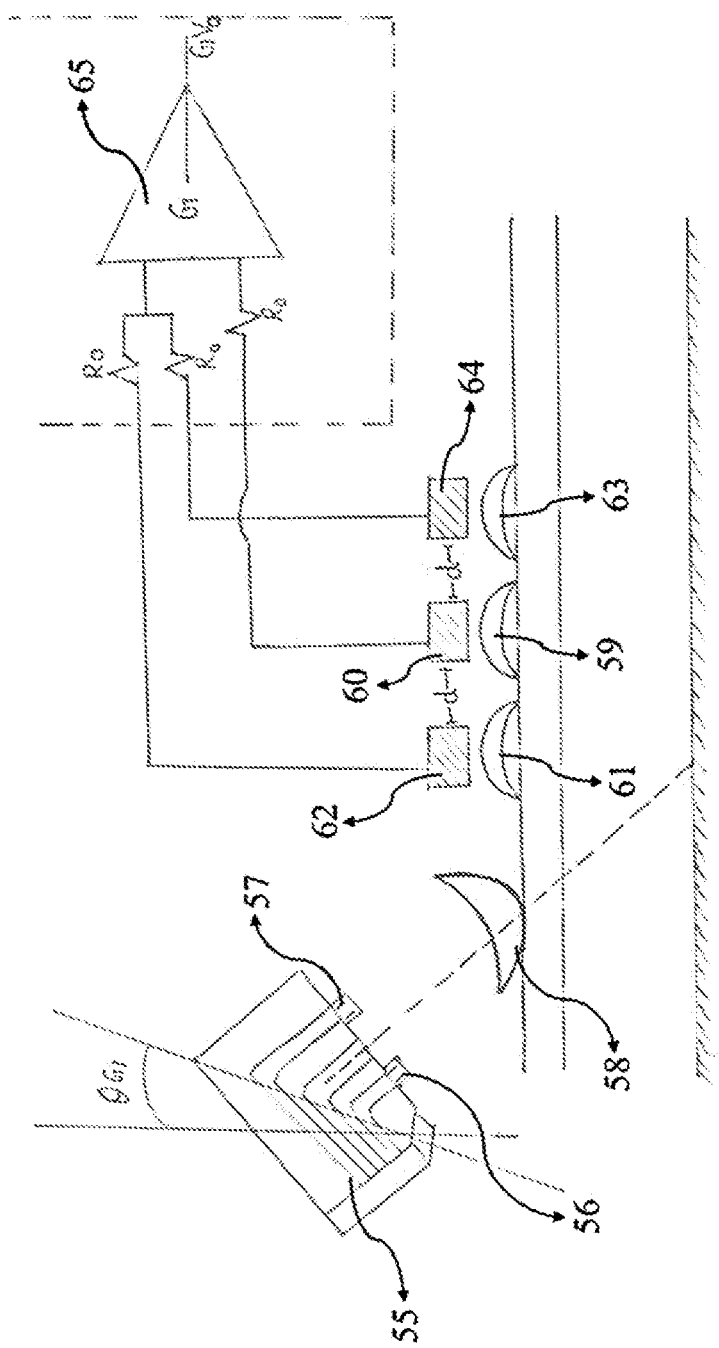
FIG. 7 is a dispersion analyser apparatus.

FIG. 7 is a dispersion analyser apparatus. The light emitting signal probes of 56-57 on signal board 55 are tilted at an angle of $\theta_{G1}$. The light by signal probes 56-57 are interfered and focused by an optical lens system 58 tilted at an angle of $\theta_{G1}$. The tilted optical lens 58 focuses the input light on the central photodetector system of optical lens 59 and central photodetector 60. A set of adjacent non-central photodetectors of 62-64 are placed on the either side of the central photodetector 60 at an optimal dispersion recording distance. The dispersive response signals are captured and focused by the set of non-central optical lenses of 61 and 63 on the corresponding non-central photodetectors of 62 and 64. The signal output terminals of the central photodetector's 60 response and summed response of non-central photodetectors 62-64 is attached to an instrumental amplifier 65. The output of the instrumental amplifier 65 is analysed for obtaining the dispersion information.

Figure 8:
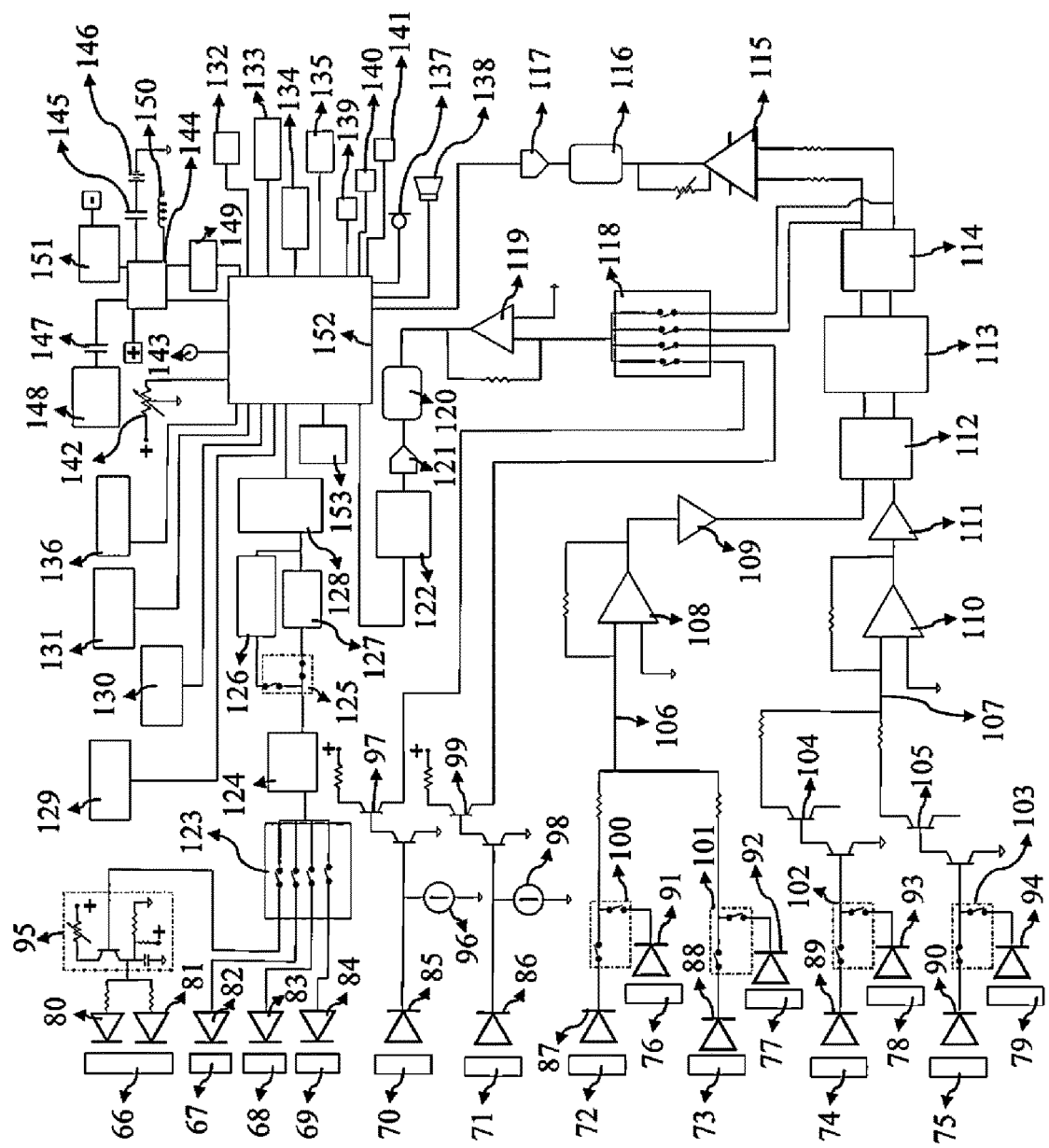
FIG. 8 is the low-powered electronic architecture of the reflective telemetry apparatus.

FIG. 8 shows the electronic hardware architecture of the reflective telemetry apparatus.

The set of optical lens system of 66, 67, 68 and 69 tunes and focuses the input radiation of the corresponding light sources of 80-81, 82, 83 and 84. The output response is focused by optical lens system of 70, 71, 72, 73, 74, 75, 76, 77, 78 and 79 on the corresponding photodetector probes of 85, 86, 87, 88, 89, 90, 91, 92, 93 and 94. The input to the near-infrared light sources of 80 and 81 are coherently driven through a resistor line and a tunable FET/RIT based active amplifier circuit 95. The signal input is variably triggered and sent through a LED frontend comprising of LED driver 124, PWM 127, switch set 125, LED controller 126 and clock controller 128. A signal probe end primary switch set 123 is utilized for connecting the LED frontend of 124-125-126-127-128 to the red LED 82, infrared LED 83, green LED 84 and active amplifier circuit 95 attached to the near-infrared LDs 80-81. The primary switch set 123 reduces the overall component use, power consumption and electrical tracing efforts.

The near-infrared output response recorded by the near-infrared photodetector probe 85 is shifted by small signal source 96 and amplified by the darlington pair 97. The response recorded by the green photodetector probe of 86 is shifted by small signal source 98 and amplified by the darlington pair 99. A set of switches of 100, 101, 102 and 103 are placed between the corresponding set of red photodetector-infrared photodetector of 87-91, 88-92, 89-93 and 90-94. The set of switches of 100, 101, 102 and 103 are utilized to alternatively record output response of the red photodetector probes of 87-88-89-90 and infrared photodetector probes of 91-92-93-94. The output response of proximity red-infrared photodetectors of 87-91 and 88-92 is separately extracted through a proximity response line 106 and summed through an op-amp circuit 108. The output response of the distant red-infrared photodetector set of 89-93 and 90-94 are amplified through darlington circuit of 104 and 105. The response of distant red-infrared photodetectors set is separately extracted through a distant response line 107 and summed through an op-amp circuit 110. The output line of proximity photodetectors and distant photodetectors are stabilized through a buffer circuit of 109 and 111. The summed proximity response line and summed distant response line are filtered and processed using a circuit line of ADC 112, ambient noise cancellation IC 113 and DAC 114. An Instrumental amplifier 115 with gain is attached to the proximity response line and distant response line for extracting the real-time dispersion information. The real-time dispersion is further filtered and recorded through a circuit line of power notch 116 and ADC 117. The processed output response lines of the individual light sources are attached to an op-amp circuit 119 through a photodetector end primary switch set 118. The photodetector-end primary switch set 118 is utilized to reduce the component use and overall power consumption. The output response through op-amp circuit 119 is filtered and processed through a circuit line of power notch 120, ADC 121 and ambient noise cancellation IC 122.

A MEMs/NEMs non-contact temperature biosensor 129 is attached to the hardware for extracting the real-time body temperature and temperature feedback. An ambient temperature sensor 130 of the hardware is utilized for extracting real-time environment temperature and feedback of the internal electronics. A MEMs/NEMs 9/6-axis accelerometer 131 is attached to the hardware, which is utilized as a real-time motion feedback for the bio-sensor and as a means to compute movement signals. The wireless antennae set of GPS 132, GSM 135, WLAN 133 and BLE 134 of the hardware are used for communicating the information between the telemetry apparatus and external devices. The wireless antenna set of 132-133-134-135 is also utilized to compute the real-time location and movement data of steps taken, speed, phase, etc. A mini touch display 136 is attached to the hardware, which is utilized for viewing and accessing the real-time medical information, real-time medical alerts, automated recommendations, notifications, data trends, daily health check-up data and other essential information. The touch display 136 is also used for operating the telemetry apparatus and its in-built applications. Apart from the display unit 136, the hardware of the telemetry device is attached to a user interaction system of mic 137, speaker 138, button set B1-B2-B3 139-140-141 and potentiometer integrated navigator 142. The navigator crown 142 comprises of a potentiometer and fixed impedance component. The set of interaction components of 136-137-139-140-141 are utilized for operating the telemetry apparatus and accessing the in-built applications. The set of user interaction hardware components of 136-137-138-139-140-141 are utilized as a means for interacting with the professional medical and health practitioners for clinical and health analysis. The speaker 138 is also used as the means to perceive the recorded and computed information. A fancy LED circuit 143 is attached to the hardware, which is utilized for automatically indicating the user condition, displaying decorative applications and representing different operating modes and device status.

The hardware of the telemetry apparatus is powered by a power supply unit comprising of power management IC 144, supercapacitor 145-battery set 146, supercapacitor 147-renewable energy harvester 148, wireless coil 150, USB module 149 and negative voltage converter 151. The power management IC 144 is used to regulate power supply. The supercapacitor 145-battery 146 is utilized for energy storage and powering the internal electronics. The supercapacitor 147-renewable energy harvester 148 is used as the auxiliary powering unit. The wireless coil 150 is used as the wireless method to charge the battery and power the internal electronics. The negative signal reference is generated by the negative voltage converter 151. The USB module 149 is used for powering the electronic circuit, charging the internal battery and communicating the data with the external devices.

The microprocessor 152 attached to memory 153, is used for communicating with the internal electronics and operating the internal electronic components. The microprocessor 152 with memory 153 is also utilized for computing and storing the required information.

Figure 9A:
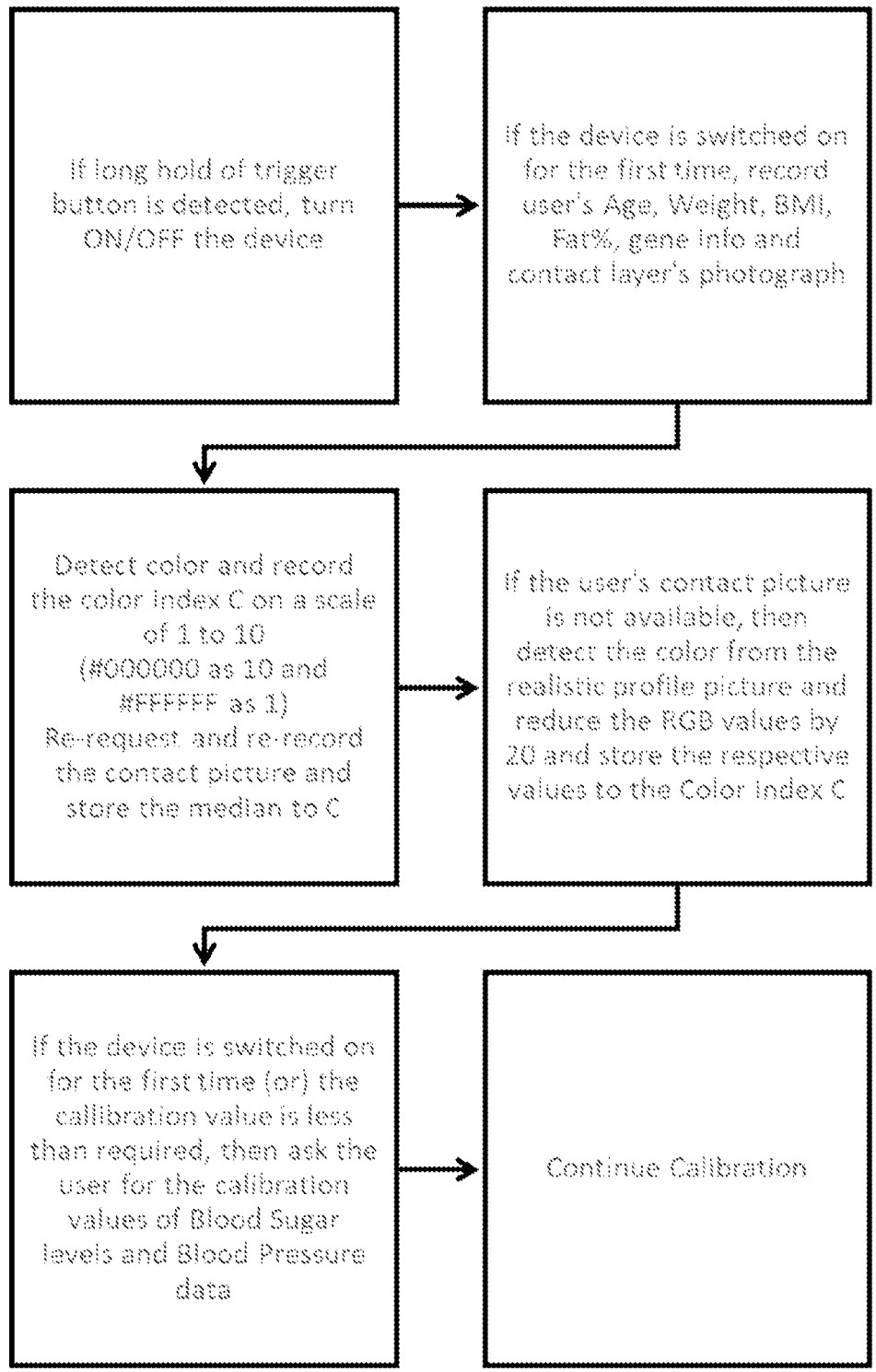
Figure 9B:
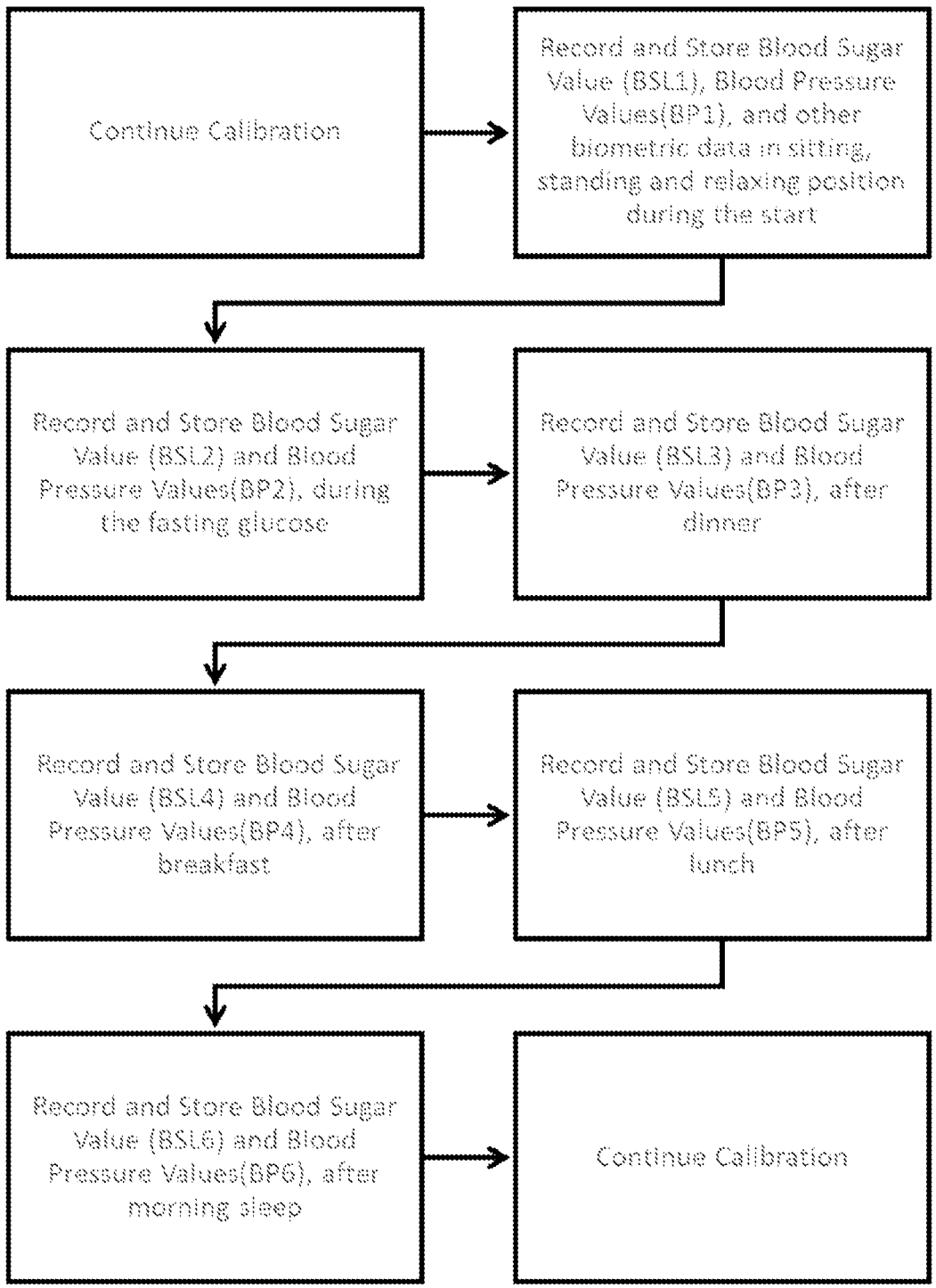
Figure 9C:
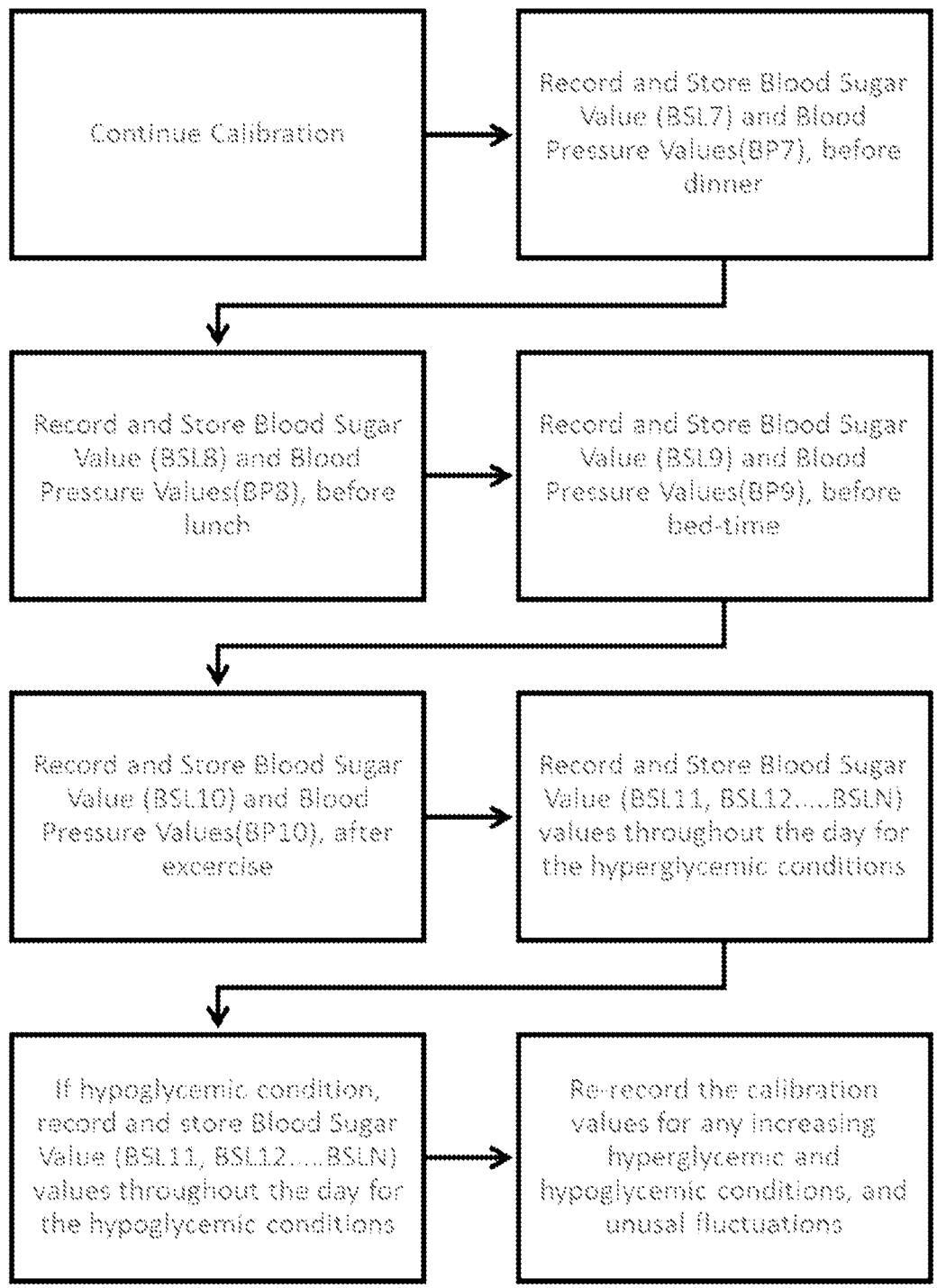

FIG. 9A, FIG. 9B and FIG. 9C show the method to calibrate the telemetry device. The user information of age, weight, BMI, fat %, gene info and contact layer's photograph are recorded during the initial device start-up. The recorded contact skin picture is analysed in the RGB hex code and deduced on a scale of 1 to 10. The device prompts the user to re-record the contact picture multiple times and the recorded contact skin picture is analysed to deduce the color of the contact surface. On unavailability of the contact surface picture, the realistic profile picture of the user is recognized, and the profile picture values are altered by an adjusting parameter to extract the contact layer skin color values. The blood sugar levels, blood pressure data and other real-time biological information of the user are recorded during the sitting position, standing position, relaxing position, fasting glucose, post-dinner, post-breakfast, post-lunch, post-morning sleep, post-exercise, pre-dinner, pre-breakfast, pre-lunch, before bed-time, hypoglycaemic state and hyperglycaemic state. The device prompts the user to re-record the blood sugar data, blood pressure levels and other real-time biological information for unusual fluctuations and increasing hyperglycaemic and hypoglycaemic conditions.

Figure 10A:
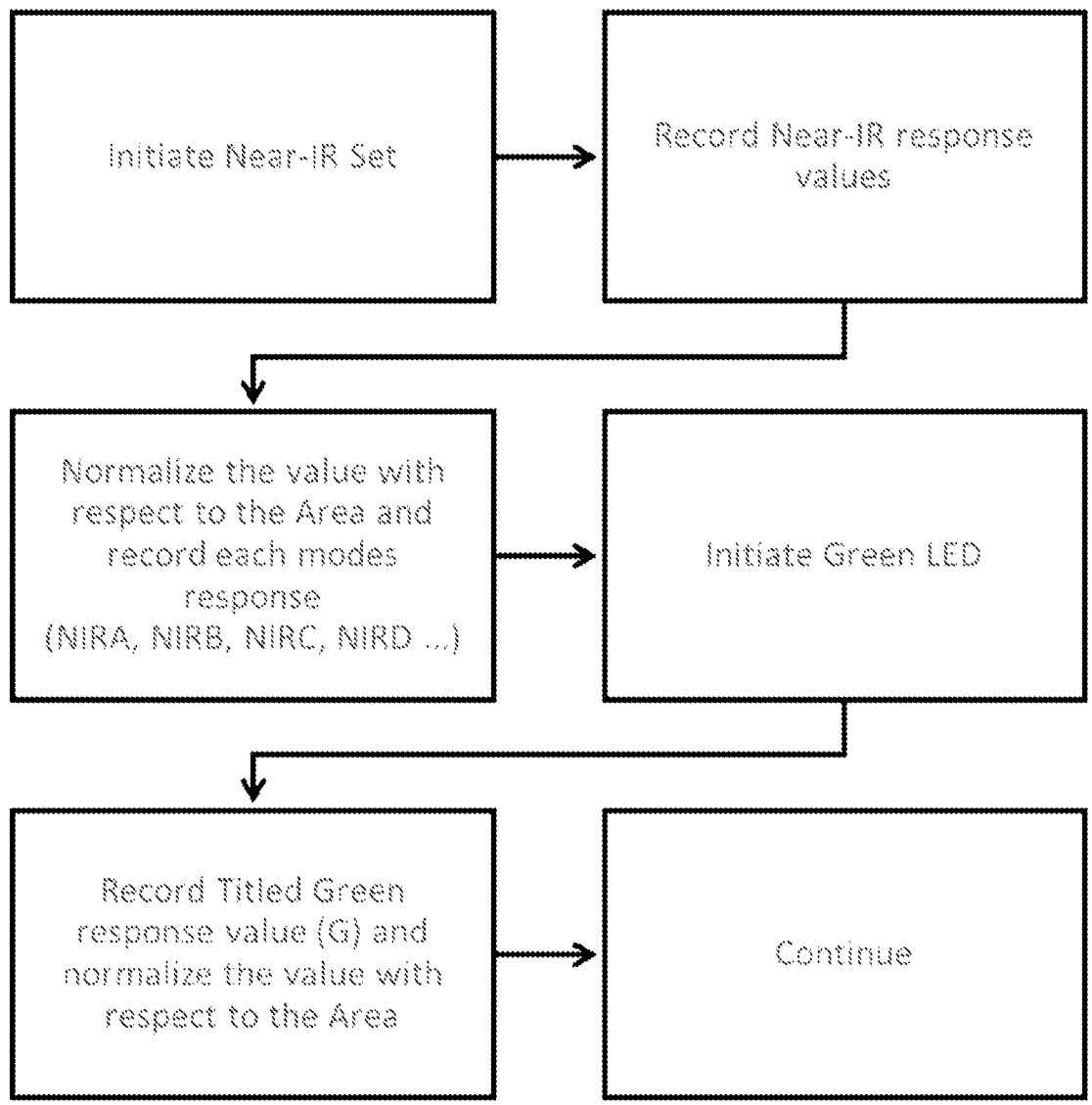
Figure 10B:
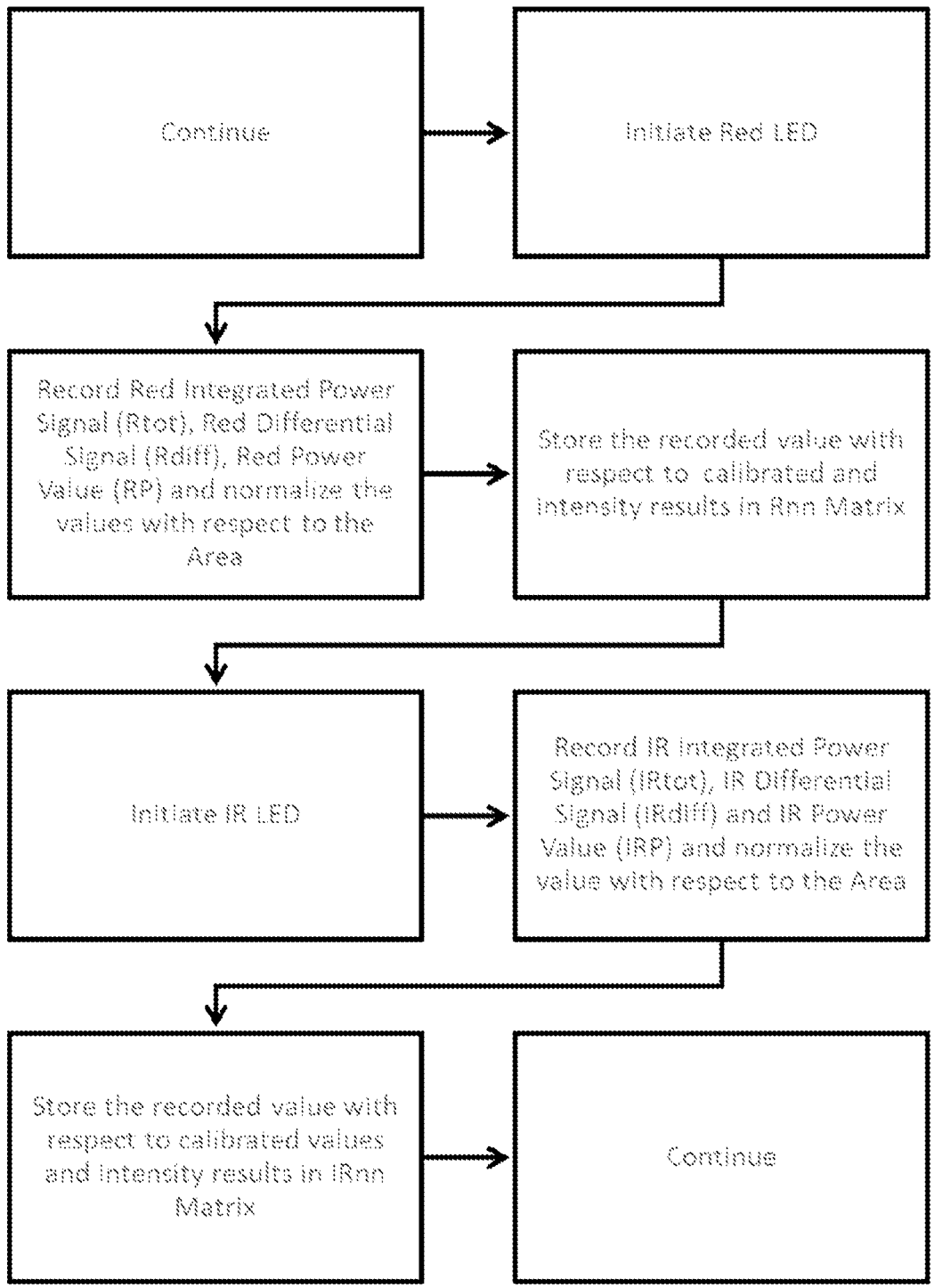
Figure 10C:
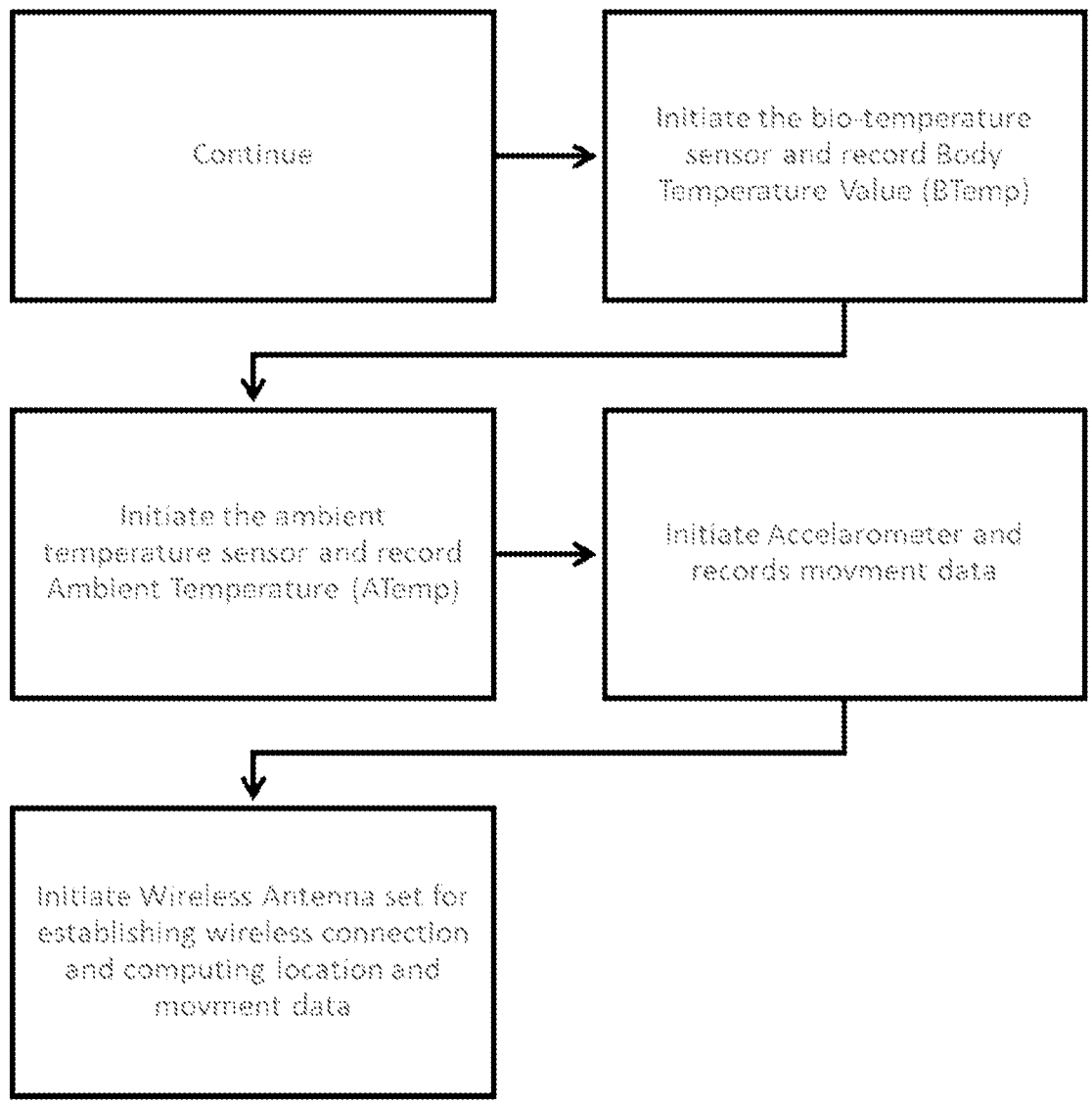

FIG. 10A, FIG. 10B and FIG. 10C show the process chart for sensor initialization and sensor response normalization. The near-infrared LDs, green LED, red LED, infrared LED and biosensors are initialized in a cyclic manner. The near-infrared response of different modes are recorded and normalized with respect to the area (NIRA, NIRB, NIRC, NIRD and so till NIRN). The green response is recorded and normalized with respect to the area (G). The red response values of red Integrated Power Signal (Rtot), red Differential Signal (Rdiff) and Red Power Value (RP) are recorded and normalized with respect to the area. The values of the red signal response are stored with respect to calibrated values in the Rnn Matrix. The infrared response values of IR Integrated Power Signal (IRtot), IR Differential Signal (IRdiff) and IR Power Value (IRP) are recorded and normalized with respect to the area. The values of the infrared signal response are stored with respect to calibrated values in the IRnn Matrix. The system initializes the bio-temperature sensor and ambient temperature sensor for recording the real-time bio-temperature values (Btemp) and ambient temperature values (Atemp). The accelerometer and wireless antennae are initialized for recording the movement data, location data and establishing wireless communication.

Figure 11A:
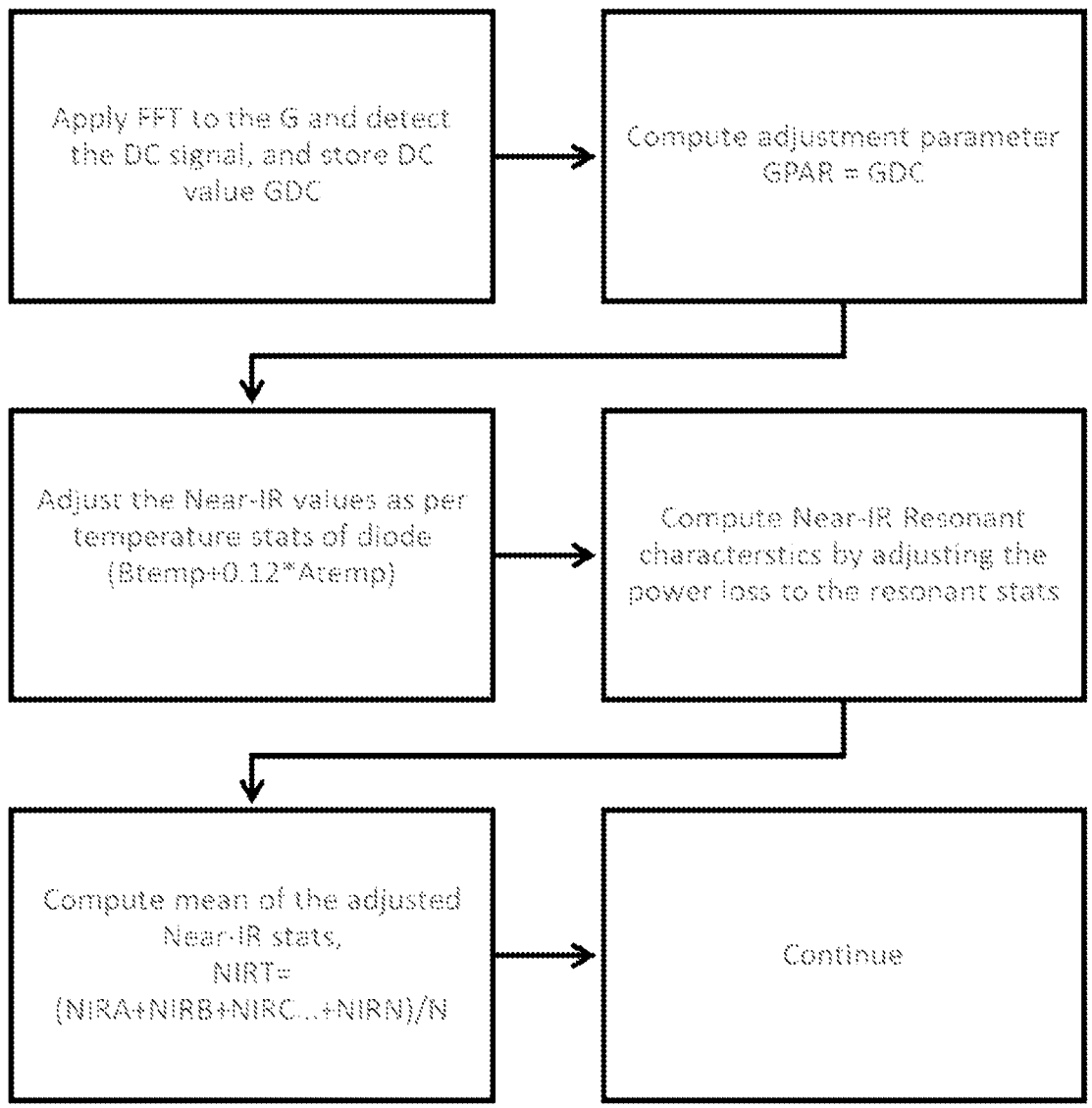
Figure 11B:
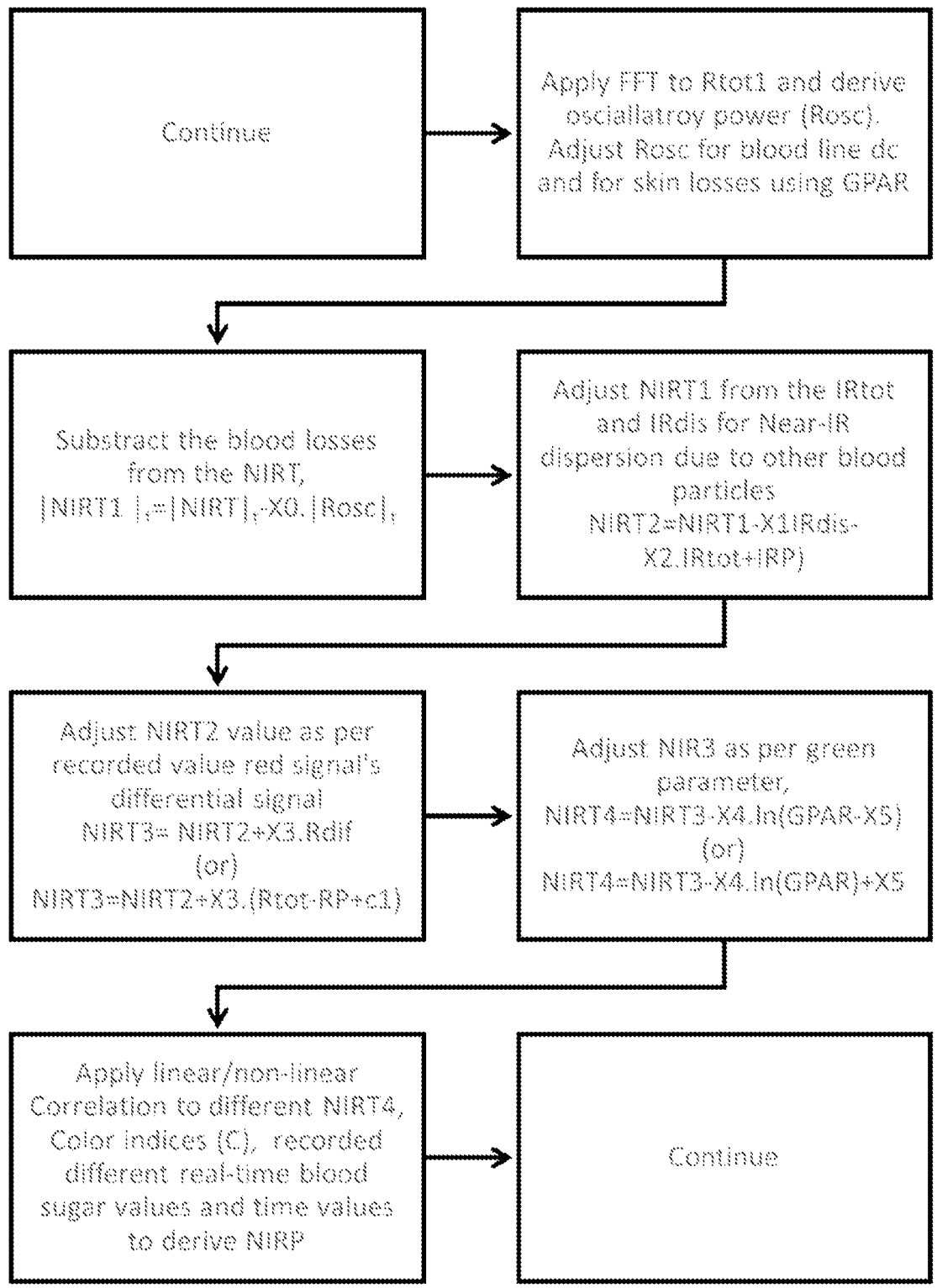
Figure 11C:
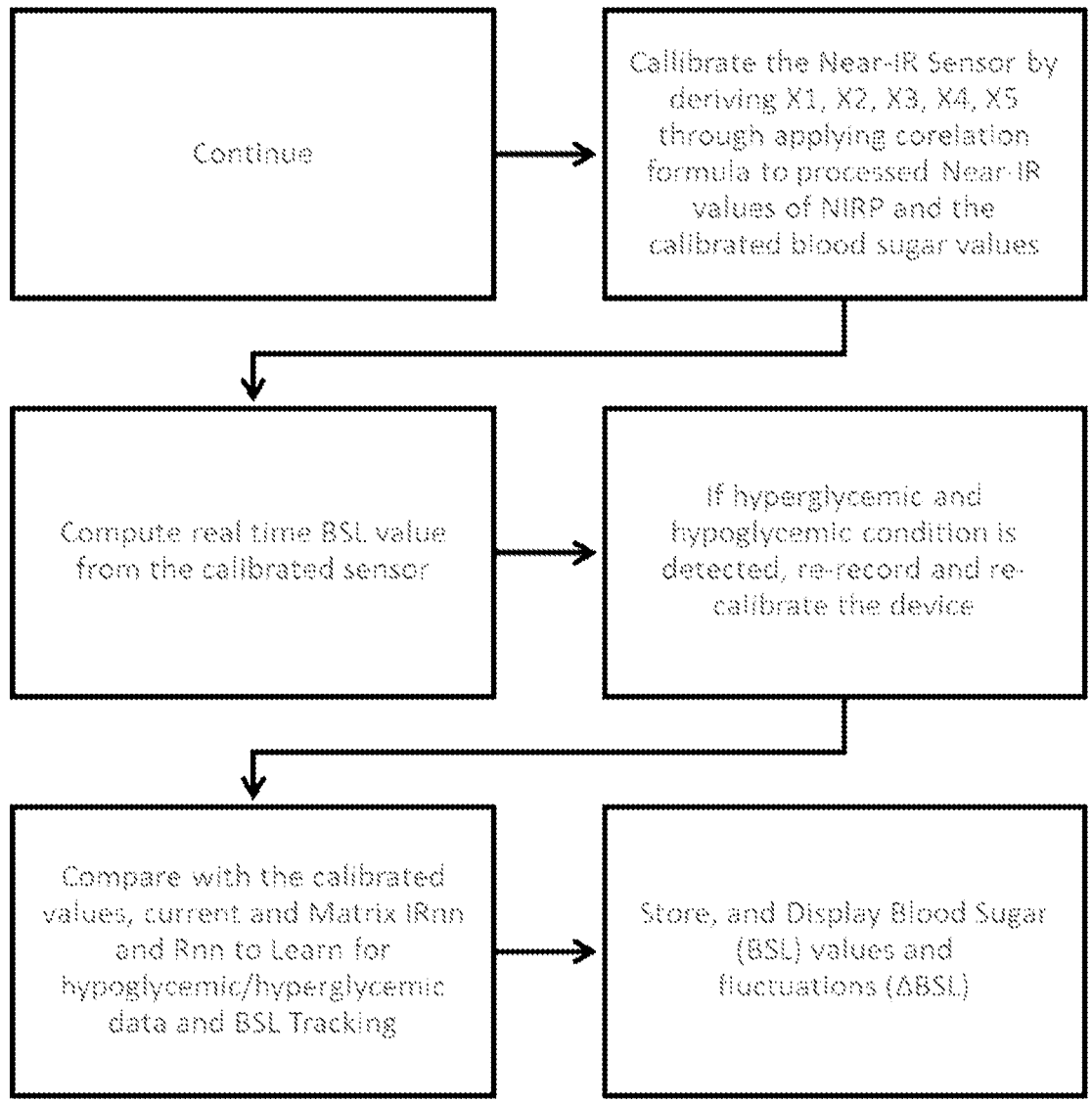

FIG. 11A, FIG. 11B and FIG. 11C is the real-time system for monitoring the continuous blood sugar levels. The recorded green sensor response of G is analyzed to recognize the green sensor DC parameter losses (GDC). The green parameter (GPAR) is deduced from green sensor DC parameter (GPAR=GDC). The recorded near-infrared response values are adjusted as per the temperature stats of the bio-temperature and ambient temperature response and the mean of the adjusted near-infrared modes (NIRT) is deduced by NIRT=(NIRA+NIRB+NIRC+so on till NIRN)/N). The real-time system processes the recorded red signal to deduce oscillatory red signal values (Rosc) and the oscillatory red response values (Rosc) are adjusted for skin losses using the green parameter (GPAR). The blood line losses free 1st order near-infrared sensor value (NIRT1) is extracted from the oscillatory red response (Rosc) and normalized near-infrared response (NIRT) using linear and non-linear analysis method ($|NIRT1|_t=|NIRT|_t-X0.|Rosc|_t$). The first order near-infrared (NIRT1) is processed with the infrared response (of IRtot and IRdis) for adjusting the near-infrared response for non-haemoglobin particle and other blood particle losses (NIRT2=NIRT1-X1IRdis-X2.(IRtot+IRP)). The $2^{nd}$ order near-infrared response (NIRT2) response is further linearly or non-linearly correlated with the red differential value (Rdiff) for extracting the $3^{rd}$ order near-infrared response (NIRT3=NIRT2+X3.Rdif). The extracted $3^{rd}$ order near-infrared response (NIRT3) is analyzed with green parameter (GPAR) in the equation form of either power exponent or linear representation of unknown intercept and unknown coefficient for extracting the $4^{th}$ order near-infrared response (NIRT4=NIRT3-X4.ln (GPAR-X5) (or) NIRT4=NIRT3-X4.ln (GPAR)+X5). The processed near-infrared response is adjusted for recorded color index C and real-time blood sugar values using non-linear and linear correlation. The processed near-infrared response is correlated with the recorded blood sugar calibration values utilizing non-linear and linear correlation for computing the real-time continuous blood sugar values. The real-time blood sugar values (BSL) and blood sugar fluctuations (ABSL) are stored and displayed. The real-time BSL values are further learnt with respect to the calibrated values and red and infrared response for recognizing hypoglycemic and hyperglycemic data and blood sugar levels. The real-time system records additional calibration values for recognized conditions of hypoglycaemia, hyperglycaemia and unusual blood sugar fluctuations.

Figure 12A:
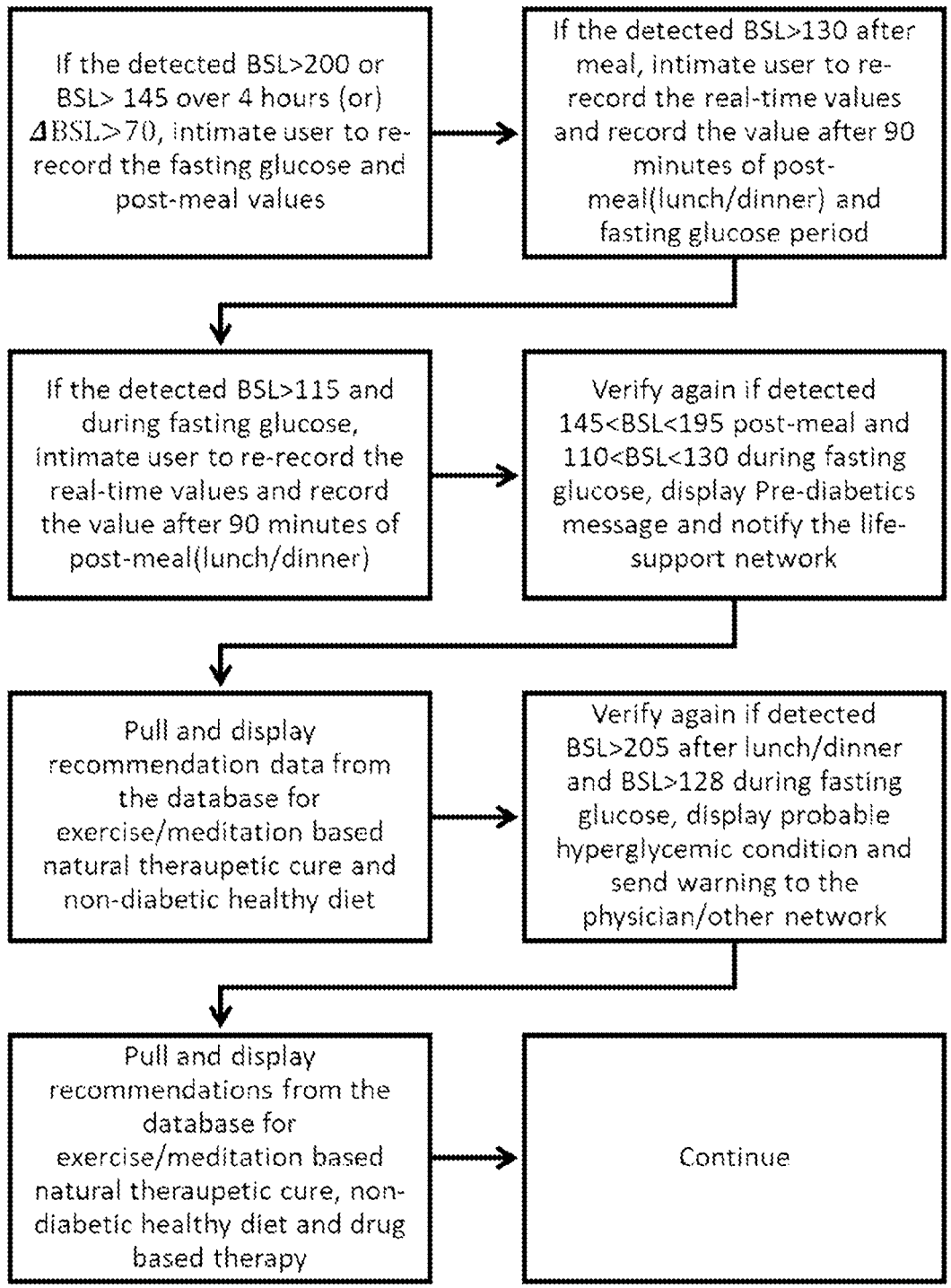
Figure 12B:
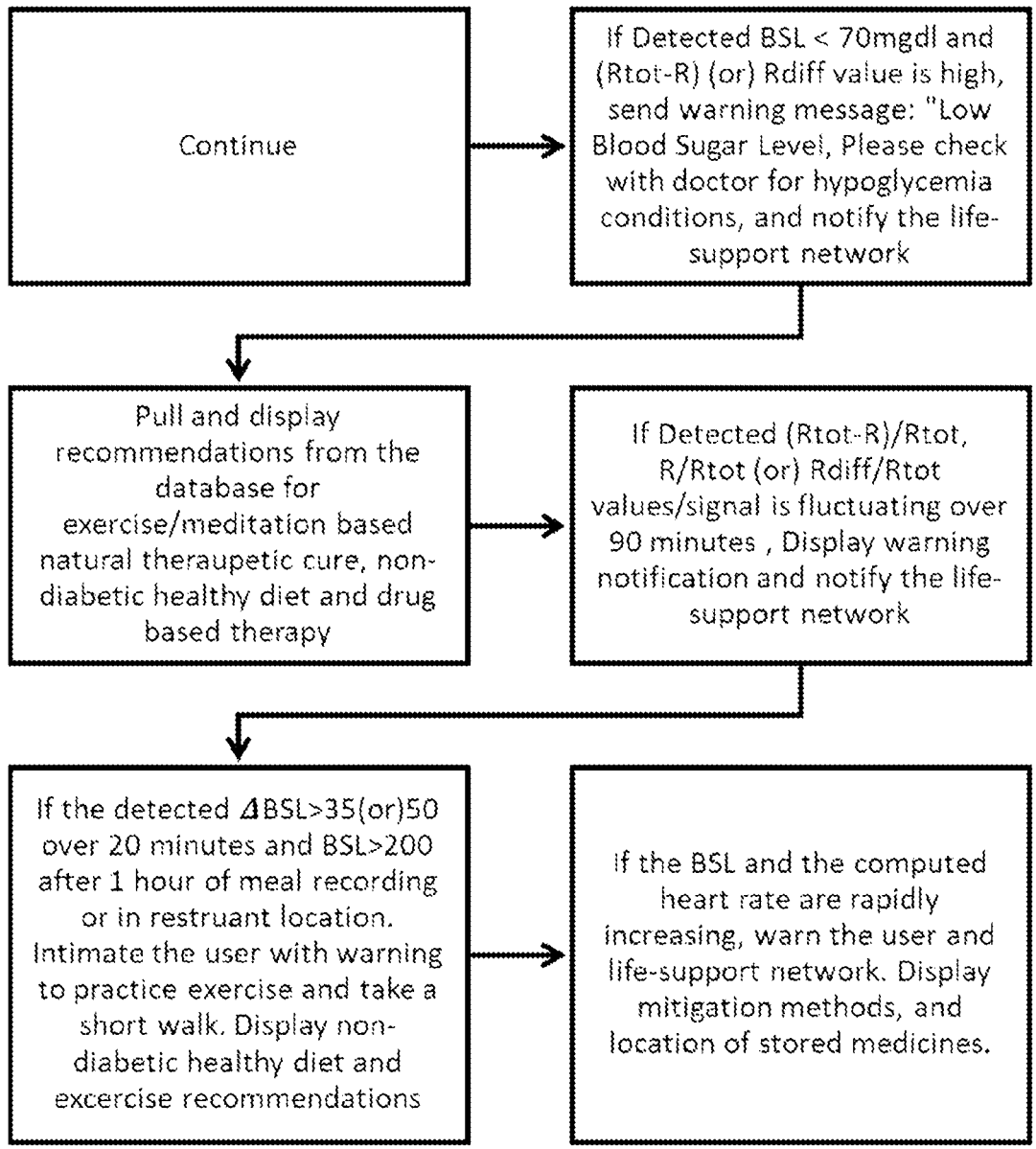

FIG. 12A and FIG. 12B show the method of blood sugar analysis for recognizing the hypoglycaemia, hyperglycemia and unusual blood sugar fluctuations. The values of continuous blood sugar values (BSL) and blood sugar fluctuations (ABSL) are analyzed during fasting glucose state, post-meal state, post-sleep condition, regular condition and pre-meal state for recognizing prediabetic threshold condition, hyperglycaemia threshold condition and hypoglycaemia threshold condition. The real-time system analyses BSL fluctuation values (ABSL) and real-time BSL values with respect to user location. The pulse rate and blood sugar data are evaluated for threshold blood sugar conditions and other health issues. The real-time system analyses and evaluates the red signal values, red signal dispersion values, infrared radiation dispersion values and visible signal values [(Rtot-R)/Rtot, R/Rtot, Rdiff/Rtot, IRdiff, IRtot and so on] for learning and recognizing unusual blood sugar fluctuations, hyperglycemia, hypoglycaemia and prediabetes conditions. The system informs the user with information on the recognized health condition, present blood sugar levels and current blood sugar fluctuations. Subsequently, the system verifies probable symptoms, and automatically generates and displays recommendations from database on therapy methods, treatment centres, lifestyle practices, diet suggestions, physical activities, mitigation methods and medication advice to treat and manage the recognized blood sugar conditions. The real-time system also automatically notifies and alerts the life-support network with a warning message and information on user data, user condition, user location, recognized health condition, present blood sugar levels, current blood sugar fluctuations and other essential data. Based on the real-time data and recognized health conditions, the user is automatically presented with real-time medical alert, medication reminder and information on location of the medication.

FIG. 13 shows the real-time system for monitoring continuous blood pressure levels. Initially, the recorded red signal response is adjusted according to the green signal response (Rtot1=Rtot−Y.ln(GPAR)). Then the oscillatory values of the red signal ($RT_{osc}$) are derived from the adjusted red signal values. Then, the peak to peak cycle of the red signal is analysed for a fixed time span for deriving the power of the red oscillatory signal (RP=$\Sigma \int_0^{tpeak} |RTosc|*|RTosc|$). The linear and non-linear correlation is applied to the red signal power and calibrated blood pressure value to compute the real-time blood pressure (Ex: BP=X.RP). Then, the sensors are calibrated for tracking real-time blood pressure. The computed continuous blood pressure values are stored and displayed.

Figure 14A:
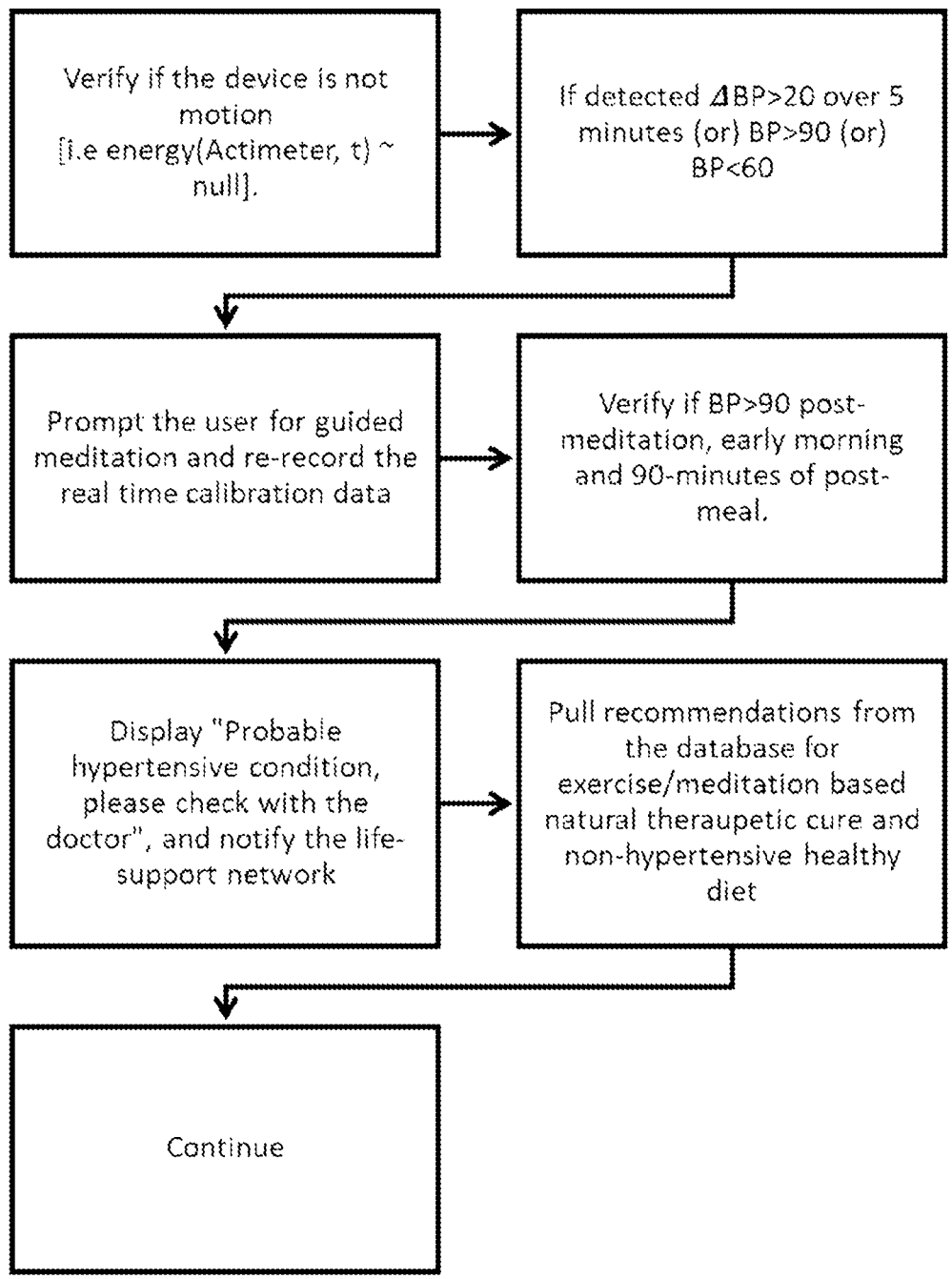
Figure 14B:
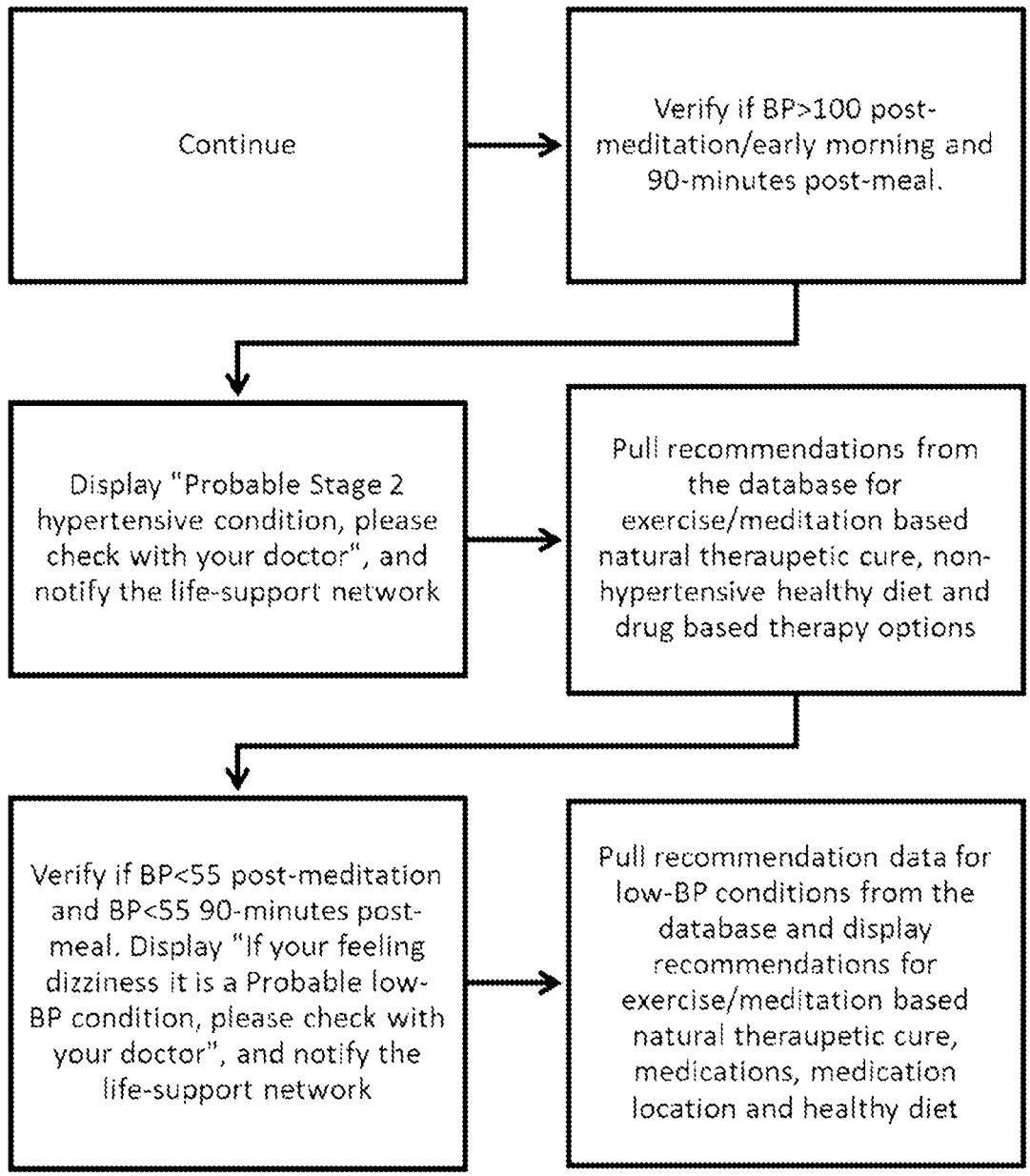

FIG. 14A and FIG. 14B show the method to analyse the continuous blood pressure data for recognizing the hypertension, hypotension, and unusual blood pressure fluctuations.

The values of continuous blood pressure values (BP) and blood pressure fluctuations (ΔBP) are analyzed during fasting glucose state, post-meal state, post-sleep state, post-meditation state, regular condition, and pre-meal state for recognizing hypertension, hypertension stage 2, hypotension, and unusual blood pressure fluctuations. The system further analyses the blood pressure values (BP) and blood pressure fluctuations (ΔBP) for different locations. The system informs the user with information on the recognized health condition, present blood pressure levels and current blood pressure fluctuations. Subsequently, the system verifies probable symptoms, and automatically generates and displays recommendations from database on therapy methods, treatment centres, lifestyle practices, diet suggestions, physical activities, mitigation methods and medication advice to treat and manage the recognized blood pressure condition. Then, the real-time system also automatically notifies and alerts the life-support network with a warning message and information on user data, user condition, user location, recognized health condition, present blood pressure levels, current blood pressure fluctuations and other essential data. Based on the real-time data and recognized health conditions, the user is automatically presented with real-time medical alert, a message to consult the doctor, medication reminder and information on location of the medication.

FIG. 15 shows the real-time system and automated method for recognizing psychological stress. The real-time system initially evaluates the real-time blood pressure and blood pressure fluctuations for verifying the state of psychological stress. Then, neural parameters of HP1, HP2 and HP3 are derived utilizing temporal analysis. The peak to peak temporal values of red signal response are evaluated for 0.05 s interval difference for deriving HP1. The peak to peak root mean square and mean values are evaluated for deriving HP2 and HP3. The derived parameters of HP1, HP2 and HP3 are compared with the resting values of HP1, HP2 and HP3 for recognizing the state of emotional stress. The system verifies the location data for verifying the state of emotional stress with respect to the relevant location (Ex: stress at work and home is common, else it is chronic stress condition). Then, the real-time system automatically notifies the user regarding the state of emotional stress and generates suggestions to manage the stress through exercise, guided meditation and diet and social networking platform. The real-time system also automatically alerts and notifies the life-support network with a warning message and information on user data, user condition, user location, recognized emotional condition.

FIG. 16 shows an automated sleep tracking system. The real-time system evaluates the movement data, body temperature, blood sugar levels, blood pressure data and bio-signal data of the user for recognizing the sleep. Then, the system assesses the values of blood pressure data, blood sugar levels and neural parameters (of HP1, HP2 and HP3)

with sleep and wake data for recognizing REM sleep cycle and NREM sleep cycle. The REM cycle duration, NREM cycle duration, total sleep duration and sleep health are incremented and cached. The computed results are stored and displayed. The real-time system further analyses the actimeter data and sleep results to automatically recognize the sleep quality and the disturbed sleep condition. Based on the recognized sleep quality, the symptoms are verified, and the system automatically generates recommendations from database on recovery techniques, meditation methods, therapy, treatment centres, lifestyle practices, diet suggestions, physical activities, medications and health advice to manage the recognized sleep disorder. The real-time system also automatically alerts and notifies the life-support network with a warning message and information on user data, user condition, user location and recognized health condition. A learning method is applied on the derived parameters for reducing analysis parameters count, mode switching, complexity and power consumption of the processing method.

FIG. 17 shows a program for operating the telemetry apparatus using the buttons and navigator input. The long hold of button B1 turns on/off the device and short hold of button B1 swaps the operating modes of the device. The three short holds of the button B2 switches on/off the IOT parallel computational mode and wireless mode of the device. The long hold of button B2 facilitates the wireless synchronization and wireless data transfer between the telemetry apparatus and wireless devices. On recognizing long hold of the button B3, the device prompts the user to record the calibration values and real-time biometric values. The 5 short holds button B3 marks psychological stress levels of the user. Simultaneous long hold of B1/B3 and B2 silently triggers Emergency Alert in the wireless life-support network. Simultaneous long hold of B1 and B3, triggers alarm and medical emergency alert in the wireless life-support network. The rotation of the navigator crown swaps internal applications of the current mode in the direction of voltage shift or adjusts the intensity of the fancy LED.

FIG. 18 shows a user database based method for estimating calibration and health parameters. The color index, age, BMI, fat %, gene Info, sensor intensity, signal response and real-time calibration values are recorded from the individual user devices and sent to the central server. The values sent from the user device to the central server are analyzed and statically matched with the previously recorded parameters of the database. The optimization parameters of color index, sensor calibration data, healthy H.R. index, performance index and progress index are learnt and derived from the central database. The parameters are returned to user device, which is utilized for processing the real-time biological information and other health parameters.

FIG. 19 shows the design of the automated emergency response system. The emergency response system comprises of near—by synchronized mobile devices, SOS network, paired life-support devices and devices in the location of user's vicinity. On recognizing emergency trigger, the system checks for the status of the wireless antennae and the system automatically turns on the switched off wireless antennae. The location data and real-time biological information are recorded through the wireless antennae set and the internal sensors. The recorded information is transferred to the central server, SOS network, synchronized life-support device and the devices in the vicinity of user location. The set of life-support devices gets synchronized and receives the dataset. The life-support network triggers the primary network for transferring next dataset to the life-support network. The wireless data transfer occurs through directly via medium of central server and through other wireless methods.

FIG. 20 shows the network of wireless computational and storage devices. The Telemetry device 154 transfers the information to the server computer 155 and the other accessorial devices 156 through wireless methods. The accessorial mobile apparatus 156, server computer 155 and other network devices are utilized for parallelly computing and storing the information. This network of devices based method is used as a faster and efficient means to compute and store the required information. When necessary, the user device 154 retrieves the computed and stored information from the server 155 and accessorial devices network 156.

FIG. 21 shows the fancy LED apparatus. The fancy LED 157 emits multi-colored light in the line of branching multiple optical tubes 158. The light emitted to represent different device modes, device status and decorative application is perceived through the different branches of the multiple optical tubes 158.

Series of FIG. 22 show automated user interface of the telemetry apparatus and synchronized accessorial mobile device for recording user information and calibration values.

Figure 22A:
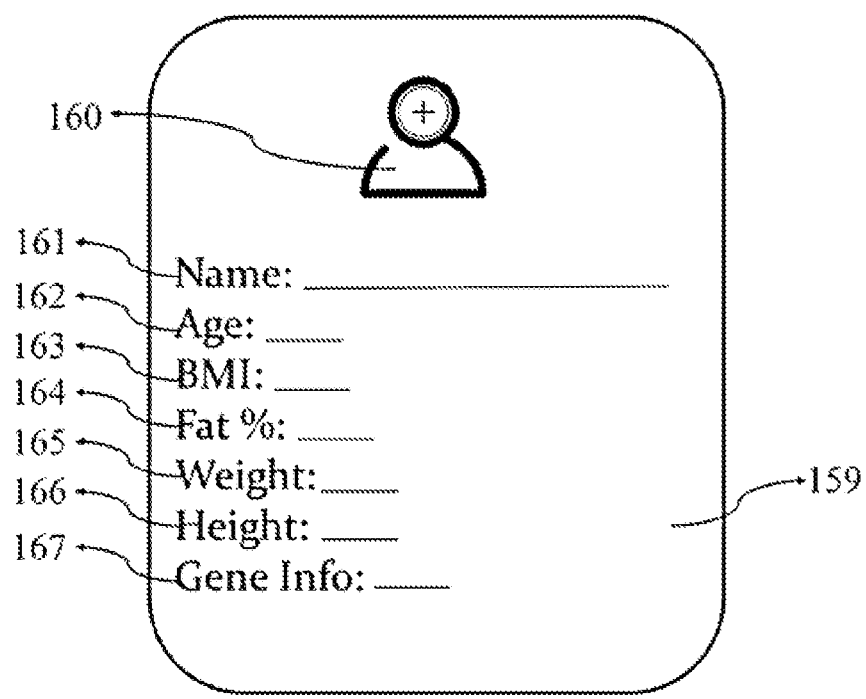
Figure 22B:
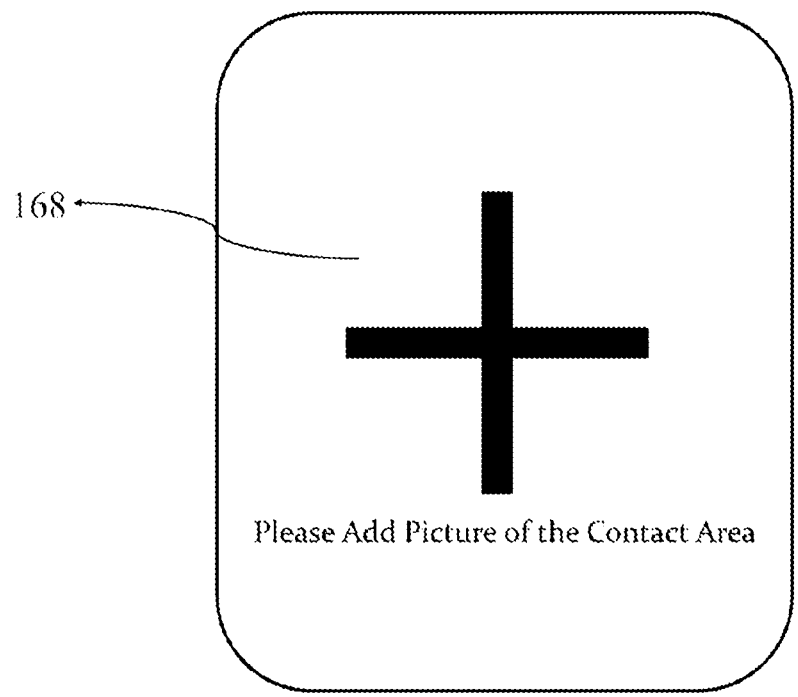
Figure 22C:
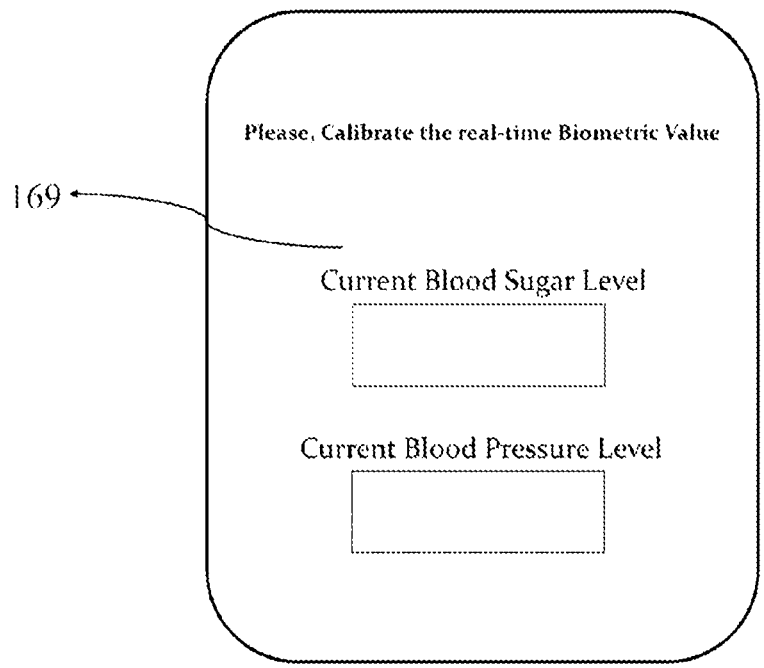
Figure 22D:
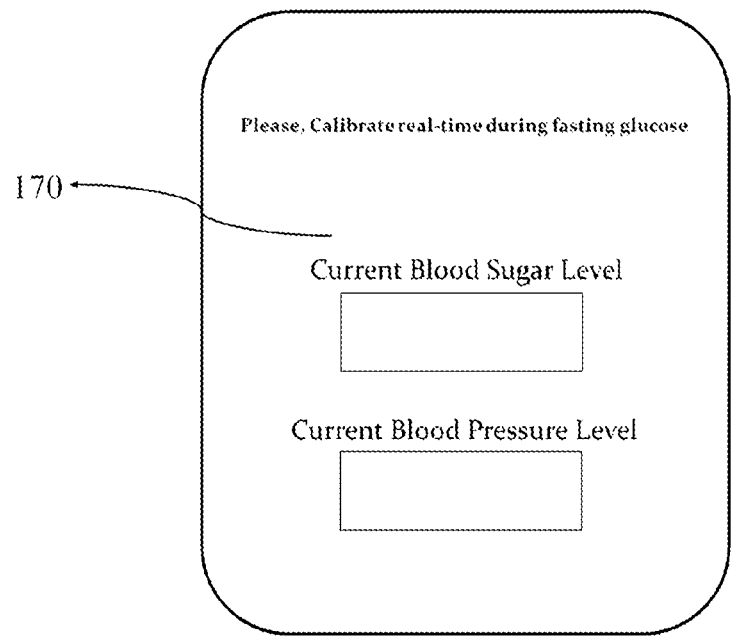
Figure 22E:
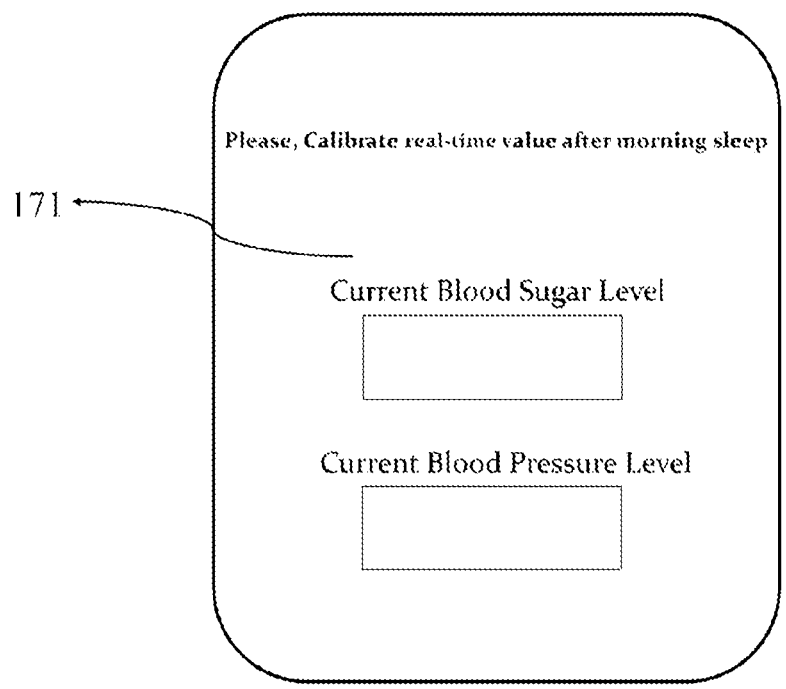
Figure 22F:
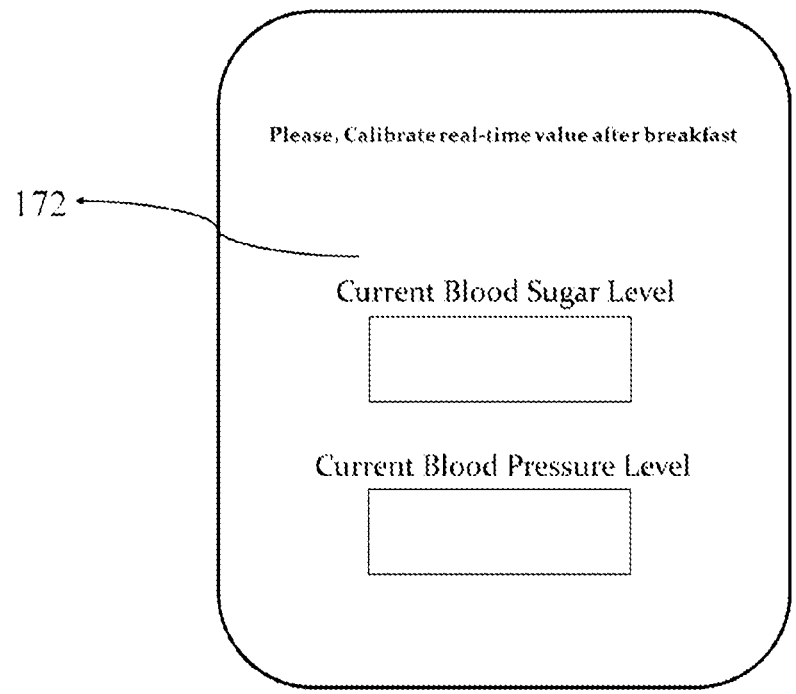
Figure 22G:
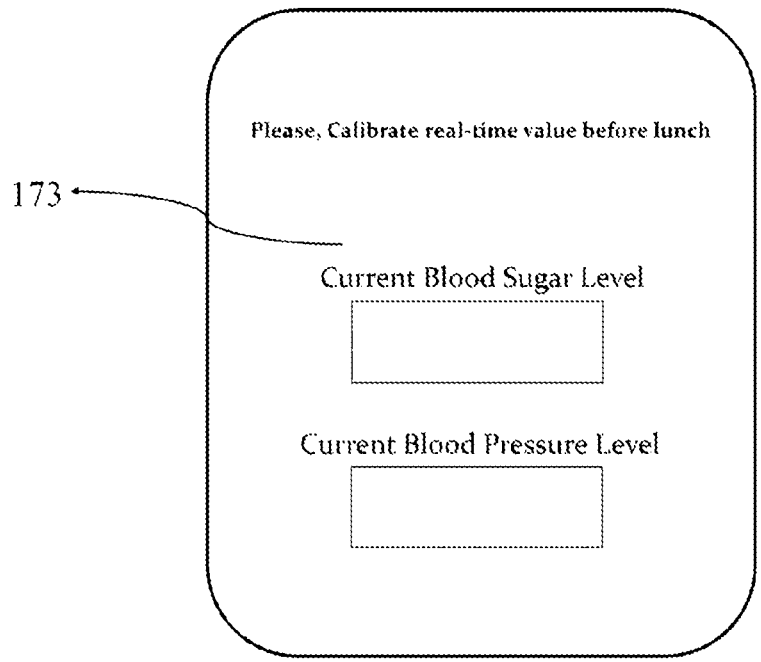
Figure 22H:
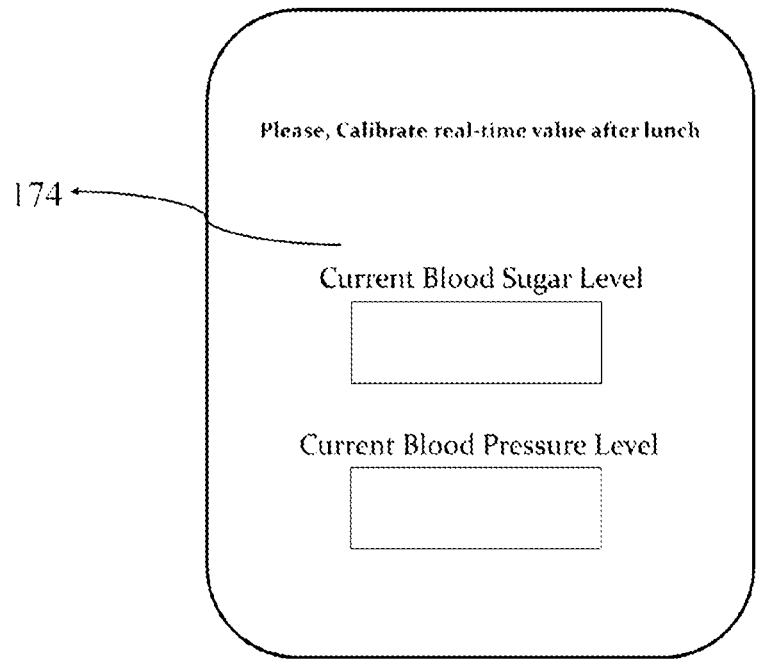
Figure 22I:
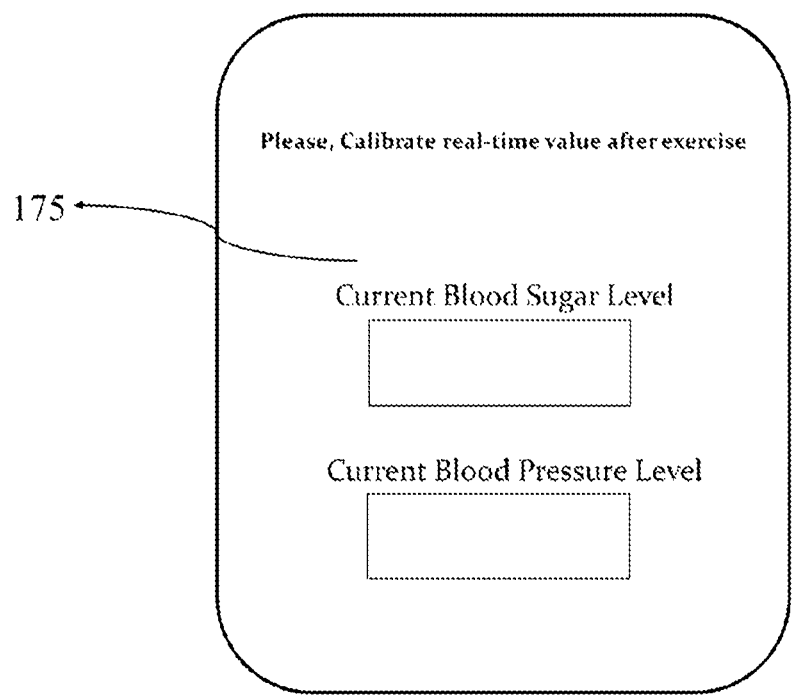
Figure 22J:
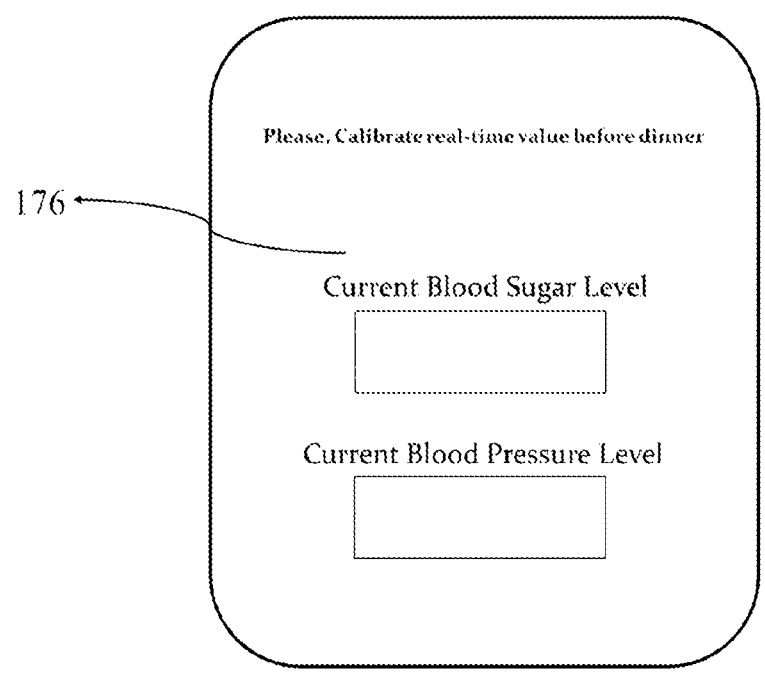
Figure 22K:
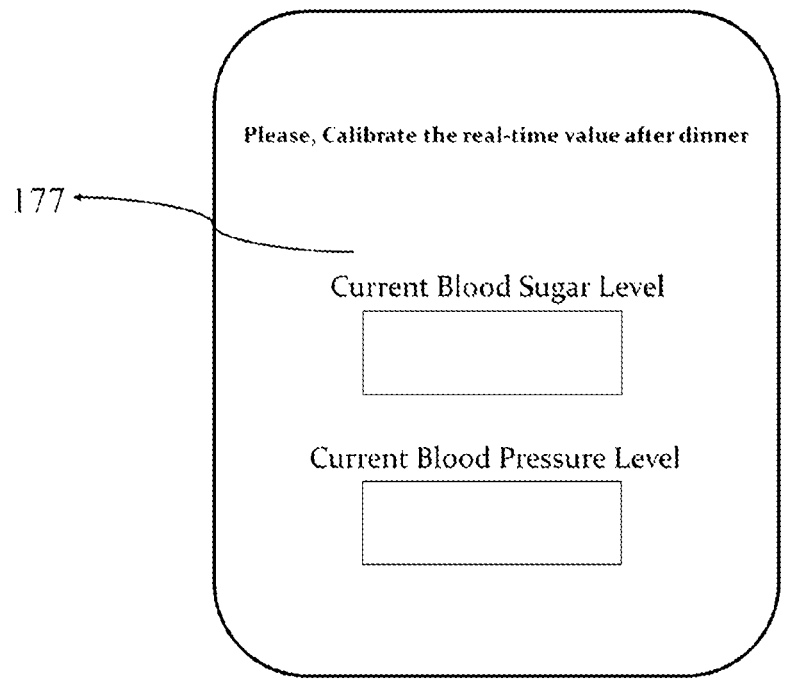
Figure 22L:
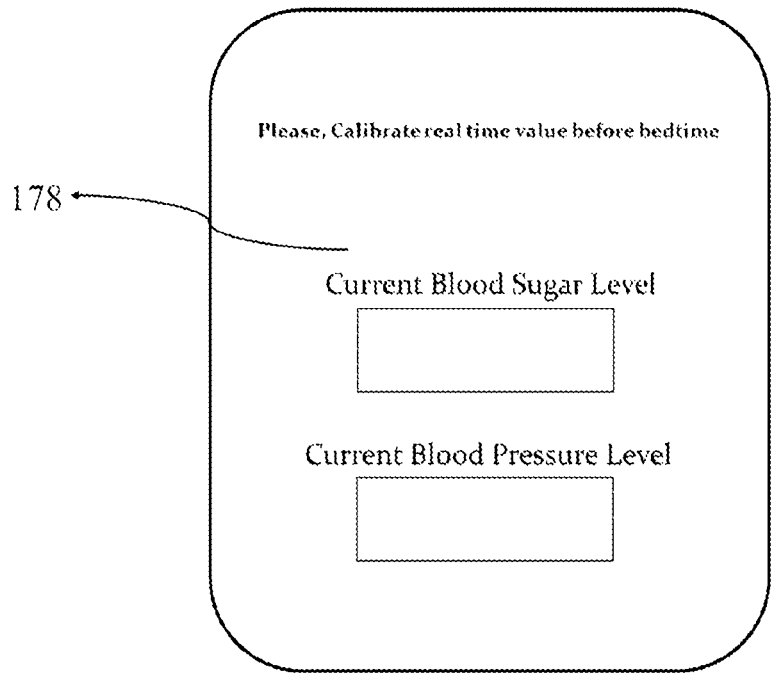
Figure 24A:
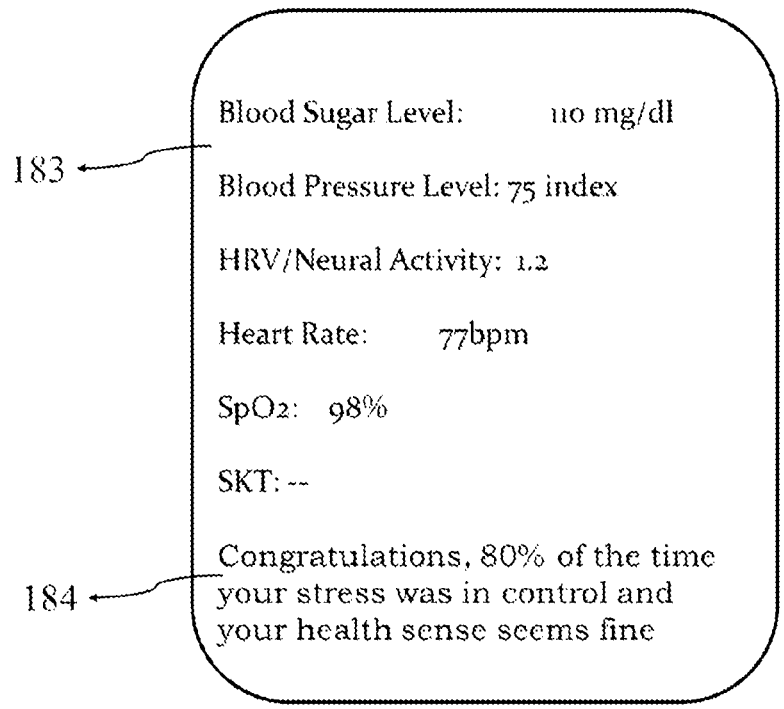
Figure 24B:
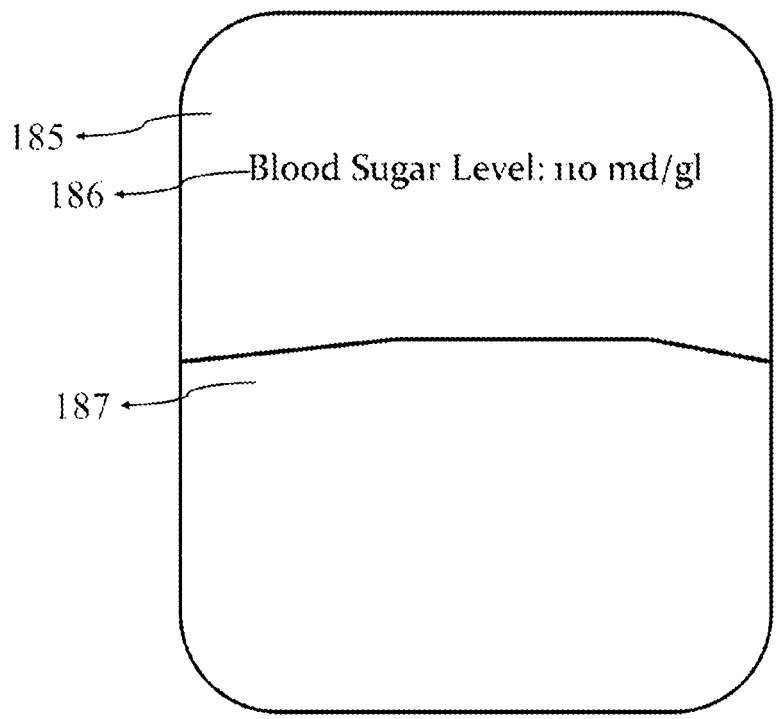
Figure 24C:
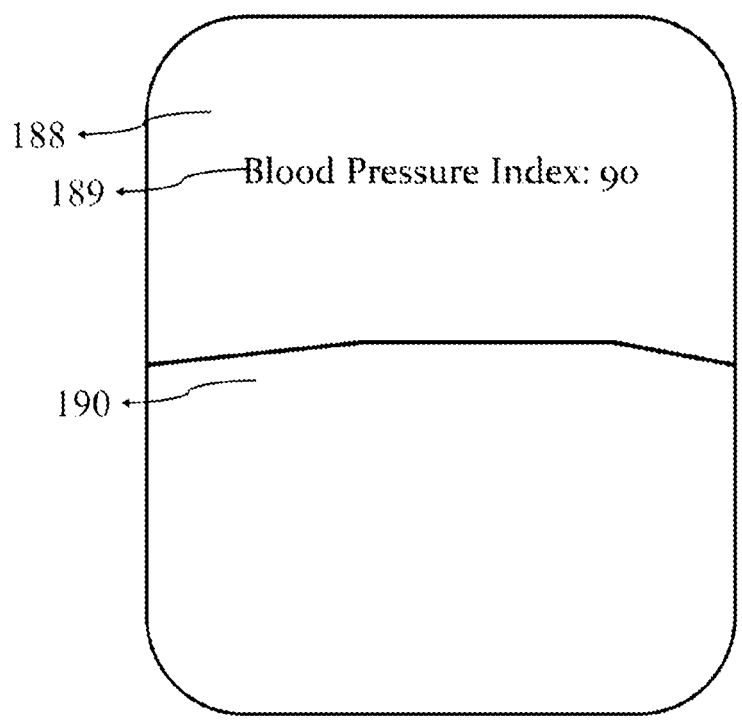
Figure 24D:
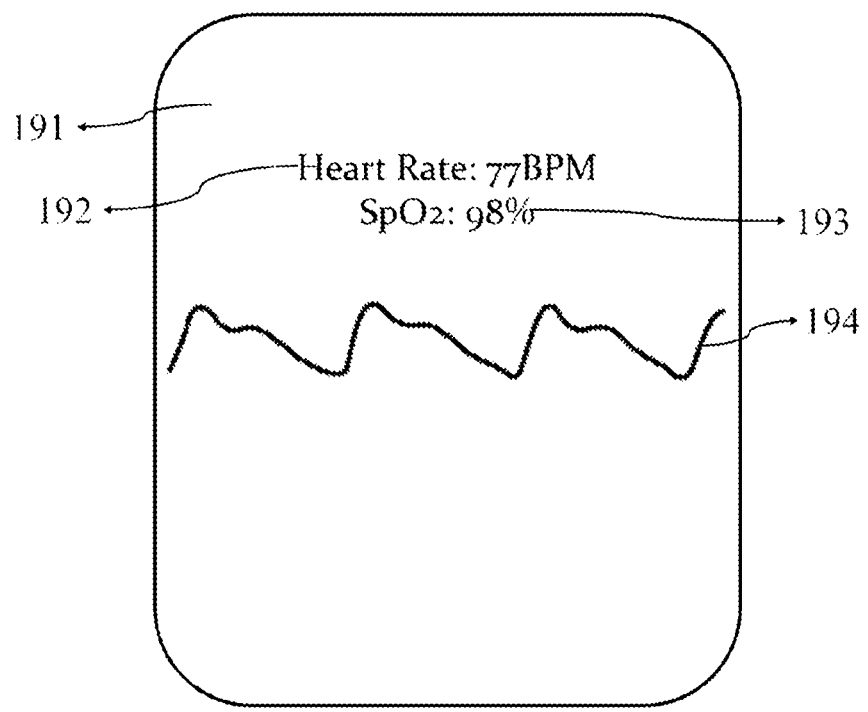

FIG. 22A shows the user interface 159 for recording the essential user information. During the device startup, the profile picture 160, user name 161, age 162, basal metabolic index 163, fat % 164, weight 165, height 166 and gene info 167 of the user are recorded through the real-time telemetry or the accessorial mobile apparatus. FIG. 22B shows the interface 168 for recording contact picture. FIG. 22C is the automated interface 169 of the telemetry apparatus and the accessorial mobile apparatus for recording the calibration values of real-time blood sugar levels and blood pressure data during the device startup. FIG. 22D is the interface 170 of the telemetry apparatus and the accessorial mobile apparatus for recording the calibration values of real-time blood sugar levels and blood pressure data during the state of fasting glucose. FIG. 22E is the automated interface 171 of the telemetry apparatus and the accessorial mobile apparatus for recording the post morning sleep calibration values of real-time blood sugar levels and blood pressure data. FIG. 22F is the interface 172 of the telemetry apparatus and the accessorial mobile apparatus for recording the post-breakfast calibration values of real-time blood sugar levels and blood pressure data. FIG. 22G is the interface 173 of the telemetry apparatus and the accessorial mobile apparatus for recording the pre-lunch calibration values of real-time blood sugar levels and blood pressure data. FIG. 22H is the interface 174 of the telemetry apparatus and the accessorial mobile apparatus for recording the post-lunch calibration values of real-time blood sugar levels and blood pressure data. FIG. 22I is the interface 175 of the telemetry apparatus and the accessorial mobile apparatus for recording the post-exercise calibration values of real-time blood sugar levels and blood pressure data. FIG. 22J is the interface 176 of the telemetry apparatus and the accessorial mobile apparatus for recording the pre-dinner calibration values of real-time blood sugar levels and blood pressure data. FIG. 22K is the interface 177 of the telemetry apparatus and the accessorial mobile apparatus for recording the post-dinner calibration values of real-time blood sugar levels and blood pressure data. FIG. 22L is the interface 178 of the telemetry apparatus and the accessorial mobile apparatus for recording the before-bedtime calibration values of real-time blood sugar levels and blood pressure data.

FIG. 23 shows automated user interface 179 of the telemetry apparatus and synchronized accessorial mobile device for recording and accessing detailed diet information. The device automatically prompts the user to record detailed diet information of the meal name 180, meal quantity 181 and macronutrition and micronutrition 182.

Series of FIG. 24 show automated user interface of the telemetry apparatus and synchronized accessorial mobile device for accessing detailed real-time biological information. FIG. 24A is the automated interface 183 with real-time information on blood sugar levels, blood pressure data, neural activity, heart rate, oxygen saturation ratio and bio-temperature with health sense message 184. The health sense message 184 shows the current status and progress of the stress management and other health disorder management. FIG. 24B is the automated interface 185, which shows real-time information on current blood sugar levels 186 and past blood sugar trend 187. FIG. 24C is the sample interface 188, which shows real-time information on current blood pressure levels 189 and past blood pressure trend 190. FIG. 24D is the sample interface 191, which shows real-time information on pulse rate 192 and oxygen saturation ratio 193 with real-time signal pattern 194. The automated user interfaces are automatically displayed on the user device in a timely manner.

Figure 25A:
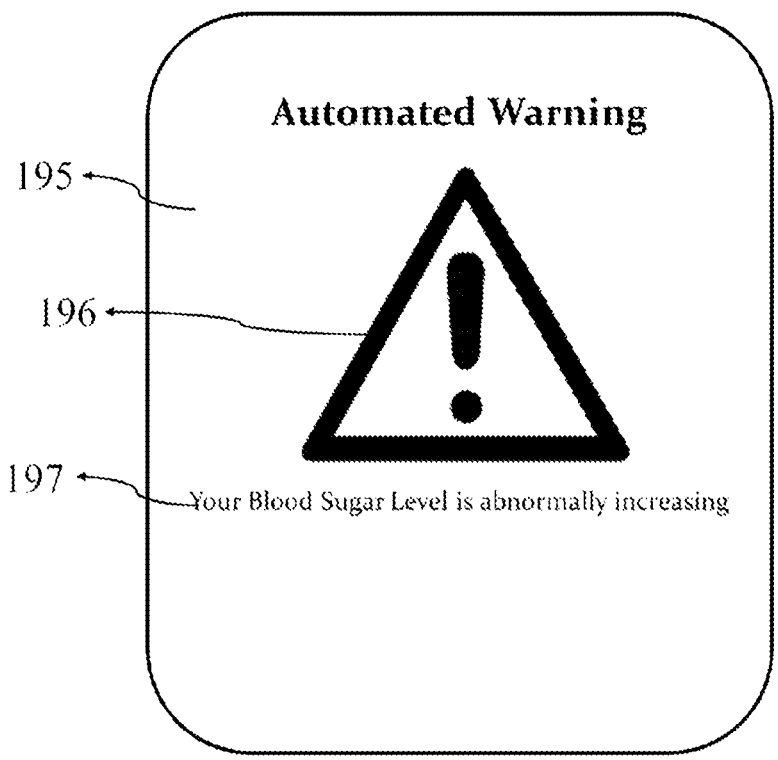
Figure 25B:
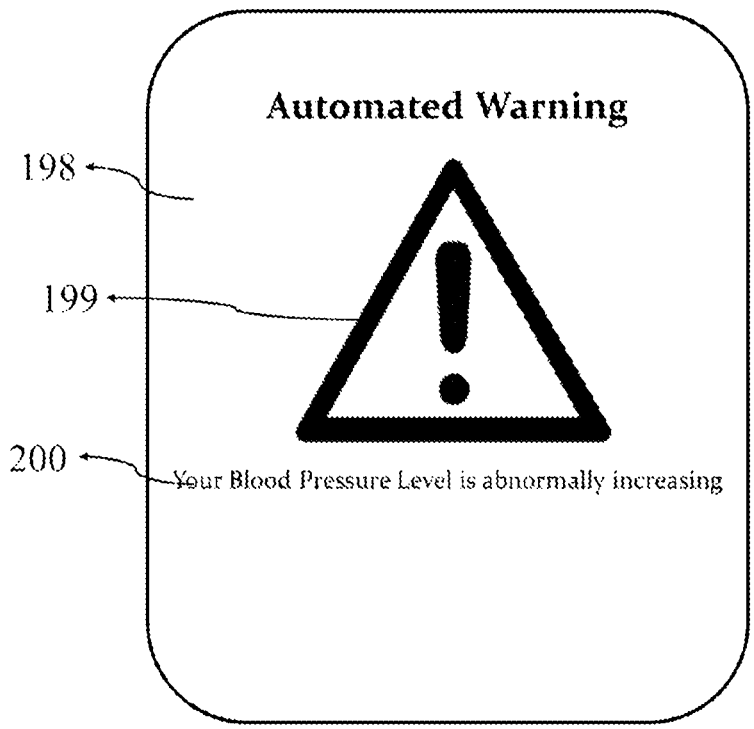
Figure 26A:
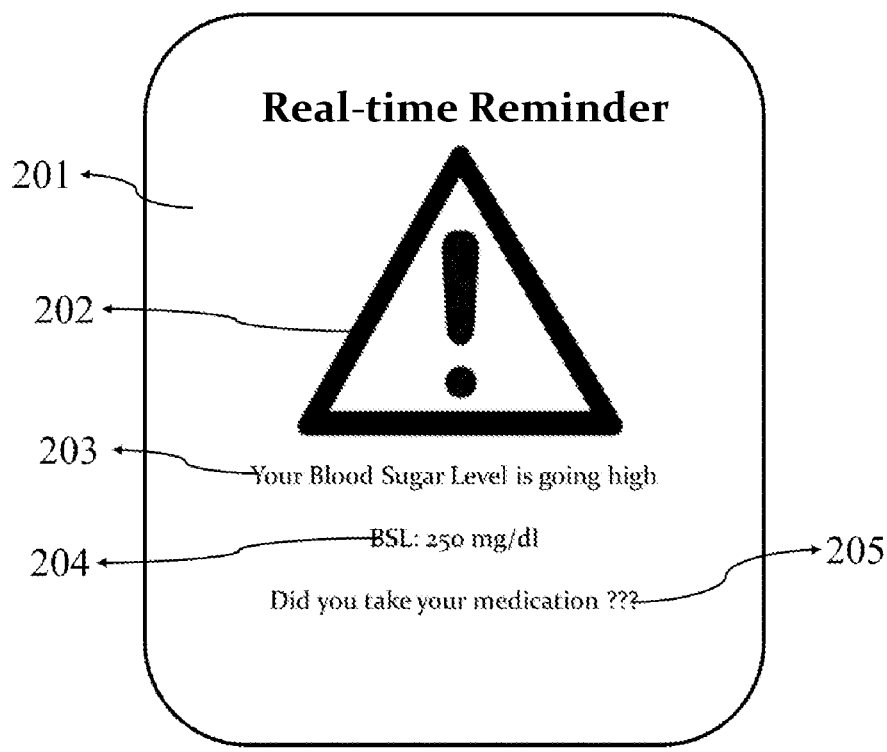
Figure 26B:
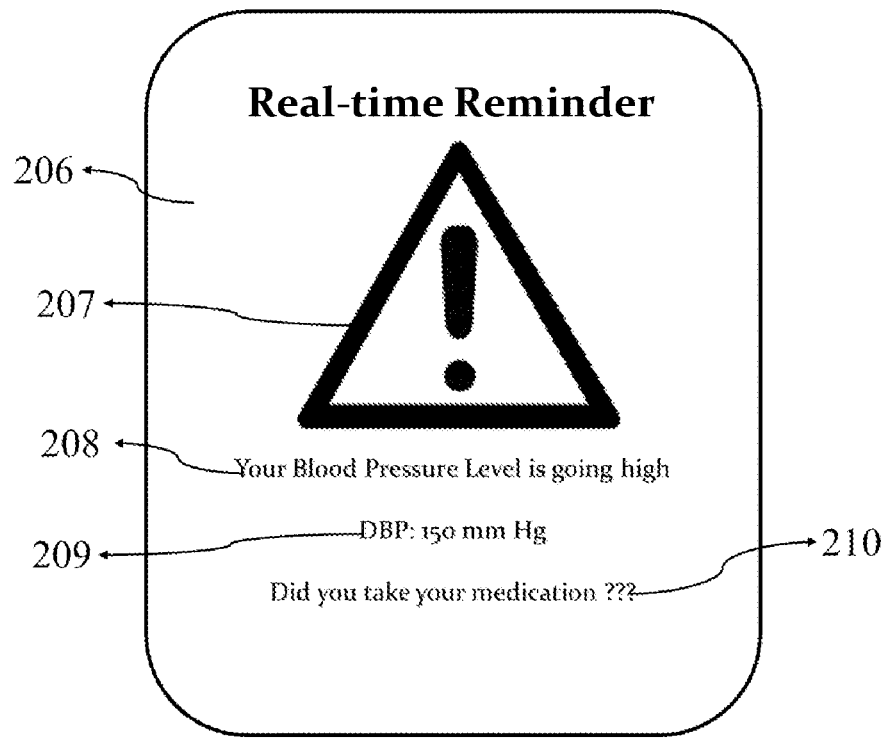
Figure 26C:
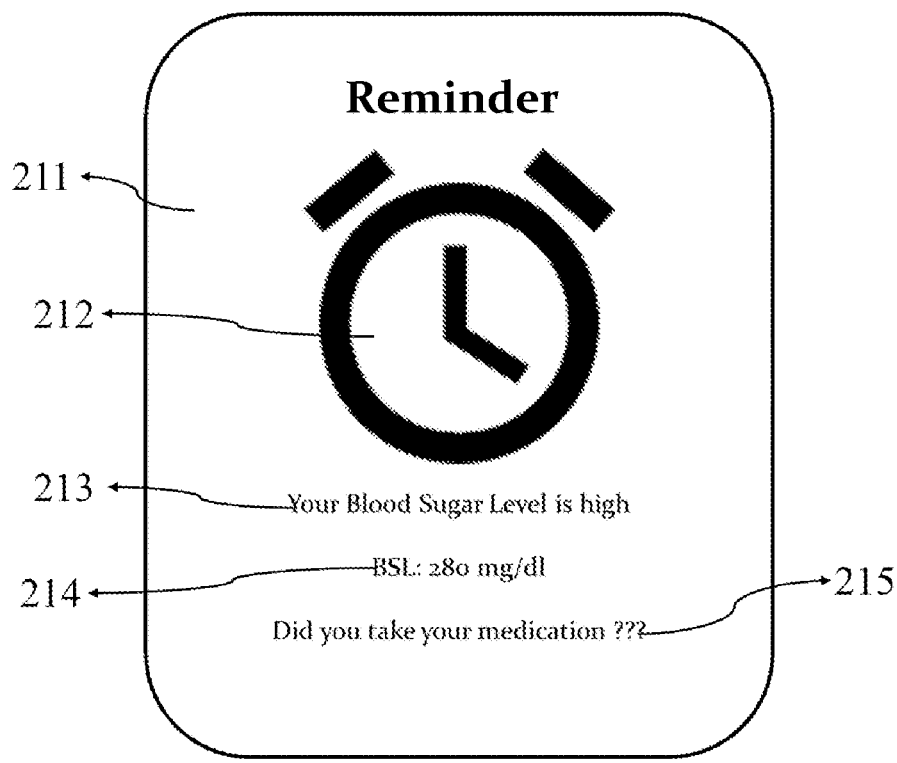
Figure 26D:
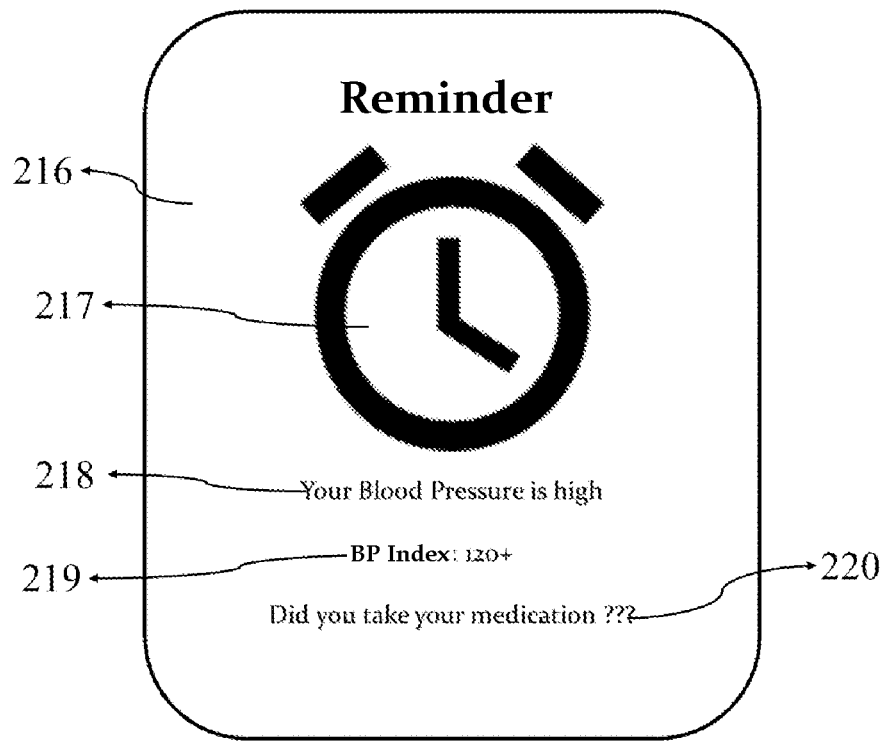

Series of FIG. 25 show sample interface of the automated real-time alerting system. FIG. 25A is the sample interface 195 that displays an automated warning 196 based on the real-time data with information on the unusual fluctuation (of the blood sugar levels 197). FIG. 25B is the sample interface 198 that displays an automated warning 199 based on the real-time data with information on the unusual fluctuation (of the blood pressure levels 200).

Series of FIG. 26 shows the real-time medication reminders that is displayed for unusual real-time biological data fluctuations and unusual physiological state. FIG. 26A is the interface 201 that displays an automated warning 202, unusual fluctuation message 203 and a medication reminder message 205 with information on real-time blood sugar levels 204. FIG. 26B is the interface 206 that displays an automated warning 207, unusual fluctuation message 208 and a medication reminder message 210 with information on real-time blood pressure 209. FIG. 26C is the interface 211 that displays an automated reminder 212, notification on blood sugar abnormality 213 and a medication reminder message 215 with information on real-time blood sugar levels 214. FIG. 26D is the interface 216 that displays an automated reminder 217, notification on blood pressure abnormality 218 and a medication reminder message 220 with information on real-time blood pressure levels 219.

Figure 27A:
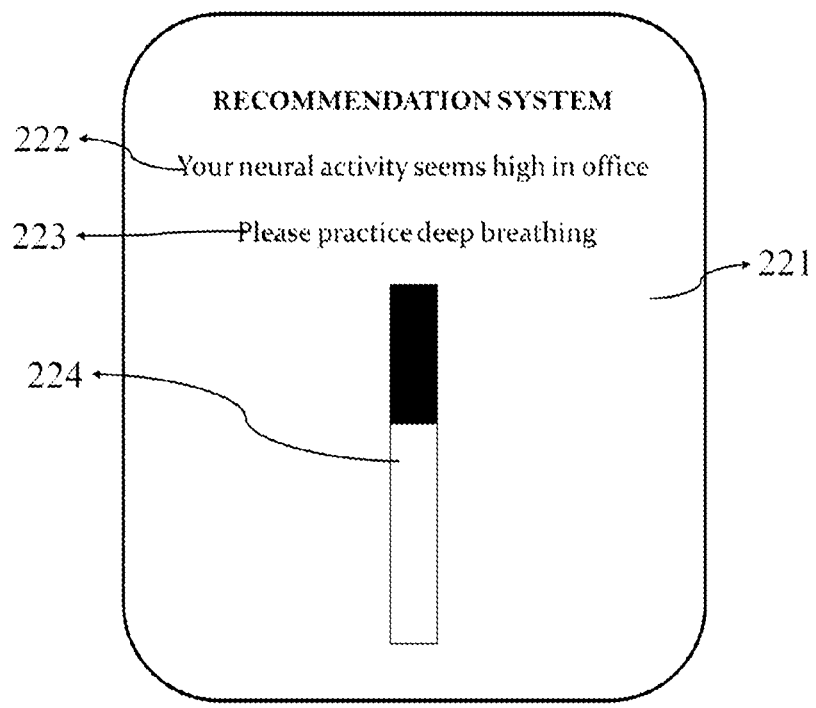
Figure 27B:
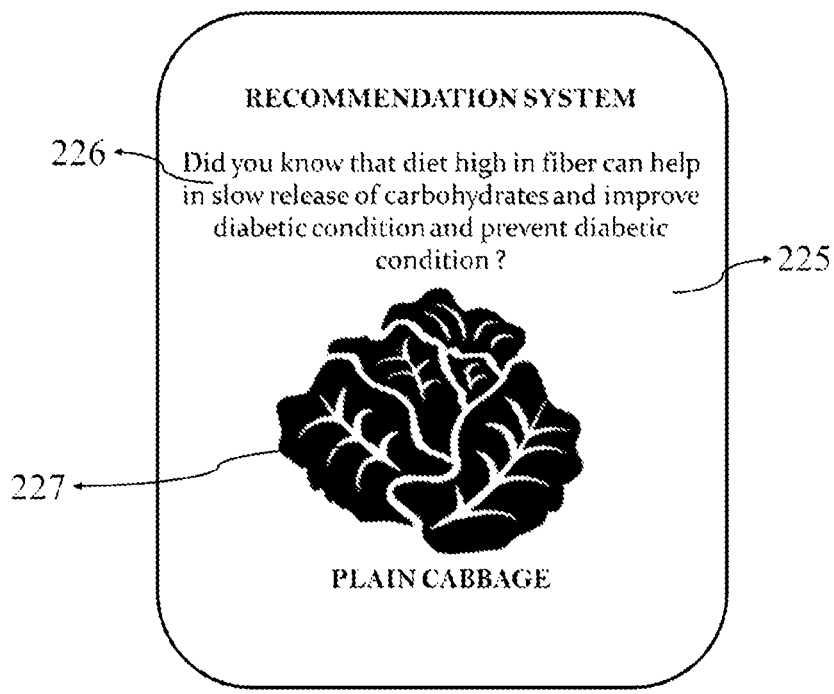

Series of FIG. 27 show the sample interface of the automated recommendation system. The automated recommendations are displayed on daily basis for specific health management purpose and also based on the real-time biological information. FIG. 27A is the sample interface 221 that displays unusual biological information with location 222, health management method 223 for the recognized health condition, and real-time physiological data 224. FIG. 27B is the sample interface 225 that displays diet management technique 227 for recognized health condition with additional scientific and nutritional information about the recommended diet 226.

Figure 28A:
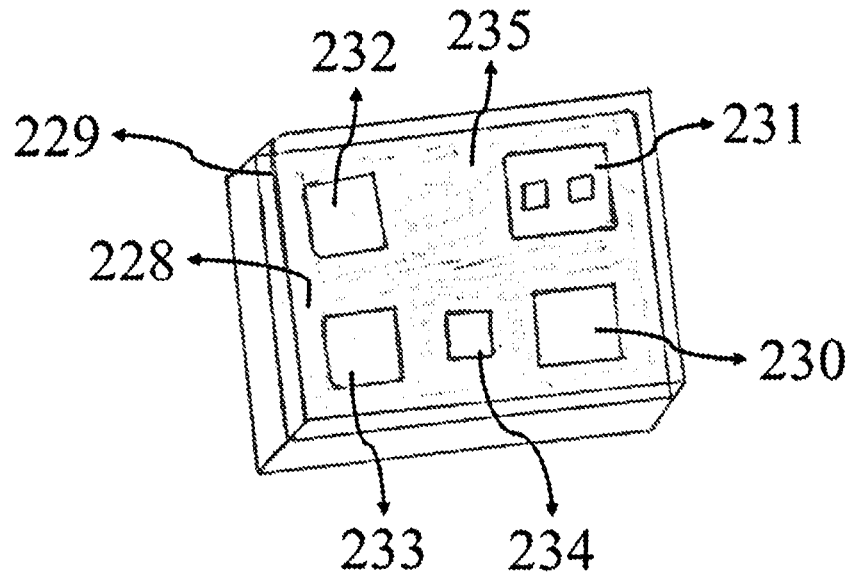
Figure 28B:
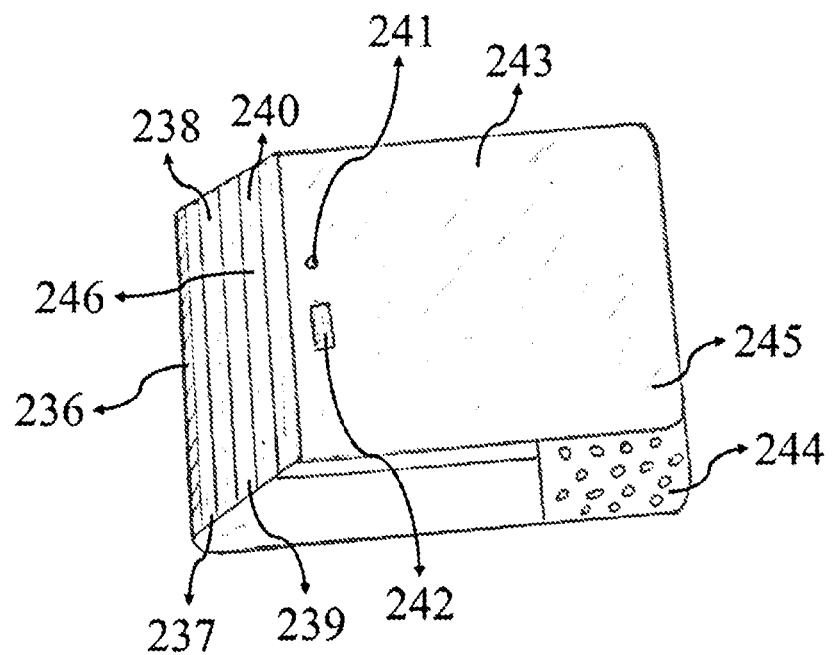
Figure 28C:
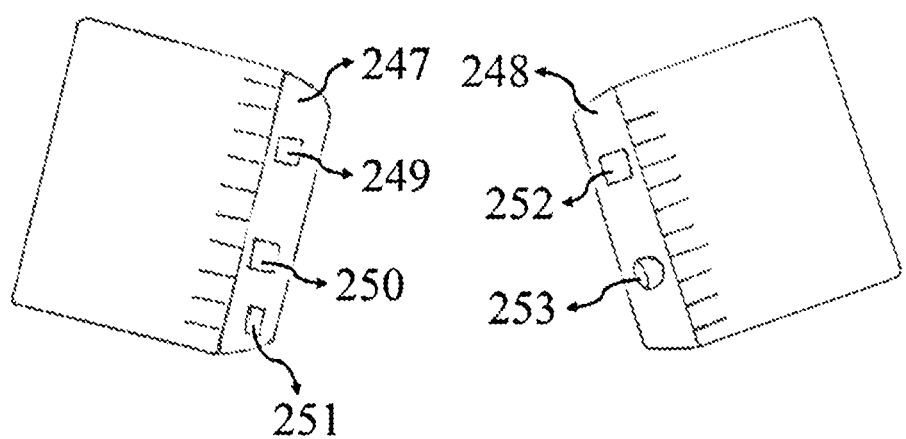

FIG. 28A, FIG. 28B and FIG. 28C show smart tracker embodiment of the telemetry apparatus.

FIG. 28A is the isometric bottom view of the smart watch embodiment. The set of near-infrared spectrometer apparatus 230, green spectrometer apparatus 231, infrared spectrometer 232, red spectrometer 233 and bio-temperature sensor 234 are embedded at optimal sensing spots on the contact surface 228 and inside a cavity like structure 229. The cavity like structure 229 is utilized as the means to curtail the background noise in the real-time response. A foam like material 235 is placed around the sensor area of the contact surface 228 of the smart tracker, which is used as the means to reduce contact vibration and real-time movement errors.

FIG. 28B shows the top packaging view of the smart watch. The bottom plane near the contact surface of the device comprises of the sensor plane 236. The sequential plane to the sensor plane 236 is packaged with analog and sensor end plane 237. The plane succeeding to the analog and sensor end plane 237 is packaged with secondary analog and digital plane 238. A power plane 239 is packaged between the secondary analog and digital plane 238 and primary digital and wireless plane 240, which is used as the means to reduce the electronic noise interruptions. The battery 244 of the device is placed on the other rear side end without obstructing the wireless and electronic plane. The aforementioned packaging method is utilized to reduce electronic circuit tracing and electronic noise interruptions. The top surface of the device comprises of mini-touchscreen 243, a micro-speaker 242 and mic 241. The electronic board of the device is covered with PCB waterproof coating 246 and the device is further covered with product water proofing coating 245 for extra protection.

FIG. 28C shows the isometric side view of the smart tracker embodiment. A micro-USB charging and data transfer port 251, button B1 249 and button B2 250 are placed on the side surface 247 of the device. The other side surface 248 of the device comprises of navigator 253 and button B3 252.

Figure 29A:
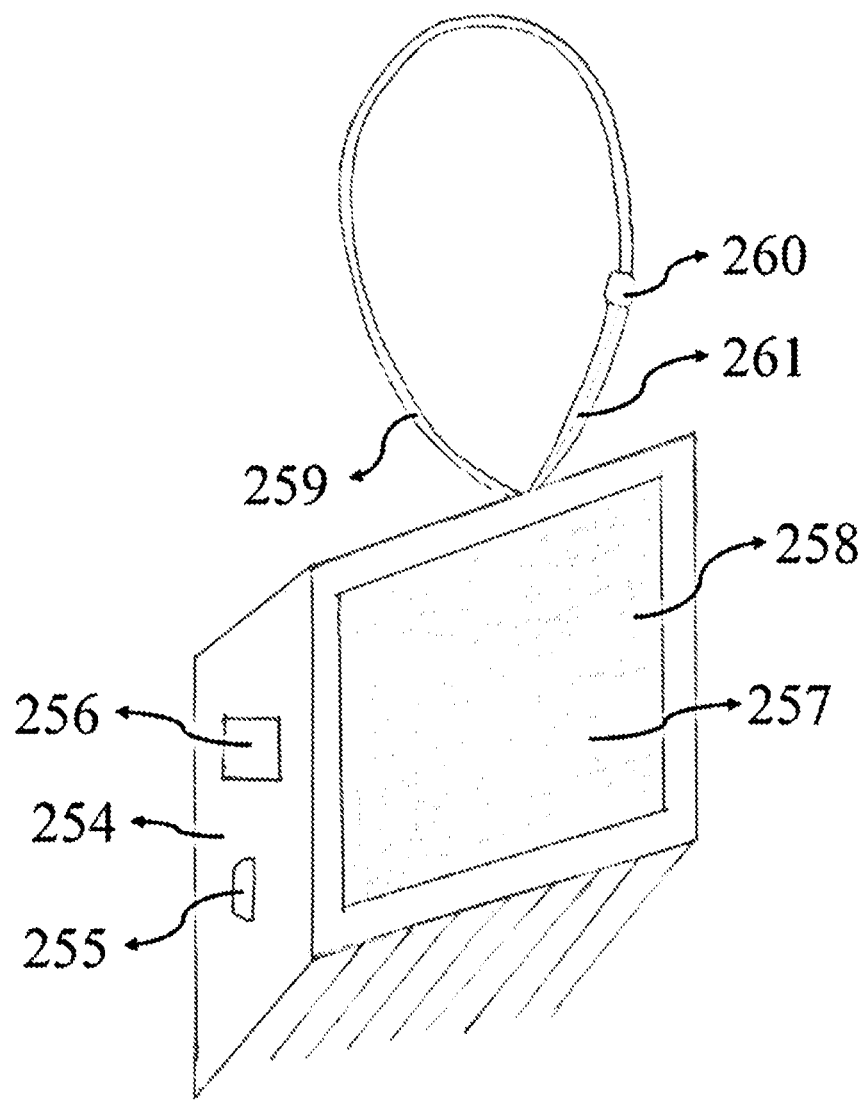

FIG. 29A shows the front isometric view of the handheld monitoring embodiment form. The micro-USB 255 and a button 256 are embedded on the side surface 254 of the monitor. The mini-touch screen 258 is embedded on the front side of the monitor, which is used to operate the apparatus and its inbuilt applications. The monitoring device is covered with waterproof coating 257. The device further comprises of a detachable wearable chord 259. The detachable chord 259 has a chord adjusting element 260 and an extender chord 261 for altering the size of the chord 259.

Figure 29B:
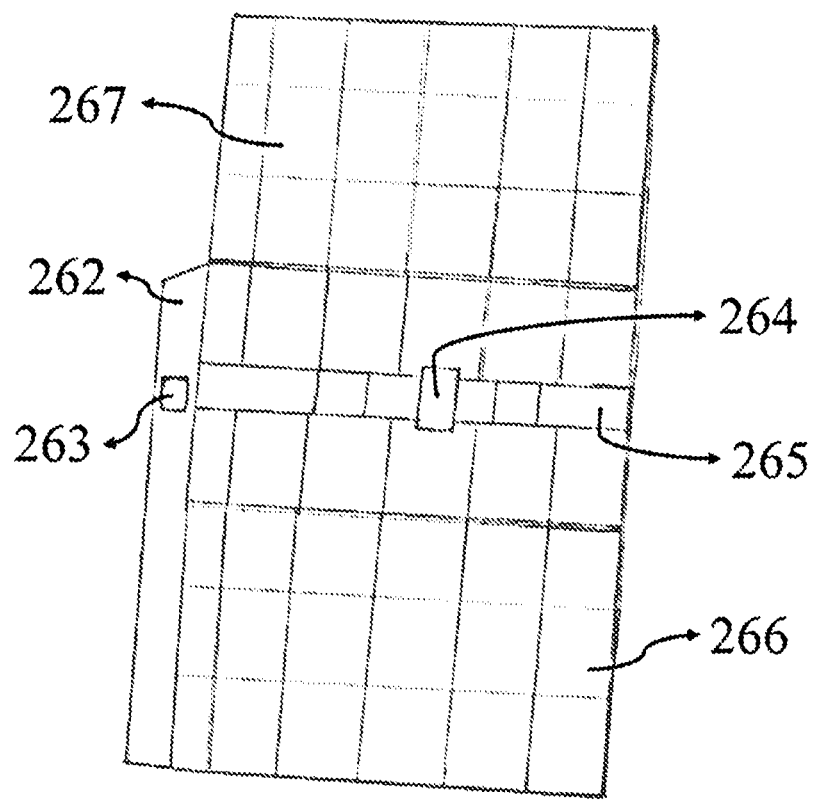

FIG. 29B shows the back-isometric view of the handheld monitor. A button 263 is embedded on the other side surface 262 of the monitor. A set of a detachable auxiliary powering module comprising of solar module 1 266, solar module 2 267, actuator hinge 265 and actuator 264 are attached to the back surface of the device. The actuator 264 extends the solar module 2 267 through the actuator hinge 265 from plane of solar module 1 266 for harvesting more solar energy. The actuation of the solar module 2 267 occurs automatically or through control commands.

Figure 29C:
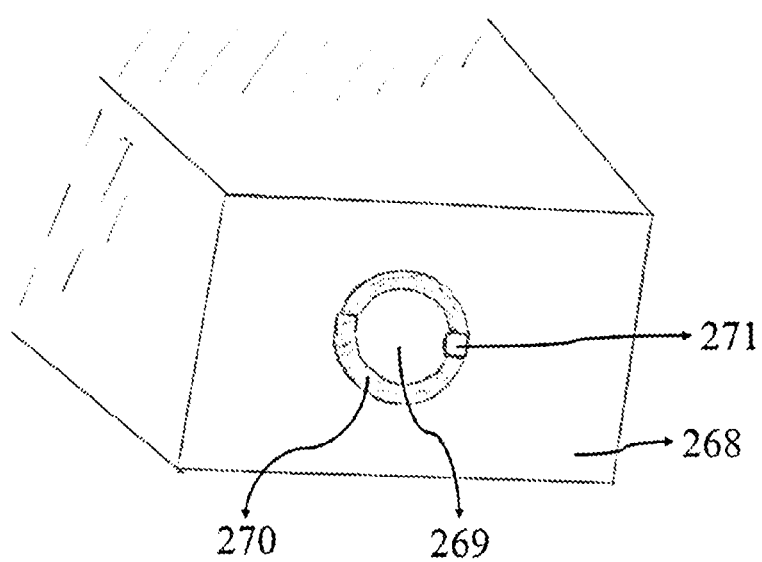

FIG. 29C shows the bottom isometric view of the handheld monitor. The bottom surface 268 of the monitor has a finger placement area 269 embedded with reflective bio-sensing apparatus 271. The area around the bio-sensors of the finger placement area 269 is surrounded by foam base or sponge 270. The foam base or sponge 270 is utilized to enhance the grip and reduce the real-time movement errors.

FIG. 30 shows the earphone embodiment of the telemetry apparatus. The earphone apparatus comprises of a reflective bio-sensing apparatus 272 with an ear placement area 273. The biosensing apparatus 272 is attached to the music ear-bud 276 through the ear hook clip 274. The fancy LED apparatus 275 is embedded inside the earphone near the ear hook 274. The device is covered with water proof coating 277. The ear-bud 276 and the ear hook 274 are used to securely hold the device on the sensing spot. The music ear-bud 276 is further utilized for perceiving audio output.

The above described invention disclosure is intended for illustration purposes, and for those skilled in the art may instantly perceive numerous suggestive modifications, variations and equivalents. Therefore, the disclosure is not exhaustive in broader aspects and the invention is not intended to limit to specific details, spectrometer instruments, illustrated hardware designs, described computational methods and embodiment forms. All equivalents and modifications are intended to be included within the scope of disclosure and attached claims. Accordingly, additional changes and modifications may be made without departing from the scope and the spirit of the invention disclosure appended in the document, claims and their equivalents.

INDUSTRIAL APPLICABILITY

The disclosure presents reflective sensing based low-powered and totally non-invasive continuous glucose monitoring solution. The described intelligent technology can be utilized as telemetry clinical instrumentation, neo-natal medical device, gestational diabetes monitoring apparatus, real-time diagnostic technology, portable medical apparatus, in-vitro and in-vivo biosensing instrument, general wellness management device, smart wearable device, server based real-time clinical diagnosis system, life-support device, health tracking software device, real-time intelligent medical reminder, automated recommendation system and software medical device.

PRIOR ART AND CITATION LIST

U.S. Pat. No. 4,882,492 A (Sensys Medical Inc) Nov. 21, 1989
U.S. Pat. No. 4,953,552 A (Arthur P. DeMarzo) Sep. 4, 1990
U.S. Pat. No. 4,979,509 A (Northstar Res Inst Ltd) Dec. 25, 1990
U.S. Pat. No. 5,139,023 A (Actavis Laboratories UT Inc Stanley Res Foundation) Aug. 18, 1992
U.S. Pat. No. 6,031,233 A (Infrared Fiber Systems) Feb. 29, 2000
U.S. Pat. No. 6,675,030 B2 (Euroceltique SA) Jan. 6, 2004
CN 102217939 A (Shanghai Jiao Tong University) Oct. 19, 2011
U.S. Pat. No. 8,280,476 B2 (ArKal Medical Inc) Oct. 2, 2012
CN 103349553 A (Zhao Wei) Oct. 16, 2013
WO 2014105520 A1 (Omni Medsci, Inc.) Jul 3, 2014

The invention claimed is:

1. A telemetry apparatus for monitoring physiological parameters, comprising:
   a near-infrared optical spectrometer configured to record a near-infrared response and to inject a near-infrared light at least at a glazing boundary angle, wherein the near-infrared optical spectrometer comprises:
      a plurality of near-infrared light sources configured to provide a constructive interference and to inject the near-infrared light;
      a first near-infrared optical lens system configured to constructively focus the near-infrared light on a sensing spot;
      a second near-infrared optical lens system configured to focus the near-infrared response on a first near-infrared photodetector, wherein the second near-infrared optical lens system and the first near-infrared photodetector are placed at an internal reflection noise eluding distance from the plurality of near-infrared light sources;
   an infrared optical spectrometer configured to record one or more first infrared optical responses, one or more second infrared optical responses, and an infrared optical dispersion signal of an infrared light;
   a red optical spectrometer configured to record one or more first red optical responses, one or more second red optical responses, and a red optical dispersion signal of a red light;
   a green optical spectrometer configured to record a green optical response;
   an optical dispersion analyzer module;
   a telemetry hardware comprising a microprocessor with memory, circuits and electronics, wherein the telemetry hardware is configured to extract:
      real-time blood sugar level data by correlating the near-infrared response with the one or more first infrared optical responses, the one or more second infrared optical responses, the one or more first red optical responses, the one or more second red optical responses, and the green optical response; and
      continuous blood pressure level data by correlating the green optical response with:
         (1) the one or more first red optical responses,
         (2) the one or more second red optical responses,
         (3) the one or more first infrared optical responses, or
         (4) the one or more second infrared optical responses.

2. The telemetry apparatus in claim 1, wherein the plurality of near-infrared light sources comprises an arrangement configured to provide the constructive interference, and wherein said arrangement comprises a respective distance between adjacent light sources of the plurality of near-infrared light sources.

3. The telemetry apparatus in claim 1, wherein the plurality of near-infrared light sources is tilted at a first angle to inject the near-infrared light at the glazing boundary angle to reflect the near-infrared light from a bone boundary, or
   wherein the first near-infrared optical lens system is tilted at a second angle to inject the near-infrared light at the glazing boundary angle to reflect the near-infrared light from the bone boundary.

4. The telemetry apparatus in claim 1, wherein the near-infrared optical spectrometer further comprises:
   a beam splitter configured to split the near-infrared light into a second near-infrared light in a refracted space and a third near-infrared light in a reflected space;
   a first secondary near-infrared lens system and a first mirror configured to inject the third near-infrared light in the reflected space at the glazing boundary angle;
   a second secondary near-infrared lens system configured to inject the second near-infrared light in the refracted space at the glazing boundary angle; and
   a third near-infrared optical lens system configured to focus a second near-infrared response from the reflected space on a second near-infrared photodetector.

5. The telemetry apparatus in claim 4, wherein the near-infrared optical spectrometer further comprises a set of mirrors configured to provide for a pathlength synchronization between the refracted space and the reflected space.

6. The telemetry apparatus in claim 1, wherein the infrared optical spectrometer comprises:
   an infrared LED and a first infrared optical lens system configured to emit and focus the infrared light on the sensing spot;

one or more first infrared photodetectors configured to record the one or more first infrared optical responses at one or more of an internal reflection free proximity position;

one or more second infrared optical lens systems configured to focus the one or more first infrared optical responses on the one or more first infrared photodetectors;

one or more second infrared photodetectors configured to record the one or more second infrared optical responses at one or more distant positions, wherein the one or more first infrared optical responses and the one or more second infrared optical responses are configured to provide the infrared optical dispersion signal; and one or more third infrared optical lens systems configured to focus the one or more second infrared optical responses on the one or more second infrared photodetectors.

7. The telemetry apparatus in claim 1, wherein the red optical spectrometer comprises:

a red LED and a first red optical lens system configured to emit and focus the red light on the sensing spot;

one or more first red photodetectors configured to record the one or more first red optical responses at one or more internal reflection free proximity positions;

one or more second red optical lens systems configured to focus the one or more first red optical responses on the one or more first red photodetectors;

one or more second red photodetectors configured to record the one or more second red optical responses at one or more of distant positions, wherein the one or more first red optical responses and the one or more second red optical responses are configured to provide the red optical dispersion signal; and one or more third red optical lens systems configured to focus the one or more second red optical responses on the one or more second red photodetectors.

8. The telemetry apparatus in claim 1, wherein the green optical spectrometer comprises:

a green LED and a first green optical lens system configured to emit and focus a green light at a critical angle on the sensing spot to reflect off from a skin boundary; and a green photodetector and a second green optical lens system configured to capture and record the green optical response.

9. The telemetry apparatus in claim 1, wherein the optical dispersion analyzer module is configured to inject a light from a light emitting probe towards a central photodetector system and is configured to extract real-time dispersion information from one or more of (1) a dispersive response from one or more non-central photodetector systems and (2) a central photodetector response of the central photodetector system.

10. The telemetry apparatus of claim 9, wherein the optical dispersion analyzer module comprises an instrumental amplifier configured to extract the real-time dispersion information from the one or more of the dispersive response and the central photodetector response; and wherein the light emitting probe is configured to emit a second green light, a second red light, or a second infrared light.

11. The telemetry apparatus in claim 1, wherein the telemetry hardware comprises:

a tuneable active amplifier circuit configured to coherently drive inputs to the plurality of near-infrared light sources;

a primary switch set configured to shift a plurality of input signals between a plurality of input lines of the near-infrared optical spectrometer, the green optical spectrometer, the infrared optical spectrometer and the red optical spectrometer to reduce a power consumption;

a LED frontend comprising an LED driver, an LED controller, a pulse width modulation unit (PWM) and a clock controller, wherein the LED frontend is configured to variably trigger and provide the plurality of input signals;

a photodetector primary switch set configured to shift a plurality of output responses to a photodetector circuit to reduce the power consumption, wherein the plurality of output responses comprises the near-infrared response, the one or more first infrared optical responses, the one or more second infrared optical responses, the one or more first red optical responses, the one or more second red optical responses and the green optical response;

one or more of a Darlington Pair circuit configured to amplify the plurality of output responses;

the photodetector circuit comprising a power notch, an ADC, a first ambient noise cancellation IC and an amplifier, wherein the photodetector circuit is configured to filter noises in and process the plurality of output responses;

a set of switches configured to alternatively drive the one or more first infrared optical responses, the one or more second infrared optical responses, the one or more first red optical responses, and the one or more second red optical responses, respectively, to a proximity response line and a distant response line;

one or more second ambient noise cancellation ICs configured to filter noises in the proximity response line and the distant response line;

a dispersion analyzer circuit comprising an instrumental amplifier, wherein the dispersion analyzer circuit is configured to extract a real-time dispersion information from the proximity response line and the distant response line;

a temperature biosensor configured to extract a real-time body temperature and a first temperature feedback to adjust the plurality of output responses;

an ambient temperature sensor configured to extract a real-time environment temperature and a second temperature feedback to adjust the plurality of output responses;

an accelerometer configured to provide a real-time motion feedback to remove a motion noise and to compute a plurality of movement data;

a touch display configured to provide access to a plurality of calibrations, a plurality of real-time medical information, a plurality of medical alerts, and a plurality of automated recommendations;

a microphone and a speaker configured for interacting with a plurality of medical and health professionals for a clinical and health analysis and for operating the telemetry apparatus;

a navigator crown comprising a potentiometer and a fixed impedance component;

a plurality of buttons, wherein the plurality of buttons and the navigator crown are configured to provide the access to the plurality of calibrations and to operate the telemetry apparatus;

a display LED circuit configured to automatically indicate a user condition and to represent a plurality of operating modes and device status;

a wireless antennae set configured to:
  extract location data and the plurality of movement data; and
  communicate to a life-support network and a network of external computational devices;
a power management IC configured to regulate a power supply;
a first supercapacitor and a battery set configured to store energy and supply power;
a second supercapacitor and a renewable energy harvester configured to provide auxiliary power;
a negative voltage converter configured to generate a negative signal reference; and
a wireless coil configured to wirelessly supply the power and charge the battery set.

12. The telemetry apparatus in claim 11, wherein the wireless antennae set comprises a mobile communication module configured to: extract the location data and the plurality of movement data; and communicate to the life-support network and the network of external computational devices.

13. The telemetry apparatus in claim 11, wherein the plurality of buttons and the navigator crown are configured to:
  swap operating modes and swap internal applications of a current mode;
  facilitate a wireless synchronization of the telemetry hardware with the network of external computational devices for an IoT parallel computational mode, wherein the IoT parallel computational mode is configured to execute a parallel computing to extract a plurality of real-time biological information;
  enable marking of a psychological stress level; and
  enable a silent trigger of an emergency alert and a trigger of a medical emergency alert in the life-support network.

14. The telemetry apparatus in claim 1, wherein the telemetry hardware is configured to extract the real-time blood sugar level data by correlating the near-infrared response with the one or more first infrared optical responses, the one or more second infrared optical responses, the one or more first red optical responses, the one or more second red optical responses, and the green optical response by:
  obtaining an area normalized value of the near-infrared response;
  obtaining an area normalized value of an infrared power response, an integrated infrared response, and a differential infrared response, wherein the infrared power response, the integrated infrared response, and the differential infrared response are deduced from the one or more first infrared optical responses and the one or more second infrared optical responses;
  obtaining an area normalized value of a red power response, an integrated red response, and a differential red response, wherein the red power response, the integrated red response, and the differential red response are deduced from the one or more first red optical responses and the one or more second red optical responses;
  obtaining an area normalized value of the green optical response;
  deducing a green parameter from a DC parameter of the green optical response;
  deducing a red oscillatory response from the integrated red response;
  adjusting the near-infrared response as per temperature stats according to a bio-temperature response and an ambient temperature response obtained from a temperature biosensor and an ambient temperature sensor of the telemetry hardware, respectively;
  deducing a color index from analysis of a plurality of RGB indices of a plurality of contact pictures of the sensing spot;
  obtaining a processed near-infrared response through a correlation of the near-infrared response with at least the red oscillatory response, the green parameter, the differential red response, the integrated red response, the red power response, the differential infrared response, the integrated infrared response, the infrared power response, or the color index to adjust for blood line losses, skin losses, blood particle losses and dispersion losses;
  correlating the processed near infrared response with one or more of a blood sugar calibration value comprising a pre-meal value, a post-meal value, a post-morning-sleep value, a fasting-glucose value, a post-exercise value, a before-bed-time value, a sitting-position value, a standing-position value, a relaxing-position value, a hyperglycemia-state value and a hypoglycemia-state value;
  extracting blood sugar fluctuation data from the real-time blood sugar level data;
  recognizing a hypoglycemic condition, a hyperglycemic condition, and a prediabetes condition by analyzing the real-time blood sugar level data and the blood sugar fluctuation data in a fasting-glucose state, a post-meal state, a post-sleep state, a regular-condition state and a pre-meal state;
  recognizing a blood sugar condition by analyzing the real-time blood sugar level data and the blood sugar fluctuation data with respect to a user location that includes a restaurant location, wherein said blood sugar condition is the hypoglycemic condition, the hyperglycemic condition, or the prediabetes condition;
  tracking the blood sugar condition by analyzing the real-time blood sugar level data and the blood sugar fluctuation data over a period of time that includes evaluating the blood sugar fluctuation data for a fluctuation value of at least 70 over at least a 4 hour time period;
  verifying the blood sugar condition through a reverification in a same state and a cross verification in a different state that includes analysis in the fasting-glucose state, the post-meal state and the regular-condition state;
  running a recalibration on recognizing the hypoglycemic condition or the hyperglycemic condition;
  analyzing the differential red response, the integrated red response, the red power response, the differential infrared response, the integrated infrared response, and the infrared power response to learn and recognize the hypoglycemic condition, the hyperglycemic condition, and the prediabetes condition;
  verifying symptoms and automatically provide a plurality of recommendations on therapy methods, treatment centers, lifestyle practices, diet suggestions, required physical activities, mitigation methods, and medication advice to treat and manage the blood sugar condition;
  automatically presenting a real-time medical alert, a message to consult a doctor, a medication reminder, and a location of medication based on the blood sugar condition;

automatically alerting a life-support network and a physician network on recognizing the blood sugar condition with a warning message and information on the blood sugar condition, the user location, user data, the blood sugar fluctuation data and the real-time blood sugar level data; and automatically warning the user and the life-support network on recognizing a pattern of rapidly increasing values of the real-time blood sugar level data and heart rate data, with mitigation methods and the location of medication.

15. The telemetry apparatus in claim 1, wherein the telemetry hardware is configured to extract the continuous blood pressure level data by correlating the green optical response with:

(1) the one or more first red optical responses, (2) the one or more second red optical responses, (3) the one or more first infrared optical responses, or (4) the one or more second infrared optical responses by:

obtaining an oscillatory signal involving a green parameter, wherein the green parameter is extracted from the green optical response, wherein the oscillatory signal is extracted from (1) the one or more first red optical responses, (2) the one or more second red optical responses, (3) the one or more first infrared optical responses, or (4) the one or more second infrared optical responses;

obtaining a power of the oscillatory signal for a fixed time span;

correlating the power of the oscillatory signal with one or more of a blood pressure calibration value comprising a regular condition value, a pre-meal value, a post-meal value, a post morning sleep value, a fasting glucose value, a post exercise value, a before bed time value, a sitting position value, a standing position value, a relaxing position value, a hyperglycemia state value, and a hypoglycemia state value;

extracting blood pressure fluctuation data from the continuous blood pressure level data;

recognizing a stage 1 hypertension condition, a stage 2 hypertension condition, a low blood pressure condition, and a prehypertension condition by analyzing the continuous blood pressure level data and the blood pressure fluctuation data in a fasting glucose state, a post-meal state, a post-sleep state, a post-meditation state, a regular condition state, and a pre-meal state;

verifying a blood pressure condition through a reverification in a same state and a cross verification in a different state that includes analysis in an early morning state, the post-meal state, the post-meditation state and the regular condition state, wherein the blood pressure condition is at least the stage 1 hypertension condition, the stage 2 hypertension condition, the low blood pressure condition, or the prehypertension condition;

recognizing the blood pressure condition by analyzing the continuous blood pressure level data and the blood pressure fluctuation data with respect to a user location;

verifying the blood pressure condition through a symptom verification that includes a dizziness feeling for the low blood pressure condition;

verifying symptoms and automatically provide a plurality of recommendations on therapy methods, treatment centers, lifestyle practices, diet suggestions, required physical activities, mitigation methods, and medication advice to treat and manage the blood pressure condition;

automatically presenting a real-time medical alert, a message to consult a doctor, a medication reminder, and a location of medication based on the blood pressure condition; and automatically alerting a life-support network and a physician network on recognizing the blood pressure condition with a warning message and information on the blood pressure condition, the user location, user data, the continuous blood pressure level data and the blood pressure fluctuation data.

16. The telemetry apparatus in claim 1, wherein the telemetry hardware is configured to:

extract an emotional stress by:

verifying the continuous blood pressure level data and fluctuation data of the continuous blood pressure level data for a threshold of stress levels;

obtaining an HP1 parameter through evaluation of interval difference data, between peak to peak temporal data, with a fixed interval difference, wherein the fixed interval difference is at least a 0.05 seconds and the peak to peak temporal data is extracted from analysis of the one or more first red optical responses and the one or more second red optical responses;

obtaining a HP2 parameter by taking a root of an average of a square of the interval difference data;

obtaining a HP3 parameter by taking an average of the peak to peak temporal data; and comparing a present data set of the HP1 parameter, the HP2 parameter and the HP3 parameter with a resting data set of the HP1 parameter, the HP2 parameter and the HP3 parameter;

verifying a state of the emotional stress through an assessment of a user location related to stress, wherein the user location related to stress includes a work location and a home location;

notifying the user on the state of the emotional stress and automatically provide a plurality of recommendations on exercise, guided meditation, diet, and social networking platforms to manage the state of the emotional stress; and automatically alerting a life-support network on recognizing the emotional stress with a warning message and information on the user location and user data.

17. The telemetry apparatus in claim 1, wherein the telemetry hardware is configured to:

recognize and record a sleep state, a rapid eye movement (REM) sleep cycle, and a non-rapid eye movement (NREM) sleep cycle by:

evaluating movement data, a body temperature, the continuous blood pressure level data, and the real-time blood sugar level data for a realistic range and for the sleep state, wherein the body temperature and the movement data are deduced from a temperature biosensor, a wireless antennae set, and an accelerometer of the telemetry hardware;

evaluating a real-time dataset of the continuous blood pressure level data, the real-time blood sugar level data, a HP1 parameter, a HP2 parameter, and a HP3 parameter with a sleep dataset and a wake dataset to recognize the REM sleep cycle and the NREM sleep cycle, wherein the HP1 parameter, the HP2 parameter, and the HP3 parameter are extracted from the one or more first red optical responses;

storing a REM sleep cycle duration, a NREM sleep cycle duration and an overall sleep duration;

recognize a disturbed sleep state by analyzing the movement data and sleep results data of the sleep state, the REM sleep cycle, and the NREM sleep cycle;
verify symptoms and automatically provide a plurality of recommendations on recovery techniques, meditation methods, therapy methods, treatment centers, lifestyle practices, diet suggestions, physical activities, medications, and health advice to treat and manage the disturbed sleep state;
automatically alert a life-support network on recognizing the disturbed sleep state with a warning message and information on a user location and user data; and
reduce a count of analysis parameters.

18. The telemetry apparatus in claim 1, wherein the telemetry hardware is configured to:
transmit an age, a color index, a BMI, a fat percentage, a plurality of calibration values, and a plurality of sensor signals and intensity responses of a user to a central server, wherein the plurality of sensor signals and intensity responses comprises a plurality of output responses from the near-infrared optical spectrometer, the infrared optical spectrometer, the red optical spectrometer and the green optical spectrometer;
receive a plurality of optimization parameters and health parameters comprising sensor calibration data, a health range index, a performance index, and a progress index from a central database of the central server, wherein the plurality of optimization parameters and health parameters are derived based on learning of a plurality of previously recorded data of users; and
process a plurality of real-time biological information of the user by implementing the plurality of optimization parameters and health parameters, wherein the plurality of real-time biological information comprises the real-time blood sugar level data, the continuous blood pressure level data, emotional stress data, sleep state data, rapid eye movement sleep cycle data, non-rapid eye movement sleep cycle data, and a plurality of medical and health conditions.

19. A system comprising:
the telemetry apparatus of claim 1; and
a plurality of devices of a life-support network,
wherein the system is configured to:
validate a status of a wireless antennae set of the telemetry apparatus and switch on the wireless antennae set in a switched off state on recognizing an emergency trigger;
record location data from the wireless antennae set;
record a plurality of real-time biological information from a plurality of sensors of the telemetry apparatus, wherein the plurality of sensors includes a temperature biosensor, an ambient temperature sensor, an accelerometer, the near-infrared optical spectrometer, the infrared optical spectrometer, the red optical spectrometer, and the green optical spectrometer; and
transmit the location data and the plurality of real-time biological information to a central server, a plurality of SOS network devices, and a plurality of nearby devices in a user location through a plurality of wireless connections established by (1) the plurality of devices of the life-support network and (2) the wireless antennae set or a medium of the central server.

20. A system comprising:
the telemetry apparatus of claim 1;
a server computer; and
a plurality of accessorial mobile devices and external computers,
wherein the telemetry hardware, the server computer, the plurality of accessorial mobile devices, and the external computers are configured to:
execute a parallel computing to increase speed of computations of a plurality of real-time biological information through a plurality of wireless connections established by a wireless antennae set of the telemetry hardware, wherein the plurality of real-time biological information comprises the real-time blood sugar level data, the continuous blood pressure level data, emotional stress data, sleep state data, rapid eye movement sleep cycle data, non-rapid eye movement sleep cycle data, and a plurality of medical and health conditions.

21. A system comprising:
the telemetry apparatus of claim 1; and an accessorial mobile device,
wherein the accessorial mobile device or the telemetry apparatus is configured to:
record a plurality of user information comprising a profile picture, a user name, an age, a basal metabolic index, a fat percentage, a weight, a height and a gene info;
record one or more of a contact picture of the sensing spot;
record a plurality of blood sugar and blood pressure calibration values during a device startup stage of the telemetry apparatus, a fasting glucose state, a post morning sleep state, a post-meal state, a pre-meal state, a post-exercise state and a before-bedtime state;
record a macro-nutrition detail, a micro-nutrition detail and a meal information;
display a real-time information and a data trend on a plurality of real-time biological information, wherein the plurality of real-time biological information comprises the real-time blood sugar level data, the continuous blood pressure level data, a neural activity, a pulse rate, an oxygen saturation, and a body temperature;
display a health sense message that shows a current status and a progress on stress management and health disorder management;
display an automated warning to indicate an unusual fluctuation of one or more of the plurality of real-time biological information;
automatically display a real-time reminder comprising a medication reminder message, one or more of the plurality of real-time biological information, and a notification on abnormality of one or more of the plurality of real-time biological information; and
display an automated recommendation comprising a recognized health condition along with a location, one or more of the plurality of real-time biological information, a health management technique, and a diet management technique with an additional scientific and nutritional information.

22. The telemetry apparatus of claim 1, wherein the telemetry apparatus further comprises:
a cavity structure configured to curtail a background noise in a plurality of real-time responses of a plurality of biosensors, wherein the plurality of biosensors is embedded in the cavity structure and the plurality of biosensors comprises the near-infrared optical spectrometer, the infrared optical spectrometer, the red optical spectrometer, the green optical spectrometer and a temperature biosensor;

a touch screen configured to provide access to a plurality of calibrations, a plurality of real-time biological information, a plurality medical alerts, and a plurality of automated recommendations;

a segregated layer packaging of the telemetry hardware configured to curtail an electronic noise interruption and to reduce a circuit tracing, wherein said segregated layer packaging is segregated as at least one or more of an analog and sensor frontend plane, a secondary analog and digital plane, a primary digital and wireless plane, and a power plane;

a battery packaging configured to elude a signal interference to at least a wireless antennae set by placing a battery nonobstructively in the telemetry hardware, wherein the wireless antennae set and the battery are comprised in the telemetry hardware;

a foam base on a contact surface around the plurality of biosensors, wherein the foam base is configured to reduce a movement error;

a PCB waterproof coating; and a product waterproof coating.

23. The telemetry apparatus of claim 1, wherein the telemetry apparatus further comprises:

an ear placement area configured to hold a plurality of biosensors in a reflective sensing configuration, wherein the plurality of biosensors comprises the near-infrared optical spectrometer, the infrared optical spectrometer, the red optical spectrometer, and the green optical spectrometer;

a foam base on a contact surface around the plurality of biosensors, wherein the foam base is configured to reduce a movement error;

an ear hook clip configured to securely fasten the telemetry apparatus on the sensing spot;

a music ear bud configured to securely hold the telemetry apparatus on the sensing spot;

a display LED embedded near the ear hook clip, wherein the display LED is configured to display different device modes and device status; and a waterproof coating.

24. The telemetry apparatus of claim 1, wherein the telemetry apparatus further comprises:

a touch screen configured to provide an access to a plurality of calibrations, a plurality of real-time biological information, a plurality of medical alerts and a plurality of automated recommendations;

a finger placement area configured to hold a plurality of biosensors in a reflective sensing configuration, wherein the plurality of biosensors comprises the near-infrared optical spectrometer, the infrared optical spectrometer, the red optical spectrometer and the green optical spectrometer;

a temperature biosensor embedded in the finger placement area, wherein the temperature biosensor is configured to extract a real-time bio-temperature signals and a thermal feedback;

a foam base embedded on the finger placement area around the plurality of biosensors, wherein the foam base is configured to enhance a mechanical gripping and reduce a movement error;

a detachable auxiliary powering module comprising a first solar module and a second solar module, wherein the detachable auxiliary powering module is configured to harvest a solar energy;

an actuator configured to extend the second solar module from a plane of the first solar module to harvest the solar energy; and a waterproof coating.

* * * * *